United States Patent
Nyati et al.

(10) Patent No.: US 9,029,502 B2
(45) Date of Patent: May 12, 2015

(54) INHIBITORS OF THE EPIDERMAL GROWTH FACTOR RECEPTOR-HEAT SHOCK PROTEIN 90 BINDING INTERACTION

(75) Inventors: Mukesh K. Nyati, Ann Arbor, MI (US); Theodore S. Lawrence, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 495 days.

(21) Appl. No.: 13/329,800

(22) Filed: Dec. 19, 2011

(65) Prior Publication Data

US 2012/0190622 A1 Jul. 26, 2012

Related U.S. Application Data

(60) Provisional application No. 61/425,100, filed on Dec. 20, 2010.

(51) Int. Cl.
| | |
|---|---|
| A61K 38/08 | (2006.01) |
| C07K 7/00 | (2006.01) |
| C07K 17/00 | (2006.01) |
| A61K 38/00 | (2006.01) |
| C12P 21/04 | (2006.01) |
| C07K 14/71 | (2006.01) |

(52) U.S. Cl.
CPC ............... *C07K 14/71* (2013.01); *A61K 38/00* (2013.01); *C07K 2319/10* (2013.01)

(58) Field of Classification Search
USPC ................ 530/328, 329; 514/19.3; 435/69.7; 424/185.1
See application file for complete search history.

(56) References Cited

U.S. PATENT DOCUMENTS

| | | | |
|---|---|---|---|
| 3,691,016 | A | 9/1972 | Patel |
| 3,969,287 | A | 7/1976 | Jaworek et al. |
| 4,195,128 | A | 3/1980 | Hildebrand et al. |
| 4,229,537 | A | 10/1980 | Hodgins et al. |
| 4,247,642 | A | 1/1981 | Hirohara et al. |
| 4,330,440 | A | 5/1982 | Ayers et al. |
| 4,399,276 | A | 8/1983 | Miyasaka et al. |
| 4,473,692 | A | 9/1984 | Miyasaka et al. |
| 4,513,138 | A | 4/1985 | Miyasaka et al. |
| 4,526,988 | A | 7/1985 | Hertel |
| 4,545,880 | A | 10/1985 | Miyasaka et al. |
| 4,604,463 | A | 8/1986 | Miyasaka et al. |
| 4,808,614 | A | 2/1989 | Hertel |
| 4,946,778 | A | 8/1990 | Ladner et al. |
| 5,004,758 | A | 4/1991 | Boehm et al. |
| 5,087,616 | A | 2/1992 | Myers et al. |
| 5,180,722 | A | 1/1993 | Wall et al. |
| 5,223,608 | A | 6/1993 | Chou et al. |
| 5,225,539 | A | 7/1993 | Winter |
| 5,234,784 | A | 8/1993 | Aslam et al. |
| 5,403,484 | A | 4/1995 | Ladner et al. |
| 5,449,752 | A | 9/1995 | Fujii et al. |
| 5,474,982 | A | 12/1995 | Murray et al. |
| 5,512,545 | A | 4/1996 | Brown et al. |
| 5,545,806 | A | 8/1996 | Lonberg et al. |
| 5,569,825 | A | 10/1996 | Lonberg et al. |
| 5,571,698 | A | 11/1996 | Ladner et al. |
| 5,585,089 | A | 12/1996 | Queen et al. |
| 5,620,985 | A | 4/1997 | Jacquesy et al. |
| 5,639,641 | A | 6/1997 | Pedersen et al. |
| 5,693,761 | A | 12/1997 | Queen et al. |
| 5,693,762 | A | 12/1997 | Queen et al. |
| 5,702,892 | A | 12/1997 | Mulligan-Kehoe |
| 5,714,352 | A | 2/1998 | Jakobovits |
| 5,780,279 | A | 7/1998 | Matthews et al. |
| 5,821,047 | A | 10/1998 | Garrard et al. |
| 5,824,520 | A | 10/1998 | Mulligan-Kehoe |
| 5,837,500 | A | 11/1998 | Ladner et al. |
| 5,855,885 | A | 1/1999 | Smith et al. |
| 5,858,657 | A | 1/1999 | Winter et al. |
| 5,871,907 | A | 2/1999 | Winter et al. |
| 5,969,108 | A | 10/1999 | McCafferty et al. |
| 6,057,098 | A | 5/2000 | Buechler et al. |
| 6,225,447 | B1 | 5/2001 | Winter et al. |
| 6,265,150 | B1 | 7/2001 | Terstappen et al. |
| 6,551,592 | B2 | 4/2003 | Lindhofer et al. |
| 6,630,124 | B1 | 10/2003 | Gozes et al. |

(Continued)

FOREIGN PATENT DOCUMENTS

| | | |
|---|---|---|
| EP | 0056692 | 7/1982 |
| EP | 0074256 | 3/1983 |

(Continued)

OTHER PUBLICATIONS

Citri et al., 2004, Hsp90 restrains ErbB-2/HER2 signaling by limiting heterodimer formation, EMBO reports, 5(12): 1165-1170.*
Nyati et al., 2006, Integration of EGFR inhibitors with radiochemotherapy, Nature Reviews, 6: 876-885.*
Futaki et al., 2001, Arginine-rich Peptides, The Journal of Biological Chemistry, 276(8): 5836-5840.*
Adjei et al., Pulmonary delivery of peptide drugs: effect of particle size on bioavailability of leuprolide acetate in healthy male volunteers, *Pharmaceutical Research*, 7(6):565-9 (1990).
Ahsan et al., Role of cell cycle in epidermal growth factor receptor inhibitor-mediated radiosensitization, *Cancer Res.*, 69:5108-14 (2009).
Ahsan et al., Role of epidermal growth factor receptor degradation in cisplatin-induced cytotoxicity in head and neck cancer, *Cancer Res.*, 70:2862-9 (2010).

(Continued)

*Primary Examiner* — Amber D Steele
(74) *Attorney, Agent, or Firm* — Marshall, Gerstein & Borun LLP

(57) ABSTRACT

Provided herein are compounds that inhibit a binding interaction between an epidermal growth factor receptor (EGFR) and a heat shock protein 90 (HSP90), as well as compositions, e.g., pharmaceutical compositions, comprising the same, and related kits. In some embodiments, the compound is an antibody or antibody analog, and, in other embodiments, the compound is a peptide or peptide analog. Also provided are methods of using the compounds, including methods of increasing degradation of an EGFR, methods of treating cancer, and methods of sensitizing tumors to radiation therapy.

11 Claims, 13 Drawing Sheets

(56) References Cited

U.S. PATENT DOCUMENTS

| | | | |
|---|---|---|---|
| 6,699,843 | B2 | 3/2004 | Pietras et al. |
| 7,355,008 | B2 | 4/2008 | Stavenhagen et al. |
| 7,381,408 | B2 | 6/2008 | Mezo et al. |
| 7,608,413 | B1* | 10/2009 | Joseloff et al. ............... 435/7.23 |
| 7,799,781 | B2 | 9/2010 | Nowak |
| 8,303,960 | B2* | 11/2012 | Capala et al. ............... 424/193.1 |
| 2002/0137141 | A1* | 9/2002 | Ben-Sasson ................. 435/69.1 |
| 2002/0164687 | A1 | 11/2002 | Eriksson et al. |
| 2002/0164710 | A1 | 11/2002 | Eriksson et al. |
| 2002/0197266 | A1 | 12/2002 | Debinski |
| 2004/0071671 | A1* | 4/2004 | Leturcq et al. ............... 424/93.21 |
| 2005/0282233 | A1 | 12/2005 | Eriksson et al. |
| 2010/0009860 | A1 | 1/2010 | Fischer et al. |
| 2010/0233084 | A1* | 9/2010 | Narasimhaswamy et al. . 424/9.1 |
| 2010/0249231 | A1 | 9/2010 | Sun et al. |
| 2010/0298331 | A1 | 11/2010 | Lee et al. |

FOREIGN PATENT DOCUMENTS

| | | |
|---|---|---|
| EP | 0074770 | 3/1983 |
| EP | 0088642 | 9/1983 |
| EP | 0137145 | 4/1985 |
| EP | 0184365 | 6/1986 |
| EP | 0239400 | 9/1987 |
| EP | 0321122 | 6/1989 |
| EP | 0418099 | 3/1991 |
| EP | 1568373 A2 | 8/2005 |
| GB | 2188638 | 10/1987 |
| WO | WO 98/28621 | 7/1998 |
| WO | WO 99/40942 | 8/1999 |
| WO | WO 00/32218 | 6/2000 |
| WO | WO-02/48336 A2 | 6/2002 |
| WO | WO 02/060950 | 8/2002 |
| WO | WO-02/065992 A2 | 8/2002 |
| WO | WO 2004/033036 | 4/2004 |
| WO | WO 2005/087812 | 9/2005 |
| WO | WO 2007/133747 | 11/2007 |
| WO | WO 2007/141411 | 12/2007 |

OTHER PUBLICATIONS

Andrew, Martin's Kabat Man web page (http://www.bioinf.org.uk/abs/kabatman.html), 2 pages.

Andrews et al., Forming stable helical peptides using natural and artificial amino acids, *Tetrahedron*, 55:11711-43 (1999).

Armour et al., Recombinant human IgG molecules lacking Fcgamma receptor I binding and monocyte triggering activities, *Eur. J. Immunol.*, 29:2613-2624 (1999).

Banker et al. (eds), Pharmaceutics and Pharmacy Practice, J. B. Lippincott Company, Philadelphia, PA, 238-50 (1982).

Bao et al., Targeting heat shock protein 90 with CUDC-305 overcomes erlotinib resistance in non-small cell lung cancer, *Mol. Cancer Ther.*, 8:3296-306 (2009).

Blackwell et al., Highly efficient synthesis of covalently cross-linked peptide helicies by ring-closing metathesis, *Angew, Chem. Int. Ed.*, 37:3281-4 (1998).

Brody et al., Aptamers as therapeutic and diagnostic agents, *J. Biotechnol.*, 74:5-13 (2000).

Burmeister et al., Crystal structure of the complex of rat neonatal Fc receptor with Fc, *Nature*, 372:379-383 (1994).

Chun et al., Synergistic effects of gemcitabine and gefitinib in the treatment of head and neck carcinoma, *Cancer Res.*, 66:981-8 (2006).

Citri et al., Hsp90 restrains ErbB-2/HER2 signaling by limiting heterodimer formation, *EMBO Rep.*, 5:1165-70 (2004).

Cole et al., The EBV-hybridoma technique and its application to human lung cancer, Monoclonal Antibodies and Cancer Therapy, Alan R Liss Inc, New York N.Y., 77-96 (1985).

Cote et al., Generation of human monoclonal antibodies reactive with cellular antigens, *Proc. Natl. Acad. Sci.*, 80:2026-30 (1983).

Creighton, Proteins: Structure and Molecule Properties, W. H. Freeman & Co., San Francisco, 79-86 (1983).

Davies, The cyclization of peptides and depsipeptides, *J. Peptide. Sci.*, 9: 471-501 (2003).

Davis et al., Single chain antibody (SCA) encoding genes: one-step construction and expression in eukaryotic cells, *Nature Biotechnology*, 9:165-9 (1991).

Dote et al., ErbB3 expression predicts tumor cell radiosensitization induced by Hsp90 inhibition, *Cancer Res.*, 65:6967-75 (2005).

Feng et al., Role of epidermal growth factor receptor degradation in gemcitabine-mediated cytotoxicity, *Oncogene*, 26:3431-9 (2007).

Friend et al., Phase I study of an engineered aglycosylated humanized CD3 antibody in renal transplant rejection, *Transplantation*, 68:1632-1637 (1999).

Fukase et al., Synthetic study on peptide antibiotic nisin. V. Total synthesis of nisin, *Bull. Chem. Soc. Jpn.*, 65:2227-40 (1992).

Futaki et al., Arginine-rich peptides—An abundant source of membrane-permeable peptides having potential as carriers for intracellular protein delivery, *J. Biol, Chem.*, 276:5836-40 (2001).

Ghadiri et al., Secondary structure nucleation in peptides. Transition metal ion stabilized .alpha.-helices, *J. Am. Chem. Soc.*, 112:1630-2 (1990).

Goodman et al., Peptidomimetic building blocks for drug discovery: An overview, *Pure Appl. Chem.*, 68:1303-8 (1996).

Gyurkocza et al., Antileukemic activity of shepherdin and molecular diversity of hsp90 inhibitors, *J. Natl. Cancer Inst.*, 98:1068-77 (2006).

Harpp et al., Preparation and mass spectral properties of cystine and lanthionine derivatives. A novel synthesis of L-lanthionine by selective desulfurization, *J. Org. Chem.*, 36:73-80 (1971).

Haskard et al., The production of human monoclonal autoantibodies from patients with rheumatoid arthritis by the EBV-hybridoma technique, *J. Immunol. Methods*, 74(2):361-7 (1984).

Henry et al., Participation of the N-terminal region of Cepsilon3 in the binding of human IgE to its high-affinity receptor FcepsilonRI, *Biochemistry*, 36:15568-78 (1997).

Houston et al., Lactam bridge stabilization of alpha-helical peptides: ring size, orientation and positional effects, *J. Peptide Sci.*, 1:274-82 (2004).

Huang et al., Growth hormone-induced phosphorylation of epidermal growth factor (EGF) receptor in 3T3-F442A cells. Modulation of EGF-induced trafficking and signaling, *J. Biol. Chem.*, 278:18902-13 (2003).

Huse et al., Generation of a large combinatorial library of the immunoglobulin repertoire in phage lambda, *Science*, 246:1275-81 (1989).

Jackson et al., General approach to the synthesis of short alpha-helical peptides, *J. Am. Chem. Soc.*, 113: 9391-2 (1991).

Jacobs et al., Surface modification for improved blood compatibility, *Artif. Organs*, 12:506-507 (1988).

Jentzmik et al., Sarcosine in urine after digital rectal examination fails as a marker in prostate cancer detection and identification of aggressive tumours, *Eur. Urol.*, 58:12-8 (2010).

Jones et al., Replacing the complementarity-determining regions in a human antibody with those from a mouse, *Nature*, 321 :522-5 (1986).

Karpishin et al., Copper-driven assembly of a helical-peptide-strapped porphyrin, *J. Am. Chem. Soc.*,119:9063-4 (1997).

Karpovsky et al., Production of target-specific effector cells using hetero-cross-linked aggregates containing anti-target cell and anti-Fc gamma receptor antibodies, *J. Exp. Med.*, 160:1686-701 (1984).

Kawashima et al., Pulmonary delivery of insulin with nebulized DL-lactide/glycolide copolymer (PLGA) nanospheres to prolong hypoglycemic effect, *J. Controlled Release*, 62(1-2):279-87 (1999).

Kim et al., Nonthrombogenic bioactive surfaces, *Ann. N.Y. Acad. Sci.*, 516:116-30 (1987).

Kim et al., Update on Hsp90 inhibitors in clinical trial, *Curr. Top Med. Chem.*, 9:1479-92 (2009).

Koehler et al., Continuous cultures of fused cells secreting antibody of predefined specificity, *Nature*, 256:495-7 (1975).

Kortt et al., Dimeric and trimeric antibodies: high avidity scFvs for cancer targeting, *Biomol. Eng.*, 18:95-108 (2001).

Kozbor et al., The production of monoclonal antibodies from human lymphocytes, *Immunol. Today*, 4:72-79 (1983).

(56) References Cited

OTHER PUBLICATIONS

Lavictoire et al., Interaction of Hsp90 with the nascent form of the mutant epidermal growth factor receptor EGFRvIII, *J. Biol. Chem.*, 278:5292-9 (2003).
Levkowitz et al., c-Cbl/Sli-1 regulates endocytic sorting and ubiquitination of the epidermal growth factor receptor, *Genes Dev.*, 12:3663-74 (1998).
Levkowitz et al., Ubiquitin ligase activity and tyrosine phosphorylation underlie suppression of growth factor signaling by c-Cbl/Sli-1, *Molecular cell*, 4:1029-40 (1999).
Lewis et al., Structural requirements for the interaction of human IgA with the human polymeric Ig receptor, *J Immunol.*, 175:6694-701 (2005).
Liu et al., Pulmonary delivery of free and liposomal insulin, *Pharm. Res .*,10(2):228-32 (1993).
Marvin et al., Recombinant approaches to IgG-like bispecific antibodies, *Acta. Pharmacologica Sin.*, 26:649-58 (2005).
Matteucci et al., Cystine mimetics—solid phase lanthionine synthesis, *Tetrahedron Letters*, 45:1399-401 (2004).
Mayer et al., Lanthionine macrocyclization by in situ activation of serine, *J. Peptide Res.*, 51:432-4 (1998).
Morrison et al., Lanthionine macrocyclization by in situ activation of serine, *Proc. Natl. Acad. Sci. USA*, 81:6851-5 (1984).
NCBI Protein Database as Accession No. NP_005219, Epidermal growth factor receptor isoform a precursor [*Homo sapiens*], May 24, 1999, 14 pages.
NCBI Protein Database as Accession No. NP_958439.1, Epidermal growth factor receptor isoform b precursor [*Homo sapiens*], Jan. 26, 2004, 6 pages.
NCBI Protein Database as Accession No. NP_958440.1, Epidermal growth factor receptor isoform c precursor [*Homo sapiens*], Jan. 26, 2004, 5 pages.
NCBI Protein Database as Accession No. NP_958441, Epidermal growth factor receptor isoform d precursor [*Homo sapiens*], Jan. 26, 2004, 6 pages.
Neckers et al., The complex dance of the molecular chaperone Hsp90, *Trends Biochem. Sci.*, 34:223-6 (2009).
Neuberger et al., Recombinant antibodies possessing novel effector functions, *Nature*, 312:604-8 (1984).
Nitta et al., Proc. 14th International Congr. Chemotherapy, Kyoto, Tokyo Press, Anticancer,1: 28-30 (1985).
Niwa et al., Antitumor effects of epidermal growth factor receptor antisense oligonucleotides in combination with docetaxel in squamous cell carcinoma of the head and neck, *Clin. Cancer Res.*, 9:5028-35 (2003).
Nyati et al., Integration of EGFR inhibitors with radiochemotherapy, *Nature Reviews*, 6:876-85 (2006).
Nyati et al., Radiosensitization by pan ErbB inhibitor CI-1033 in vitro and in vivo, *Clin. Cancer Res.*, 10:691-700 (2004).
Olofsson et al., Vascular endothelial growth factor B (VEGF-B) binds to VEGF receptor-1 and regulates plasminogen activator activity in endothelial cells, *Proc. Natl. Acad. Sci. USA*, 95:11709-14 (1998).
Orlandi et al., Cloning immunoglobulin variable domains for expression by the polymerase chain reaction, *Proc. Natl. Acad. Sci. USA*, 86:3833-7 (1989).
Osapay et al., Lanthionine-somatostatin analogs: synthesis, characterization, biological activity, and enzymatic stability studies, *J. Med. Chem.*, 40:2241-51 (1997).
Osapay et al., New application of peptide cyclization on an oxime resin (the PCOR method): preparation of lanthionine peptides, *J. Chem. Soc. Chem. Commun.*, 1599-600 (1993).
Owens et al., The genetic engineering of monoclonal antibodies, *J. Immunol. Meth.*, 168:149-65 (1994).
Park et al., Blood compatibility of SUUU-PEO-heparin graft copolymers, *J. Biomed. Mat. Res.*, 26:739-45 (1992).
Park et al., Synthesis and characterization of SPUU-PEO-heparin graft copolymers, *J. Poly. Sci, Part A*, 29:1725-31 (1991).
Pedersen et al., Comparison of surface accessible residues in human and murine immunoglobulin Fv domains. Implication for humanization of murine antibodies, *J. Mol. Biol.*, 235:959-73 (1994).
Phelan et al., A general method for constraining short peptides to an alpha-helical conformation, *J. Am. Chem. Soc.*, 119: 455-460 (1997).
Pick et al., High HSP90 expression is associated with decreased survival in breast cancer, *Cancer Res.*, 67, 2932-7 (2007).
Plescia et al., Rational design of shepherdin, a novel anticancer agent, *Cancer cell*, 7:457-68 (2005).
Polinsky et al., Synthesis and conformational properties of the lanthionine-bridged opioid peptide [D-AlaL2,AlaL5]enkephalin as determined by NMR and computer simulations, *J. Med. Chem.*, 35:4185-94 (1992).
Pratt et al., The Hsp90 chaperone machinery regulates signaling by modulating ligand binding clefts, *J. Biol. Chem.*, 283:22885-9 (2008).
Price et al., The heat shock protein 90 inhibitor, 17-allylamino-17-demethoxygeldanamycin, enhances osteoclast formation and potentiates bone metastasis of a human breast cancer cell line, *Cancer Res.*, 65:4929-38 (2005).
Qian et al., Pulmonary delivery of a GLP-1 receptor agonist, BMS-686117, *Int. J. Pharm.*, 366:218-20 (2009).
Qian et al., Sustained release subcutaneous delivery of BMS-686117, a GLP-1 receptor peptide agonist, via a zinc adduct, *J. Pharm.*, 374:46-52 (2009).
Reiter et al., Engineering interchain disulfide bonds into conserved framework regions of Fv fragments: improved biochemical characteristics of recombinant immunotoxins containing disulfide-stabilized Fv, *Protein Engineering*, 7:697-704 (1994).
Riechmann et al., Reshaping human antibodies for therapy, *Nature*, 332:323-7 (1988).
Roder et al., The EBV-hybridoma technique, *Methods Enzymol.*, 121 :140-67 (1986).
Routledge et al., The effect of aglycosylation on the immunogenicity of a humanized therapeutic CD3 monoclonal antibody, *Transplantation*, 60:847-853 (1995).
Rudinger et al., A biologically active analogue of oxytocin not containing a disulfide group, *Experientia*, 20:570-1 (1964).
Sato et al., Modulation of Akt kinase activity by binding to Hsp90, *Proc. Natl. Acad. Sci. USA*, 97:10832-7 (2000).
Sawhney et al., Bioerodible hydrogels based on photopolymerized poly(ethylene glycol)-co-poly(alpha-hydroxy acid) diacrylate macromers, *Macromolecules*, 26:581-7 (1993).
Sayers et al., The importance of Lys-352 of human immunoglobulin E in FcepsilonRII/CD23 recognition, *J. Biol. Chem.*, 279(34):35320-5 (2004).
Schafmeister et al., An all-hydrocarbon cross-linking system for enhancing the helicity and metabolic stability of peptides, *J. Am. Chem. Soc.*, 122:5891-2 (2000).
Seebach et al., Beta-peptides: Synthesis by Arndt-Eisert homologation with concomitant peptide coupling. Structure determination by NMR and CD spectroscopy and by X-ray crystallography. Helical secondary structure of beta-hexapeptide in solution and its stability towards pepsin, *Helvetica Chimica Acta*, 79(4):913-41 (1996).
Sharp et al., Inhibitors of the HSP90 molecular chaperone: current status, *Adv. Cancer Res.*, 95:323-48 (2006).
Sheehan et al., Total synthesis of a monocyclic peptide lactone antibiotic, etamycin, *J. Am. Chem. Soc.*, 95: 875-9 (1973).
Shimamura et al., Epidermal growth factor receptors harboring kinase domain mutations associate with the heat shock protein 90 chaperone and are destabilized following exposure to geldanamycins, *Cancer Res.*, 65:6401-8 (2005).
Shimamura et al., Hsp90 inhibition suppresses mutant EGFR-T790M signaling and overcomes kinase inhibitor resistance, *Cancer Res.*, 68:5827-38 (2008).
Sidera et al., A critical role for HSP90 in cancer cell invasion involves interaction with the extracellular domain of HER-2, *J. Biol. Chem.*, 283:2031-41 (2008).
Solit et al., Phase I trial of 17-allylamino-17-demethoxygeldanamycin in patients with advanced cancer, *Clinical Cancer Research*, 13:1775-82 (2007).
Sondermann et al., The 3.2-A crystal structure of the human IgG1 Fc fragment-Fc gamma RIII complex, *Nature*, 406:267-73 (2000).
Takeda et al., Construction of chimaeric processed immunoglobulin genes containing mouse variable and human constant region sequences, *Nature*, 314:452-4 (1985).

(56) References Cited

OTHER PUBLICATIONS

Titus et al., Human T cells targeted with anti-T3 cross-linked to antitumor antibody prevent tumor growth in nude mice, *J. Immunol.*, 138:4018-22 (1987).
Todorovska et al., Design and application of diabodies, triabodies and tetrabodies for cancer targeting, *J. Immunol. Methods*, 248:47-66 (2001).
Toissel, ASHP Handbook on Injectable Drugs, 4th ed., 622-30 (1986).
Van Tellingen et al., Pharmacology, bio-analysis and pharmacokinetics of the vinca alkaloids and semi-synthetic derivatives (review), *Anticancer Research*, 12:1699-16 (1992).
Verhoeyen et al., Reshaping human antibodies: grafting an antilysozyme activity, *Science*, 239:1534-6 (1988).
Veronese et al., Preparation and Properties of Monomethoxypoly(ethylene glycol)-modified Enzymes for Therapeutic Applications, *Biotechnical and Biomedical Applications*, 127-36 (1992).
Wadhwa et al., Receptor mediated glycotargeting, *J. Drug Targeting*, 3:111-27 (1995).
Wadia et al., Transmembrane delivery of protein and peptide drugs by TAT-mediated transduction in the treatment of cancer, *Adv. Drug Deliv. Rev.*, 57:579-96 (2005).
Walensky et al., Activation of apoptosis in vivo by a hydrocarbon-stapled BH3 helix, *Science*, 305:1466-70 (2004).
Wani et al, Plant antitumor agents. 18. Synthesis and biological activity of camptothecin analogues, *J. Med. Chem.*, 23:554 (1980), 554-560.
Wani et al., Plant antitumor agents. 23. Synthesis and antileukemic activity of camptothecin analogues, *J. Med. Chem.*, 29:2358-63 (1986).
Wani et al., Plant antitumor agents. 25. Total synthesis and antileukemic activity of ring A substituted camptothecin analogues. Structure-activity correlations, *J. Med. Chem.*, 30:1774-1779 (1987).
Ward et al., The effector functions of immunoglobulins: implications for therapy, *Therapeutic Immunology*, 2:77-94 (1995).
Weihua et al., Survival of cancer cells is maintained by EGFR independent of its kinase activity, *Cancer cell*, 13:385-93 (2008).
Winter et al., Man-made antibodies, *Nature*, 349:293-9 (1991).
Workman, Altered states: selectively drugging the Hsp90 cancer chaperone, *Trends Mol. Med.*, 10:47-51 (2004).
Yang et al., Association with HSP90 inhibits Cbl-mediated down-regulation of mutant epidermal growth factor receptors, *Cancer Res.*, 66:6990-7 (2006).
Zuckermann et al., Efficient method for the preparation of peptoids [oligo(N-substituted glycines)] by submonomer solid-phase synthesis, *JACS*, 114(26):10646-7 (1992).
International Search Report and Written Opinion of the International Searching Authority, Korean Intellectual Property Office, PCT/US2011/065865, dated Jun. 27, 2012.
International Preliminary Report on Patentability, PCT/US2011/065865, dated Jun. 27, 2012.
Blagosklonny et al., Leukemia, "The HSP90 Inhibitor Geldanamycin Selectively Sensitizes BCR-ABL-Expressing Leukemia Cells to Cytotoxic Chemotherapy", 15:1537-1543 (2001).
Gius, Radiotherapy and Oncology, "Increased Radiosensitization in Cervical Tumor Cells Following HSP90 Inhibition with Geldanamycin", vol. 73, S106, 234 oral (Oct. 2004).
Database Accession No. CS151513 (2005) from EP 1568373 A2.
Extended European Search Report dated Apr. 14, 2014 for counterpart European Application No. 11851905.7.

\* cited by examiner

INHIBITORS OF THE EPIDERMAL GROWTH FACTOR RECEPTOR-HEAT SHOCK PROTEIN 90 BINDING INTERACTION

This application claims the benefit of U.S. Provisional Patent Application No. 61/425,100 filed Dec. 20, 2010. The provisional application is hereby incorporated by reference in its entirety.

STATEMENT OF GOVERNMENT INTEREST

This invention was made with government support under Grant No. CA131290, awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 71 kilobytes ACII (Text) file named "45776_SeqListing.txt," created on Dec. 7, 2010.

BACKGROUND

The Epidermal Growth Factor Receptor (EGFR) is a validated therapeutic target for the treatment of many cancers. However, the inhibition of EGFR has proven effective only in a limited subset of patients[1].

The limitations of these cancer therapeutics may be due to the fact that the therapeutics aim to inhibit the tyrosine kinase activity of EGFR. A recent study showed that the knockdown of EGFR with small interfering RNA led to cell death in an autophagic process, independently of EGFR receptor tyrosine kinase activity[2]. Accordingly, the inhibition of EGFR tyrosine kinase activity alone is likely insufficient to cause cytotoxicity of EGFR driven tumors.

A further drawback of some EGFR-targeted cancer therapeutics currently used in the clinical setting is that drug resistance often develops after initial use of the therapeutic. For example, while non-small cell lung cancer is initially sensitive to erlotinib, resistance develops upon subsequent administrations of this drug.

In view of the foregoing, there exists a need for a cancer therapeutic that targets EGFR in a manner other than inhibition of EGFR tyrosine kinase activity. There also exists a need for a therapeutic that treats cancer without drug resistance developing after initial use.

SUMMARY

For the first time, it is shown herein that EGFR binds to Heat Shock Protein 90 (HSP90), and that specific disruption of this binding interaction induces EGFR degradation. Also, for the first time, it is shown herein that a particular region of EGFR is important to the binding interaction with HSP90. Based in part on these data, compounds that inhibit the binding interaction between EGFR and HSP90 have been made and have successfully demonstrated induction of selective EGFR degradation, cytotoxicity, and tumor regression.

Accordingly, the present disclosures provide compounds that inhibit a binding interaction between an EGFR and an HSP90. As further discussed herein, in some embodiments, the compound takes form of an antibody, or antibody analog, a peptide, or peptide analog.

Also provided by the present disclosures is a composition, e.g., a pharmaceutical composition, comprising a compound that inhibits a binding interaction between an EGFR and an HSP90. Kits comprising a compound that inhibits a binding interaction between an EGFR and an HSP90, optionally, in combination with a cancer therapeutic, also are provided herein.

Methods of using the compounds of the present disclosures are further provided herein. For example, a method of inhibiting a binding interaction between an EGFR and an HSP90 in a cell is provided. The method comprises contacting the cell with a compound that inhibits the binding interaction between an EGFR and an HSP90 in an amount effective to inhibit the binding interaction.

The present disclosures further provide methods of increasing degradation of an EGFR in a cell. The method comprises contacting the cell with a compound that inhibits the binding interaction between an EGFR and an HSP90 in an amount effective to increase the degradation.

The present disclosures furthermore provide methods of treating cancer in a subject. The method comprises administering to the subject a pharmaceutical composition comprising a compound that inhibits the binding interaction between an EGFR and an HSP90 in an amount effective to treat the cancer.

Further provided herein are methods of sensitizing tumors to radiation therapy, chemotherapy, or to both radiation therapy and chemotherapy, in a subject. The method comprises administering to the subject a pharmaceutical composition comprising a compound that inhibits the binding interaction between an EGFR and an HSP90 in an amount effective to sensitize the tumor to the therapy.

DETAILED DESCRIPTION

Inhibitors of EGFR-HSP90 Binding Interactions

Figure 1:
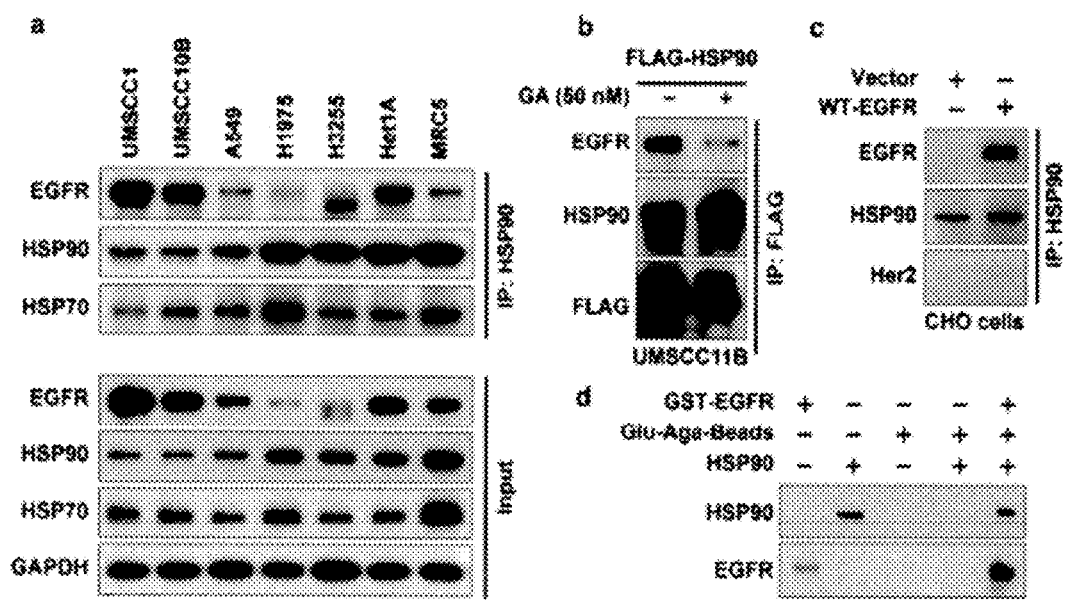
FIG. 1 demonstrates that EGFR is a client protein of HSP90. (a) Interaction between HSP90 and EGFR was assessed by immunoprecipitation. (b) This interaction was confirmed in UMSCC11B cells upon transfection with FLAG-HSP90 followed by FLAG immunoprecipitation and immunoblotting with EGFR antibody. Treatment with GA blocked interaction between EGFR and HSP90 (c) Specificity of the interaction was confirmed in CHO cells by transfection of full length EGFR followed by HSP90 immunoprecipitation and immunoblotting for EGFR and ErbB2. (d) A direct interaction between EGFR and HSP90 was confirmed by GST pull down assay.

Provided herein are compounds that inhibit a protein-protein binding interaction between an epidermal growth factor receptor (EGFR) and an heat shock protein 90 (HSP90). The compounds of the present disclosures may be considered as inhibitors of EGFR binding to an HSP90 and/or inhibitors of HSP90 binding to an EGFR. In some embodiments, the compounds are competitive binding inhibitors. In certain aspects, the compounds bind to the site of EGFR to which HSP90 binds. In certain aspects, the compounds bind to the site of HSP90 to which EGFR binds. In alternative embodiments, the compounds are non-competitive binding inhibitors. In certain aspects, the compounds inhibit the binding interaction between EGFR and HSP90, yet the compounds bind to a site of EGFR other than the site to which HSP90 binds or the compounds bind to a site of HSP90 other than the site to which EGFR binds.

The inhibition provided by the compounds of the present disclosures may not be a 100% or complete inhibition or abrogation of the binding interaction between the EGFR and HSP90. Rather, there are varying degrees of inhibition of which one of ordinary skill in the art recognizes as having a potential benefit or therapeutic effect. In this respect, the compounds of the present disclosures may inhibit the binding interaction between an EGFR and an HSP90 to any amount or level. In exemplary embodiments, the compound provides at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition) of the binding between EGFR and HSP90. In some embodiments, the compound completely abrogates the binding interaction between the EGFR and the HSP90, such that no EGFR-HSP90 binding complexes are detectable in a sample obtained from a subject, as measured by, for example, Western blotting, immunohistochemistry, and the like.

In some embodiments of the present disclosures, the compounds inhibit the binding interaction between a wild-type human EGFR and an HSP90. In some aspects, the compound inhibits the binding interaction between HSP90 and a wild-type human EGFR comprising an amino acid sequence of human EGFR isoform a (the amino acid sequence of which is accessible from the National Center for Biotechnology Information (NCBI) Protein Database as Accession No. NP_005219). In some aspects, the compound inhibits the binding interaction between HSP90 and a wild-type human EGFR comprising an amino acid sequence of human EGFR isoform b (the amino acid sequence of which is accessible from the NCBI Protein Database as Accession No. NP_958439.1). In some aspects, the compound inhibits the binding interaction between HSP90 and a wild-type human EGFR comprising an amino acid sequence of human EGFR isoform c (the amino acid sequence of which is accessible from the NCBI Protein Database as Accession No. NP_958440.1). In some aspects, the compound inhibits the binding interaction between HSP90 and a wild-type human EGFR comprising an amino acid sequence of human EGFR isoform d (the amino acid sequence of which is accessible from the NCBI Protein Database as Accession No. NP_958441). The amino acid sequences of each wild-type human EGFR isoform are provided herein as SEQ ID NOs: 1-4.

In other embodiments, the compounds inhibit the binding interaction between a mutant EGFR and an HSP90, wherein the mutant EGFR comprises an amino acid sequence which differs from any wild-type human EGFR amino acid sequence recognized in the art (e.g., the amino acid sequences of human EGFR isoforms a-d). In some aspects, the compound inhibits the binding interaction between HSP90 and the T790M EGFR mutant comprising the amino acid sequence of SEQ ID NO: 5 with the Thr at position 790 mutated to a Met. In other aspects, the compound inhibits the binding interaction between HSP90 and the L858R EGFR mutant comprising the amino acid sequence of SEQ ID NO: 34. In alternative aspects, the compound inhibits the binding interaction between HSP90 and the EGFRvIII mutant in which amino acids 6 to 273 are deleted and thus comprises the amino acid sequence of SEQ ID NO: 6.

In some embodiments, the compounds inhibit the binding interaction between a wild-type human HSP90 and an EGFR. In some aspects, the compound inhibits the binding interaction between an EGFR and an HSP90 comprising an amino acid sequence of SEQ ID NO: 7.

In exemplary aspects, the compound is an antibody, an antibody analog, a peptide, a peptide analog (e.g., peptoid, peptidomimetic), a nucleic acid molecule encoding any of the antibodies or peptides, or analogs thereof, or a small molecule compound (e.g., small molecule compound rationally designed based on any of the antibodies or peptides described herein).

Antibodies and Analogs Thereof.

In some embodiments of the present disclosures, the compound that inhibits a binding interaction between an EGFR and HSP90 comprises an antibody, or antigen binding fragment thereof. In some embodiments of the present disclosures, the compound that inhibits a binding interaction between an EGFR and HSP90 is provided as an antibody, or antigen binding fragment thereof. The antibody may be any type of immunoglobulin known in the art. In exemplary embodiments, the antibody is an antibody of isotype IgA, IgD, IgE, IgG, or IgM. Also, the antibody in some embodiments is a monoclonal antibody. In other embodiments, the antibody is a polyclonal antibody.

In some embodiments, the antibody is a naturally-occurring antibody, e.g., an antibody isolated and/or purified from a mammal, e.g., mouse, rabbit, goat, horse, chicken, hamster, human, and the like. In this regard, the antibody may be considered as a mammalian antibody, e.g., a mouse antibody, rabbit antibody, goat antibody, horse antibody, chicken antibody, hamster antibody, human antibody, and the like. Methods of producing naturally-occurring antibodies are known in the art, some of which are described further herein under the section entitled "Methods of Antibody Production."

In some embodiments, the antibody is a genetically-engineered antibody, e.g., a single chain antibody, a humanized antibody, a chimeric antibody, a CDR-grafted antibody, an antibody which includes portions of CDR sequences specific for EGFR or HSP90, a humaneered antibody, a bispecific antibody, a trispecific antibody, and the like. Genetic engineering techniques also provide the ability to make fully human antibodies in a non-human source.

In some aspects, the genetically-engineered antibody is a single chain antibody (SCA) specific for EGFR or HSP90. In particular aspects, the SCA binds to the site of EGFR to which HSP90 binds or the SCA binds to the site of HSP90 to which EGFR binds. In exemplary aspects, the SCA binds to an epitope as further described herein under the section entitled "Epitopes." Methods of making SCAs are known in the art. See, for example, Davis et al., *Nature Biotechnology* 9: 165-169 (1991).

In some aspects, the antibody is a chimeric antibody. The term "chimeric antibody" is used herein to refer to an antibody containing constant domains from one species and the variable domains from a second, or more generally, containing stretches of amino acid sequence from at least two species. In particular aspects, the chimeric antibody binds to the site of EGFR to which HSP90 binds or the chimeric antibody binds to the site of HSP90 to which EGFR binds. In exemplary aspects, the chimeric antibody binds to an epitope as further described herein under the section entitled "Epitopes."

In some aspects, the antibody is a humanized antibody. The term "humanized" when used in relation to antibodies refers to antibodies having at least CDR regions from a non-human source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence. In particular aspects, the humanized antibody binds to the site of EGFR to which HSP90 binds or the humanized antibody binds to the site of HSP90 to which EGFR binds. In exemplary aspects, the humanized antibody binds to an epitope as further described herein under the section entitled "Epitopes."

Use of the terms "chimeric or humanized" herein is not meant to be mutually exclusive, and rather, is meant to encompass chimeric antibodies, humanized antibodies, and chimeric antibodies that have been further humanized. Except where context otherwise indicates, statements about (properties of, uses of, testing of, and so on) chimeric antibodies of the present disclosures apply to humanized antibodies of the present disclosures, and statements about humanized antibodies of the present disclosures pertain also to chimeric antibodies. Likewise, except where context dictates, such statements also should be understood to be applicable to antibodies and antigen binding fragments of such antibodies of the present disclosures.

In some aspects, the antibody is a CDR-grafted antibody specific for EGFR or HSP90. In particular aspects, the CDR-grafted antibody binds to the site of EGFR to which HSP90 binds or the CDR-grafted antibody binds to the site of HSP90 to which EGFR binds. In exemplary aspects, the CDR-grafted antibody binds to an epitope as further described herein under the section entitled "Epitopes." Methods of making CDR-grafted antibodies are known in the art. See, for example, Lo, Benny, *Antibody Engineering: Methods and Protocols*, Volume 248 (2004), which is incorporated by reference in its entirety.

In some aspects, the antibody is a bispecific or trispecific antibody specific for EGFR or HSP90. In particular aspects, the bispecific or trispecific antibody binds to the site of EGFR to which HSP90 binds or the bispecific or trispecific antibody binds to the site of HSP90 to which EGFR binds. In exemplary aspects, the bispecific or trispecific antibody binds to an epitope as further described herein under the section entitled "Epitopes." Methods of making bispecific or trispecific antibodies are known in the art. See, for example, Marvin and Zhu, *Acta Pharmacologica Sinica* 26: 649-658 (2005) and U.S. Pat. No. 6,551,592.

In some aspects, the antibody is a Humaneered™ antibody. Humaneering technology is a proprietary method of KaloBios Pharmaceuticals, Inc. (San Francisco, Calif.) for converting non human antibodies into engineered human antibodies. Humaneered™ antibodies are high affinity, and highly similar to human germline antibody sequences.

In some embodiments, the antibody has a level of affinity or avidity for the EGFR which is sufficient to prevent HSP90 from binding to the EGFR. In some embodiments, the antibody has a level of affinity or avidity for the HSP90 which is sufficient to prevent EGFR from binding HSP90. Therefore in some embodiments, the affinity constant, $K_a$, (which is the inverterd dissocation constant, $K_d$) of the antibody of the present disclosures for the EGFR is greater than the $K_a$ of HSP90 for the EGFR. Alternatively, in some embodiments, the $K_a$ of the antibody of the present disclosures for the HSP90 is greater than that of EGFR for HSP90. Binding constants, including dissociation constants, may be determined by methods known in the art, including, for example, methods which utilize the principles of surface plasmon resonance, e.g., methods utilizing a Biacore™ system.

In some embodiments, the antibody is in monomeric form, while in other embodiments, the antibody is conjugated to one or more antibodies (e.g., each of which recognize the same epitope of the first antibody). Accordingly, in some aspects, the antibody is in polymeric, oligomeric, or multimeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

Antigen Binding Fragments

In some aspects of the present disclosures, the compound which inhibits a binding interaction between an EGFR and HSP90 is an antigen binding fragment of an antibody. The antigen binding fragment (also referred to herein as "antigen binding portion") may be an antigen binding fragment of any of the antibodies described herein. The antigen binding fragment can be any part of an antibody that has at least one antigen binding site, including, but not limited to, Fab, F(ab')$_2$, dsFv, sFv, diabodies, triabodies, bis-scFvs, fragments expressed by a Fab expression library, domain antibodies, VhH domains, V-NAR domains, VH domains, VL domains, and the like. Antibody fragments of the invention, however, are not limited to these exemplary types of antibody fragments.

A domain antibody comprises a functional binding unit of an antibody, and can correspond to the variable regions of either the heavy ($V_H$) or light ($V_L$) chains of antibodies. A domain antibody can have a molecular weight of approximately 13 kDa, or approximately one-tenth of a full antibody. Domain antibodies may be derived from full antibodies such as those described herein. The antigen binding fragments in some embodiments are monomeric or polymeric, bispecific or trispecific, bivalent or trivalent.

Antibody fragments that contain the antigen binding, or idiotype, of the antibody molecule may be generated by techniques known in the art. For example, such fragments include, but are not limited to, the F(ab')$_2$ fragment which may be produced by pepsin digestion of the antibody molecule; the Fab' fragments which may be generated by reducing the disulfide bridges of the F(ab')$_2$ fragment, and the two Fab' fragments which may be generated by treating the antibody molecule with papain and a reducing agent.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)).

Recombinant antibody fragments, e.g., scFvs, can also be engineered to assemble into stable multimeric oligomers of high binding avidity and specificity to different target antigens. Such diabodies (dimers), triabodies (trimers) or tetrabodies (tetramers) are well known in the art, see e.g., Kortt et al., *Biomol Eng.* 2001 18:95-108, (2001) and Todorovska et al., *J Immunol Methods.* 248:47-66, (2001).

Bispecific antibodies (bscAb) are molecules comprising two single-chain Fv fragments joined via a glycine-serine linker using recombinant methods. The V light-chain ($V_L$) and V heavy-chain ($V_H$) domains of two antibodies of interest in exemplary embodiments are isolated using standard PCR methods. The $V_L$ and $V_H$ cDNA's obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present invention. Exemplary bispecific antibodies are taught in U.S. Patent Application Publication No. 2005-0282233A1 and International Patent Application Publication No. WO 2005/087812, both applications of which are incorporated herein by reference in their entirety.

Methods of Antibody or Antigen Binding Fragment Production

Suitable methods of making antibodies are known in the art. For instance, standard hybridoma methods are described in, e.g., Harlow and Lane (eds.), Antibodies: A Laboratory Manual, CSH Press (1988), and CA. Janeway et al. (eds.), Immunobiology, 5$^{th}$ Ed., Garland Publishing, New York, N.Y. (2001)).

Briefly, a polyclonal antibody is prepared by immunizing an animal with an immunogen comprising a polypeptide of the present invention and collecting antisera from that immunized animal. A wide range of animal species can be used for the production of antisera. In some aspects, an animal used for production of anti-antisera is a non-human animal including rabbits, mice, rats, hamsters, goat, sheep, pigs or horses. Because of the relatively large blood volume of rabbits, a rabbit is a preferred choice for production of polyclonal antibodies. In an exemplary method for generating a polyclonal antisera immunoreactive with the chosen EGFR epitope, 50 µg of EGFR antigen is emulsified in Freund's Complete Adjuvant for immunization of rabbits. At intervals of, for example, 21 days, 50 µg of epitope are emulsified in Freund's Incomplete Adjuvant for boosts. Polyclonal antisera may be obtained, after allowing time for antibody generation, simply by bleeding the animal and preparing serum samples from the whole blood.

Monoclonal antibodies for use in the invention may be prepared using any technique which provides for the production of antibody molecules by continuous cell lines in culture. These include but are not limited to the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985).

Briefly, in exemplary embodiments, to generate monoclonal antibodies, a mouse is injected periodically with recombinant EGFR against which the antibody is to be raised (e.g., 10-20 µg emulsified in Freund's Complete Adjuvant). The mouse is given a final pre-fusion boost of an EGFR polypeptide in PBS, and four days later the mouse is sacrificed and its spleen removed. The spleen is placed in 10 ml serum-free RPMI 1640, and a single cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 µg/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Splenocytes taken from three naive Balb/c mice are prepared in a similar manner and used as a control. NS-1 myeloma cells, kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice.

Spleen cells ($1 \times 10^8$) are combined with $2.0 \times 10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and $1.5 \times 10^6$ splenocytes/ml and plated into 10 Corning flat-bottom 96-well tissue culture plates (Corning, Corning N.Y.).

On days 2, 4, and 6, after the fusion, 100 µl of medium is removed from the wells of the fusion plates and replaced with fresh medium. On day 8, the fusion is screened by ELISA, testing for the presence of mouse IgG binding to EGFR as follows. Immulon 4 plates (Dynatech, Cambridge, Mass.) are coated for 2 hours at 37° C. with 100 ng/well of EGFR diluted in 25 mM Tris, pH 7.5. The coating solution is aspirated and 200 µl/well of blocking solution (0.5% fish skin gelatin (Sigma) diluted in CMF-PBS) is added and incubated for 30 min. at 37° C. Plates are washed three times with PBS with 0.05% Tween 20 (PBST) and 50 µl culture supernatant is added. After incubation at 37° C. for 30 minutes, and washing as above, 50 µl of horseradish peroxidase conjugated goat anti-mouse IgG(fc) (Jackson ImmunoResearch, West Grove, Pa.) diluted 1:3500 in PBST is added. Plates are incubated as above, washed four times with PBST, and 100 µl substrate, consisting of 1 mg/ml o-phenylene diamine (Sigma) and 0.1 µl/ml 30% $H_2O_2$ in 100 mM Citrate, pH 4.5, are added. The color reaction is stopped after 5 minutes with the addition of 50 µl of 15% $H_2SO_4$. $A_{490}$ is read on a plate reader (Dynatech).

Selected fusion wells are cloned twice by dilution into 96-well plates and visual scoring of the number of colonies/well after 5 days. The monoclonal antibodies produced by hybridomas are isotyped using the Isostrip system (Boehringer Mannheim, Indianapolis, Ind.).

When the hybridoma technique is employed, myeloma cell lines may be used. Such cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/15XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions. It should be noted that the hybridomas and cell lines produced by such techniques for producing the monoclonal antibodies are contemplated to be novel compositions of the present disclosures.

Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Antibodies may also be produced by inducing in vivo production in the lymphocyte population or by screening recombinant immunoglobulin libraries or panels of highly specific binding reagents as disclosed in Orlandi et al (Proc Natl Acad Sci 86: 3833-3837; 1989), and Winter G and Milstein C (Nature 349: 293-299, 1991).

Phage display furthermore can be used to generate the antibody of the present disclosures. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, $3^{rd}$ Edition, Cold Spring Harbor Laboratory Press, New York (2001)), Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150). Related methods also are described in U.S. Pat. No. 5,403,484; U.S. Pat. No. 5,571,698; U.S. Pat. No. 5,837,500; U.S. Pat. No. 5,702,892. The techniques described in U.S. Pat. No. 5,780,279; U.S. Pat. No. 5,821,047; U.S. Pat. No. 5,824,520; U.S. Pat. No. 5,855,885; U.S. Pat. No. 5,858,657; U.S. Pat. No. 5,871,907; U.S. Pat. No. 5,969,108; U.S. Pat. No. 6,057,098; U.S. Pat. No. 6,225,447, Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol, 235, 959-973 (1994).

Techniques developed for the production of "chimeric antibodies", the splicing of mouse antibody genes to human antibody genes to obtain a molecule with appropriate antigen specificity and biological activity, can be used (Morrison et al., Proc Natl Acad Sci 81: 6851-6855, 1984; Neuberger et al., Nature 312: 604-608, 1984; Takeda et al., Nature 314: 452-454; 1985). Alternatively, techniques described for the production of single chain antibodies (U.S. Pat. No. 4,946,778) can be adapted to produce EGFR- or HSP90-specific single chain antibodies.

A preferred chimeric or humanized antibody has a human constant region, while the variable region, or at least a CDR, of the antibody is derived from a non-human species. Methods for humanizing non-human antibodies are well known in the art. (see U.S. Pat. Nos. 5,585,089, and 5,693,762). Generally, a humanized antibody has one or more amino acid residues introduced into its framework region from a source which is non-human. Humanization can be performed, for example, using methods described in Jones et al. (*Nature* 321: 522-525, 1986), Riechmann et al., (*Nature,* 332: 323-327, 1988) and Verhoeyen et al. (*Science* 239:1534-1536, 1988), by substituting at least a portion of a rodent complementarity-determining region (CDRs) for the corresponding regions of a human antibody. Numerous techniques for preparing engineered antibodies are described, e.g., in Owens and Young, *J. Immunol. Meth.,* 168:149-165 (1994). Further changes can then be introduced into the antibody framework to modulate affinity or immunogenicity.

Likewise, using techniques known in the art to isolate CDRs, compositions comprising CDRs are generated. Complementarity determining regions are characterized by six polypeptide loops, three loops for each of the heavy or light chain variable regions. The amino acid position in a CDR is defined by Kabat et al., "Sequences of Proteins of Immunological Interest," U.S. Department of Health and Human Services, (1983), which is incorporated herein by reference. For example, hypervariable regions of human antibodies are roughly defined to be found at residues 28 to 35, from 49-59 and from residues 92-103 of the heavy and light chain variable regions (Janeway and Travers, *Immunobiology,* $2^{nd}$ Edition, Garland Publishing, New York, (1996)). The murine CDR also are found at approximately these amino acid residues. It is understood in the art that CDR regions may be found within several amino acids of these approximated residues set forth above. An immunoglobulin variable region also consists of four "framework" regions surrounding the CDRs (FR1-4). The sequences of the framework regions of different light or heavy chains are highly conserved within a species, and are also conserved between human and murine sequences.

Compositions comprising one, two, and/or three CDRs of a heavy chain variable region or a light chain variable region of a monoclonal antibody are generated. Techniques for cloning and expressing nucleotide and polypeptide sequences are well-established in the art (see e.g. Sambrook et al., *Molecular Cloning: A Laboratory Manual,* $2^{nd}$ Edition, Cold Spring Harbor, N.Y. (1989)). The amplified CDR sequences are ligated into an appropriate plasmid. The plasmid comprising one, two, three, four, five and/or six cloned CDRs optionally contains additional polypeptide encoding regions linked to the CDR.

Framework regions (FR) of a murine antibody are humanized by substituting compatible human framework regions chosen from a large database of human antibody variable sequences, including over twelve hundred human VH sequences and over one thousand VL sequences. The database of antibody sequences used for comparison is downloaded from Andrew C. R. Martin's KabatMan web page (rubic.rdg.ac.uk/abs/). The Kabat method for identifying CDR provides a means for delineating the approximate CDR and framework regions from any human antibody and comparing the sequence of a murine antibody for similarity to determine the CDRs and FRs. Best matched human VH and VL sequences are chosen on the basis of high overall framework matching, similar CDR length, and minimal mismatching of canonical and VH/VL contact residues. Human framework regions most similar to the murine sequence are inserted between the murine CDR. Alternatively, the murine framework region may be modified by making amino acid substitutions of all or part of the native framework region that more closely resemble a framework region of a human antibody.

Additionally, another useful technique for generating antibodies for use in the present invention may be one which uses a rational design type approach. The goal of rational design is to produce structural analogs of biologically active polypeptides or compounds with which they interact (agonists, antagonists, inhibitors, peptidomimetics, binding partners, etc.). In one approach, one would generate a three-dimensional structure for the antibodies or an epitope binding fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to solve the crystal structure of the specific antibodies. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate additional antibodies from banks of chemically- or biologically-produced peptides.

Chemically constructed bispecific antibodies may be prepared by chemically cross-linking heterologous Fab or F(ab')$_2$ fragments by means of chemicals such as heterobifunctional reagent succinimidyl-3-(2-pyridyldithiol)-propionate (SPDP, Pierce Chemicals, Rockford, Ill.). The Fab and F(ab')$_2$ fragments can be obtained from intact antibody by digesting it with papain or pepsin, respectively (Karpovsky et al., J. Exp. Med. 160:1686-701, 1984; Titus et al., J. Immunol., 138:4018-22, 1987).

Methods of testing antibodies for the ability to bind to the epitope of the EGFR regardless of how the antibodies are produced are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Aptamers

In some embodiments, the compound that inhibits a binding interaction between EGFR and HSP90 is an analog of an antibody. In some aspects, the compound is an aptamer. Recent advances in the field of combinatorial sciences have identified short polymer sequences (e.g., oligonucleic acid or peptide molecules) with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds and phage display has been utilized to discover new peptide sequences with very favorable binding properties. Based on the success of these molecular evolution techniques, it is certain that molecules can be created which bind to any target molecule. A loop structure is often involved with providing the desired binding attributes as in the case of: aptamers which often utilize hairpin loops created from short regions without complimentary base pairing, naturally derived antibodies that utilize combinatorial arrangement of looped hyper-variable regions and new phage display libraries utilizing cyclic peptides that have shown improved results when compared to linear peptide phage display results. Thus, sufficient evidence has been generated to suggest that high affinity ligands can be created and identified by combinatorial molecular evolution techniques. For the present disclosures, molecular evolution techniques can be used to isolate compounds specific for the EGFRs or HSP90s described herein that inhibit the binding interaction between EGFR and HSP90. For more on aptamers, see, generally, Gold, L., Singer, B., He, Y. Y., Brody. E., "Aptamers As Therapeutic And Diagnostic Agents," J. Biotechnol. 74:5-13 (2000). Relevant techniques for generating aptamers may be found in U.S. Pat. No. 6,699,843, which is incorporated by reference in its entirety.

Epitopes

By "epitope" as used herein is meant the region of or within the EGFR or HSP90 which is bound by the compound, e.g., the antibody, the antigen binding fragment, the aptamer. In some embodiments, the epitope is a linear epitope. By "linear epitope" as used herein refers to the region of or within the EGFR or HSP90 which is bound by the compound, which region is composed of contiguous amino acids of the amino acid sequence of the EGFR or HSP90. The amino acids of a linear epitope are located in close proximity to each other in the primary structure of the antigen and the secondary and/or tertiary structure(s) of the antigen. For example, when the antigen, e.g., EGFR or HSP90, is in its properly folded state (e.g., its native conformation), the contiguous amino acids of the linear epitope are located in close proximity to one another.

In other aspects, the epitope of the binding construct is a conformational epitope. By "conformational epitope" is meant an epitope which is composed of amino acids which are located in close proximity to one another only when the EGFR or HSP90 is in its properly folded state, but are not contiguous amino acids of the amino acid sequence of the EGFR or HSP90.

In some embodiments of the present disclosures, the compound that inhibits a binding interaction between an EGFR and HSP90 binds to an epitope of an EGFR. In some aspects, the epitope to which the compound binds is within the kinase domain of EGFR (e.g., amino acids 688 to 955 of SEQ ID NO: 1). In some aspects, the compound that inhibits a binding interaction between an EGFR and HSP90 binds to an epitope within amino acids 761-781 of the EGFR sequence (SEQ ID NO: 1). In further aspects, the compound that inhibits a binding interaction between an EGFR and HSP90 binds to an epitope within amino acids 768-773 of the SEQ ID NO: 1, amino acids 768-775 of SEQ ID NO: 1, or amino acids 776-781 of SEQ ID NO: 1.

In some embodiments, the compound that inhibits a binding interaction between an EGFR and HSP90 binds to an epitope comprising the amino acid sequence DNPH (SEQ ID NO: 13) or RLLGIC (SEQ ID NO: 14). In specific aspects, the compound binds to an epitope comprising the amino acid sequence SVDNPH (SEQ ID NO: 15), SVDNPHV (SEQ ID NO: 16), or SVDNPHVX (SEQ ID NO: 17), wherein X is Cys, Ser, Ala, Gly, Val.

In yet other embodiments, the compound that inhibits the binding interaction between an EGFR and HSP90 binds to an epitope comprising the amino acid sequence of any of the peptides or peptide analogs described herein, which peptides or peptide analogs are described herein as a compound that inhibits the binding interaction between an EGFR and HSP90.

Peptides

In some embodiments of the present disclosures, the compound that inhibits a binding interaction between an EGFR and HSP90 is a peptide comprising at least four amino acids connected via peptide bonds. In some aspects, the peptide is about 4 to about 50 amino acids in length. In some aspects, the compound is about 6 to about 25 amino acids in length. In some aspects, the compound is about 8 to about 12 amino acids in length. In some embodiments, the peptide is an 8-mer.

Fragments of EGFR

In some embodiments, the peptide that inhibits a binding interaction between an EGFR and HSP90 is a fragment of a human wild-type EGFR, e.g., any of those disclosed herein. In some aspects, the compound is a fragment of wild-type human EGFR isoform a which is provided herein as SEQ ID NO: 1. In specific aspects, the compound comprises 4 to 10 consecutive amino acids of amino acids 688 to 955 of SEQ ID NO: 1, which portion of SEQ ID NO: 1 represents the kinase domain of the EGFR. In further aspects, the compound comprises 4 to 10 consecutive amino acids from amino acids 761-781 of the SEQ ID NO: 1. In yet further aspects, the compound comprises the amino acid sequence DNPH (SEQ ID NO: 13) or RLLGIC (SEQ ID NO: 14). In some embodiments, the compound comprises the amino acid sequence SVDNPH (SEQ ID NO: 15), SVDNPHV (SEQ ID NO: 16), or SVDNPHVC (SEQ ID NO: 18).

Derivatives

In some embodiments, the peptide that inhibits a binding interaction between an EGFR and HSP90 comprises an amino acid sequence which is based on the amino acid sequence of a human wild-type EGFR, or a fragment thereof, but differs at one or more (e.g., two, three, four, five, six, seven, eight, nine, ten, or more) amino acid positions, when aligned with the human wild-type EGFR sequence, or fragment thereof.

In some embodiments, the peptide that inhibits a binding interaction between an EGFR and HSP90 comprises an amino acid sequence which has at least 25% sequence identity to the amino acid sequence of a human wild-type EGFR, e.g., SEQ ID NO: 1, or a fragment thereof (e.g., a fragment of about 4 to about 10 contiguous amino acids of SEQ ID NO: 8 or 9). In some embodiments, the compound comprises an amino acid sequence which is at least 30%, at least 40%, at least 50%, at least 60%, at least 70%, at least 75%, at least 80%, at least 85%, at least 90%, at least 95%, or has greater than 95% sequence identity to SEQ ID NO: 1, or a fragment thereof (e.g., a fragment of about 4 to about 10 contiguous amino acids of SEQ ID NO: 8 or 9).

In exemplary embodiments, the compound comprises an amino acid sequence which is based on the EGFR fragment SVDNPH (SEQ ID NO: 15). In some aspects, the compound comprises SVDNPHVX (SEQ ID NO: 17), wherein X is any amino acid. In particular aspects, X is the native residue which follows this sequence in the wild-type EGFR amino acid sequence (namely, Cys). In other aspects, X is a non-native residue or is an amino acid other than Cys. In particular aspects, X is an amino acid which is similar in size to Cys, but lacks the sulfur atom. In exemplary aspects, X is Ser, Gly, Val, or Ala.

In other exemplary embodiments, the compound comprises an amino acid sequence of SVDNPH (SEQ ID NO: 15) with up to two amino acid substitutions. In some aspects, the amino acid substitution(s) occur(s) at one or two of the positions 1, 2, 3, 4, 5, and 6. In particular aspects, the amino acid substitution(s) occur(s) at one or two of the positions 1, 3, and 5 of SVDNPH (SEQ ID NO: 15). In some aspects, the compound comprises the amino acid sequence XVXNXH (SEQ ID NO: 19), XVXNPH (SEQ ID NO: 20), XVDNPH (SEQ ID NO: 21), SVXNXH (SEQ ID NO: 22), SVXNPH (SEQ ID NO: 23), or SVDNXH (SEQ ID NO: 24), wherein each X represents any amino acid. In some aspects, the X is the native residue of the wild-type EGFR amino acid sequence. In other aspects, the X is a non-native residue of the wild-type EGFR amino acid sequence. In exemplary aspects, the compound comprises S, D, I, or A at position 1 of SEQ ID NO: 19. In some aspects, the compound comprises D, A, or G at position 3 of SEQ ID NO: 19. In some aspects, the compound comprises P or G at position 5 of SEQ ID NO: 19. In some aspects, the compound comprises an amino acid sequence selected from the group consisting of: AVDNPH (SEQ ID NO: 25), DVDNPH (SEQ ID NO: 26), IVDNPH (SEQ ID NO: 27), SVGNPH (SEQ ID NO: 28), SVDNGH (SEQ ID NO: 29), and SVAAPH (SEQ ID NO: 30).

Cyclized or Bridged Compounds

In some embodiments, the peptide that inhibits a binding interaction between an EGFR and HSP90 is a cyclized peptide or a peptide that comprises an intramolecular bridge which links the side chains of two amino acids of the compound. In some embodiments, the intramolecular bridge is a bridge which connects two parts of the peptide via noncovalent bonds, including, for example, van der Waals interactions, hydrogen bonds, ionic bonds, hydrophobic interactions, dipole-dipole interactions, and the like. In this regard, the peptide in certain aspects comprises a non-covalent intramolecular bridge. In some embodiments, the intramolecular bridge is a bridge which connects two parts of the peptide via covalent bonds. In this regard, the peptide in certain aspects comprises a covalent intramolecular bridge.

Non-Covalent Intramolecular Bridges

In some embodiments, the non-covalent intramolecular bridge is a salt bridge. In exemplary embodiments, the peptide is bridged between two amino acids: one of the amino acids of the peptide is an amino acid of Formula I and the other amino acid of the peptide.

In some embodiments, the non-covalent intramolecular bridge is a hydrophobic bridge. In accordance with one embodiment, the compound is stabilized through the incorporation of hydrophobic amino acids at positions j and j+5 or i and i+4. For instance, i can be Tyr and i+4 can be either Val or Leu; i can be Phe and i+4 can be Met; or i can be Phe and i+4 can be Ile. It should be understood that, for purposes herein, the above amino acid pairings can be reversed, such that the indicated amino acid at position i could alternatively be located at i+4, while the i+4 amino acid can be located at the i position. It should also be understood that suitable amino acid pairings can be formed for j and j+5.

Covalent Intramolecular Bridge

In some embodiments, the covalent intramolecular bridge is a lactam ring or lactam bridge. The size of the lactam ring can vary depending on the length of the amino acid side chains, and in one embodiment the lactam is formed by linking the side chains of an ornithine to a aspartic acid side chain. Lactam bridges and methods of making the same are known in the art. See, for example, Houston, Jr., et al., *J Peptide Sci* 1: 274-282 (2004). In some embodiments, the compound comprises a modified sequence of a fragment of SEQ ID NO: 1 and a lactam bridge between i and i+4, wherein i is as defined herein above.

In some embodiments, the covalent intramolecular bridge is a lactone. Suitable methods of making a lactone bridge are known in the art. See, for example, Sheehan et al., *J Am Chem Soc* 95: 875-879 (1973).

In some aspects, olefin metathesis is used to cross-link the compound using an all-hydrocarbon cross-linking system. The compound in this instance comprises α-methylated amino acids bearing olefinic side chains of varying length and configured with either R or S stereochemistry at the j and j+5 or i and i+4 positions. In some embodiments, the olefinic side comprises $(CH_2)n$, wherein n is any integer between 1 to 6. In some embodiments, n is 3 for a cross-link length of 8 atoms. In some embodiments, n is 2 for a cross-link length of 6 atoms. Suitable methods of forming such intramolecular bridges are described in the art. See, for example, Schafmeister et al., *J. Am. Chem. Soc.* 122: 5891-5892 (2000) and Walensky et al., *Science* 305: 1466-1470 (2004). In alternative embodiments, the compound comprises O-allyl Ser residues, which are bridged together via ruthenium-catalyzed ring closing metathesis. Such procedures of cross-linking are described in, for example, Blackwell et al., *Angew. Chem., Int. Ed.* 37: 3281-3284 (1998).

In specific aspects, use of the unnatural thio-dialanine amino acid, lanthionine, which has been widely adopted as a peptidomimetic of cystine, is used to cross-link one turn of the alpha helix. Suitable methods of lanthionine-based cyclization are known in the art. See, for instance, Matteucci et al., *Tetrahedron Letters* 45: 1399-1401 (2004); Mayer et al., *J. Peptide Res.* 51: 432-436 (1998); Polinsky et al., *J. Med. Chem.* 35: 4185-4194 (1992); Osapay et al., *J. Med. Chem.* 40: 2241-2251 (1997); Fukase et al., *Bull. Chem. Soc. Jpn.* 65: 2227-2240 (1992); Harpp et al., *J. Org. Chem.* 36: 73-80 (1971); Goodman and Shao, *Pure Appl. Chem.* 68: 1303-1308 (1996); and Osapay and Goodman, *J. Chem. Soc. Chem. Commun.* 1599-1600 (1993).

In some embodiments, α, ω-diaminoalkane tethers, e.g., 1,4-diaminopropane and 1,5-diaminopentane) between two Glu residues at positions i and i+7 are used to stabilize the compound. Such tethers lead to the formation of a bridge 9-atoms or more in length, depending on the length of the diaminoalkane tether. Suitable methods of producing peptides cross-linked with such tethers are described in the art. See, for example, Phelan et al., *J. Am. Chem. Soc.* 119: 455-460 (1997).

In yet other embodiments, a disulfide bridge is used to cross-link compound. Alternatively, a modified disulfide bridge in which one or both sulfur atoms are replaced by a methylene group resulting in an isosteric macrocyclization is used to stabilize the alpha helix of the compound. Suitable methods of modifying peptides with disulfide bridges or sulfur-based cyclization are described in, for example, Jackson et al., *J. Am. Chem. Soc.* 113: 9391-9392 (1991) and Rudinger and Jost, *Experientia* 20: 570-571 (1964).

In yet other embodiments, the compound is stabilized via the binding of metal atom by two His residues or a His and Cys pair positioned at j and j+3, or i and i+4. The metal atom can be, for example, Ru(III), Cu(II), Zn(II), or Cd(II). Such methods of metal binding-based alpha helix stabilization are known in the art. See, for example, Andrews and Tabor, *Tetrahedron* 55: 11711-11743 (1999); Ghadiri et al., *J. Am. Chem. Soc.* 112: 1630-1632 (1990); and Ghadiri et al., *J. Am. Chem. Soc.* 119: 9063-9064 (1997).

The compound may alternatively be stabilized through other means of peptide cyclizing, which means are reviewed in Davies, *J. Peptide. Sci.* 9: 471-501 (2003). The compound may be stabilized via the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g., suberic acid (octanedioic acid), etc. can introduce a link between two functional groups of an amino acid side chain, such as a free amino, hydroxyl, thiol group, and combinations thereof.

Spacing/Size of Bridge

In some embodiments, the intramolecular bridge (e.g., non-covalent intramolecular bridge, covalent intramolecular bridge) is formed between two amino acids that are 3 amino acids apart, e.g., amino acids at positions i and i+4. In specific embodiments, wherein the amino acids at positions i and i+4 are joined by an intramolecular bridge, the size of the linker is about 8 atoms, or about 7-9 atoms.

In other embodiments, the intramolecular bridge is formed between two amino acids that are four amino acids apart, e.g., amino acids at positions j and j+5. In specific embodiments, wherein amino acids at positions j and j+5 are joined by an intramolecular bridge, the size of the linker is about 6 atoms, or about 5 to 7 atoms.

In yet other embodiments, the intramolecular bridge is formed between two amino acids that are five amino acids apart, e.g., amino acids at positions k and k+6.

Amino Acids Involved in Intramolecular Bridges

Examples of amino acid pairings that are capable of bonding (covalently or non-covalently) to form a six-atom linking bridge include Orn and Asp, Glu and an amino acid of Formula I, wherein n is 2, and homoglutamic acid and an amino acid of Formula I, wherein n is 1, wherein Formula I is:

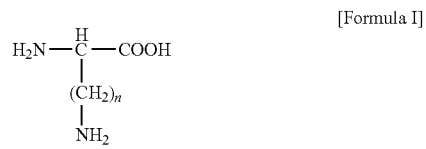

wherein n = 1 to 4

Examples of amino acid pairings that are capable of bonding to form a seven-atom linking bridge include Orn-Glu (lactam ring); Lys-Asp (lactam); or Homoser-Homoglu (lactone). Examples of amino acid pairings that may form an eight-atom linker include Lys-Glu (lactam); Homolys-Asp (lactam); Orn-Homoglu (lactam); 4-aminoPhe-Asp (lactam); or Tyr-Asp (lactone). Examples of amino acid pairings that may form a nine-atom linker include Homolys-Glu (lactam); Lys-Homoglu (lactam); 4-aminoPhe-Glu (lactam); or Tyr-Glu (lactone). Any of the side chains on these amino acids may additionally be substituted with additional chemical groups. One of ordinary skill in the art can envision alternative pairings or alternative amino acid analogs, including chemically modified derivatives, that would create a stabilizing structure of similar size and desired effect. For example, a homocysteine-homocysteine disulfide bridge is 6 atoms in length and may be further modified to provide the desired effect.

Even without covalent linkage, the amino acid pairings described above (or similar pairings that one of ordinary skill in the art can envision) may also provide added stability to the compound through non-covalent bonds, for example, through formation of salt bridges or hydrogen-bonding interactions. Accordingly, salt bridges may be formed between: Orn and Glu; Lys and Asp; Homo-serine and Homo-glutamate; Lys and Glu; Asp and Arg; Homo-Lys and Asp; Orn and Homo-Glutamate; 4-aminoPhe and Asp; Tyr and Asp; Homo-Lys and Glu; Lys and Homo-Glu; 4-aminoPhe and Glu; or Tyr and Glu. In some embodiments, the compound comprises a salt bridge between any of the following pairs of amino acids: Orn and Glu; Lys and Asp; Lys and Glu; Asp and Arg; Homo-Lys and Asp; Orn and Homo-Glutamate; Homo-Lys and Glu; and Lys and Homo-Glu. Salt bridges may be formed between other pairs of oppositely charged side chains. See, e.g., Kallenbach et al., *Role of the Peptide Bond in Protein Structure and Folding*, in The Amide Linkage: Structural Significance in Chemistry, Biochemistry, and Materials Science, John Wiley & Sons, Inc. (2000).

Exemplary Cyclized or Bridged Compounds

In some aspects, the compound that inhibits a binding interaction between an EGFR and HSP90 comprises an intramolecular bridge which links two amino acids separated by 3, 4, or 5 amino acids in the amino acid sequence of the compound. In some aspects, the intramolecular bridge is a disulfide bridge, a dithioether bridge, a carba analog bridge, or a lactam bridge. In specific aspects, when the intramolecular bridge is a dithioether, the dithioether comprises the structure —S(CH$_2$)$_n$S—, wherein n is 1, 2, 3, 4, or 5. In specific aspects, when the intramolecular bridge is carba analog bridge, the carba analog bridge comprises a C3 to C10 alkyl chain.

In some aspects, when the intramolecular bridge is a lactam bridge, the lactam is formed between the side chains of an amino acid of Formula I and an amino acid of Formula II, wherein Formula I is:

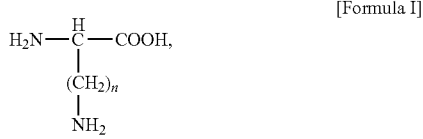

[Formula I]

wherein n = 1 to 4 and Formula II is:

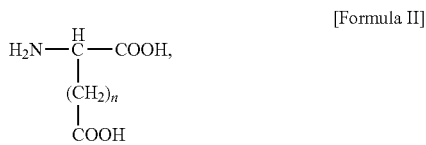

[Formula II]

wherein n = 1 to 4.

In specific embodiments, the amino acid of Formula I is Lys or Orn. In specific embodiments, the amino acid of Formula II is Asp or Glu.

In some embodiments, the compound comprises the amino acid sequence XDNPHX (SEQ ID NO: 32), wherein the side chains of the amino acids at positions 1 and 6 are covalently linked by the intramolecular bridge. In some aspects, each of the amino acids at positions 1 and 6 is Cys. In specific aspects, the side chains of the amino acids at positions 1 and 6 are linked by a disulfide bond or a dithioether. In alternative aspects, the intramolecular bridge is a lactam and one of the amino acids at positions 1 and 6 is an amino acid of Formula I and the other amino acid is an amino acid of Formula II. In some aspects, the compound comprises the amino acid sequence SXDNPHXX (SEQ ID NO: 33), wherein the X at position 8 is C, S, or A.

Additional Peptide Modifications

In alternative or additional embodiments of the present disclosures, the peptide is glycosylated, amidated, carboxylated, phosphorylated, esterified, N-acylated, acetylated, or converted into an acid addition salt and/or optionally dimerized or polymerized, or conjugated, as further described herein.

In some aspects, the first amino acid of the peptide is acetylated at the N-terminus in which the N-terminal alpha —NH$_2$ group of an unmodified peptide is converted into —COCH$_3$. In alternative or additional aspects, the last amino acid of the peptide is amidated at the C-terminus in which the C-terminal —COOH group of an unmodified peptide is converted into an —NH$_2$.

Peptide Analogs

In some embodiments, the compound is a peptide analog having a structure based on one of the peptides disclosed herein (the "parent peptide") but differs from the parent peptide in one or more respects. Accordingly, as appreciated by one of ordinary skill in the art the teachings of the parent peptides provided herein may also be applicable the peptide analogs.

In some aspects, the peptide analog comprises the structure of a parent peptide, except that the peptide analog comprises one or more non-peptide bonds in place of peptide bond(s). In exemplary aspects, the peptide analog comprises in place of a peptide bond, an ester bond, an ether bond, a thioether bond, an amide bond, and the like. In some aspects, the peptide analog is a depsipeptide comprising an ester linkage in place of a peptide bond.

In some aspects, the peptide analog comprises the structure of a parent peptide described herein, except that the peptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

In some aspects, the peptide analog comprises one or more synthetic amino acids, e.g., an amino acid non-native to a mammal. Synthetic amino acids include β-alanine (β-Ala), N-α-methyl-alanine (Me-Ala), aminobutyric acid (Abu), γ-aminobutyric acid (γ-Abu), aminohexanoic acid (ϵ-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met (O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe (4-Cl)), 4-fluorophenylalanine (Phe(4-F)), 4-nitrophenylalanine (Phe(4-NO$_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,- tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

In some embodiments, the peptide analog comprises one or more non-conservative amino acid substitutions and the peptide analog still functions to a similar extent, the same extent, or an improved extent as the parent peptide. In certain aspects, the peptide analog comprising one or more non-conservative amino acid substitutions inhibits the binding interaction between EGFR and HSP90 to an extent better than the parent peptide.

In some embodiments, and/or one or more amino acid insertions or deletions, in reference to the parent peptide described herein. In some embodiments, the peptide analog comprises an insertion of one or more amino acids at the N- or C-terminus in reference to the parent peptide. In some embodiments, the peptide analog comprises a deletion of one or more amino acids at the N- or C-terminus in reference to the parent peptide. In these aspects, the peptide analog still functions to a similar extent, the same extent, or an improved extent as the parent peptide to inhibit the binding interaction between EGFR and HSP90.

In some aspects, the peptide analog is a peptidomimetic. Peptidomimetics as well as methods of making the same are known in the art. See, for example, *Advances in Amino Acid Mimetics and Peptidomimetics*, Volumes 1 and 2, ed., Abell, A., JAI Press Inc., Greenwich, Conn., 2006. In some aspects, the peptidomimetic is a D-peptide peptidomimetic comprising D-isomer amino acids. In some aspects, the peptidomimetic is a peptoid in which the side chain of an amino acid is connected to the alpha nitrogen atom of the peptide backbone. Methods of making peptoids are known in the art. See, e.g., Zuckermann et al., *JACS* 114(26): 10646-10647 (1992) and *Design, Synthesis, and Evaluation of Novel Peptoids*, Fowler, Sarah, University of Wisconsin-Madison, 2008. In some aspects, the peptidomimetic is a β-peptide comprising β amino acids which have their amino group bonded to the β-cargon rather than the alpha carbon. Methods of making β-peptides are known in the art. See, for example, Seebach et al., *Helvetica Chimica Acta* 79(4): 913-941 (1996).

Pharmaceutically Acceptable Salts

With regard to the present disclosures, the compounds that inhibit a binding interaction between an EGFR and HSP90, (collectively referred to hereinafter as "active agents") in some aspects is in the form of a salt, e.g., a pharmaceutically acceptable salt. Such salts can be prepared in situ during the final isolation and purification of the active agent or separately prepared by reacting a free base function with a suitable acid. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenyl-propionate, picrate, pivalate, propionate, succinate, tartrate, thiocyanate, phosphate, glutamate, bicarbonate, p-toluene-sulfonate, and undecanoate.

Basic addition salts also can be prepared in situ during the final isolation and purification of the active agent, or by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like.

Further, basic nitrogen-containing groups can be quaternized with such active agents as lower alkyl halides such as methyl, ethyl, propyl, and butyl chlorides, bromides, and iodides; long chain halides such as decyl, lauryl, myristyl, and stearyl chlorides, bromides, and iodides; arylalkyl halides like benzyl and phenethyl bromides and others. Water or oil-soluble or dispersible products are thereby obtained.

Isolated and Purified

The compounds of the present disclosures that inhibit a binding interaction between an EGFR and an HSP90 can be isolated and/or purified. The term "isolated" as used herein means having been removed from its natural environment. The term "purified" as used herein means having been increased in purity, wherein "purity" is a relative term, and not to be necessarily construed as absolute purity. In exemplary aspects, the purity of the compound (e.g., in the composition) is at least or about 50%, at least or about 60%, at least or about 70%, at least or about 80%, at least or about 90%, at least or about 95%, or at least or about 98% or is about 100%.

Methods of Making Peptides

The peptides of the present disclosure may be obtained by methods known in the art. Suitable methods of de novo synthesizing peptides are described in, for example, Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752. Additional exemplary methods of making the peptides of the present disclosures are set forth herein.

In some embodiments, the peptides described herein are commercially synthesized by companies, such as Synpep (Dublin, Calif.), Peptide Technologies Corp. (Gaithersburg, Md.), Multiple Peptide Systems (San Diego, Calif.), Peptide 2.0 Inc. (Chantilly, Va.), and American Peptide Co. (Sunnyvale, Calif.). In this respect, the peptides can be synthetic, recombinant, isolated, and/or purified.

Also, in some aspects, the peptides are recombinantly produced using a nucleic acid encoding the amino acid sequence of the peptide using standard recombinant methods. See, for instance, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994.

In some embodiments, the glucagon analogs of the disclosure are isolated. The term "isolated" as used herein means having been removed from its natural environment. In exemplary embodiments, the analog is made through recombinant methods and the analog is isolated from the host cell.

In some embodiments, the glucagon analogs of the disclosure are purified. The term "purified," as used herein relates to the isolation of a molecule or compound in a form that is substantially free of contaminants which in some aspects are normally associated with the molecule or compound in a native or natural environment and means having been increased in purity as a result of being separated from other components of the original composition. The purified peptide or compound include, for example, peptides substantially free of nucleic acid molecules, lipids, and carbohydrates, or other starting materials or intermediates which are used or formed during chemical synthesis of the peptides. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%.

Nucleic Acids

In some embodiments of the present disclosures, the compound that inhibits a binding interaction between an EGFR and HSP90 comprises a nucleic acid comprising a nucleotide sequence encoding any of the antibodies or peptides described herein (including analogs thereof). The nucleic acid can comprise any nucleotide sequence which encodes any of the antibodies, peptides, or analogs thereof. By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. In other embodiments, the nucleic acid comprises one or more insertions, deletions, inversions, and/or substitutions.

In some aspects, the nucleic acids of the present disclosures are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids in some aspects are constructed based on chemical synthesis and/or enzymatic ligation reactions using procedures known in the art. See, for example, Sambrook et al., supra; and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-$N^2$-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

Recombinant Expression Vector

The nucleic acids of the present disclosures in some aspects are incorporated into a recombinant expression vector. In this regard, the present disclosures provides recombinant expression vectors comprising any of the presently disclosed nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the present disclosures are not naturally-occurring as a whole. However, parts of the vectors can be naturally-occurring. The presently disclosed recombinant expression vectors may comprise any type of nucleotides, including, but not limited to DNA and RNA, which may be single-stranded or double-stranded, synthesized or obtained in part from natural sources, and which can contain natural, non-natural or altered nucleotides. The recombinant expression vectors may comprise naturally-occurring or non-naturally-occurring internucleotide linkages, or both types of linkages. In some aspects, the altered nucleotides or non-naturally occurring internucleotide linkages do not hinder the transcription or replication of the vector.

The recombinant expression vector of the present disclosures can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGTIO, λGTl 1, λZapII (Stratagene), λEMBL4, and λNMl 149, also can be used. Examples of plant expression vectors include pBIOl, pBI101.2, pBI101.3, pBI121 and pBIN19 (Clontech). Examples of animal expression vectors include pEUK-Cl, pMAM and pMAMneo (Clontech). In some aspects, the recombinant expression vector is a viral vector, e.g., a retroviral vector.

The recombinant expression vectors of the present disclosures can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

In some aspects, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector may include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the presently disclosed expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the polypeptide (including functional portions and functional variants thereof), or to the nucleotide sequence which is complementary to or which hybridizes to the nucleotide sequence encoding the polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The presently disclosed recombinant expression vectors may be designed for either transient expression, for stable expression, or for both. Also, the recombinant expression vectors may be made for constitutive expression or for inducible expression. Further, the recombinant expression vectors may be made to include a suicide gene.

As used herein, the term "suicide gene" refers to a gene that causes the cell expressing the suicide gene to die. The suicide gene in some aspects is a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews. Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Host Cells

The present disclosures further provides a host cell comprising any of the recombinant expression vectors described herein. As used herein, the term "host cell" refers to any type of cell that can contain the presently disclosed recombinant expression vector. The host cell in some aspects is a eukaryotic cell, e.g., plant, animal, fungi, or algae, or can be a prokaryotic cell, e.g., bacteria or protozoa. The host cell in some aspects is a cultured cell or a primary cell, i.e., isolated directly from an organism, e.g., a human. The host cell in some aspects is an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is in some aspects is a prokaryotic cell, e.g., a DH5α cell. For purposes of producing a recombinant polypeptide the host cell is in some aspects a mammalian cell, e.g., a human cell. The host cell may be of any cell type, can originate from any type of tissue, and can be of any developmental stage.

Also provided by the present disclosures is a population of cells comprising at least one host cell described herein. The population of cells in some aspects is a heterogeneous population comprising the host cell comprising any of the recombinant expression vectors described, in addition to at least one other cell, which does not comprise any of the recombinant expression vectors. Alternatively, in some aspects, the population of cells is a substantially homogeneous population, in which the population comprises mainly of host cells (e.g., consisting essentially of) comprising the recombinant expression vector. The population in some aspects is a clonal population of cells, in which all cells of the population are clones of a single host cell comprising a recombinant expression vector, such that all cells of the population comprise the recombinant expression vector. In one embodiment of the present disclosures, the population of cells is a clonal population comprising host cells comprising a recombinant expression vector as described herein.

Conjugates

In some embodiments, the compounds of the present disclosures are attached or linked or conjugated to a second moiety (e.g., a heterologous moiety, a conjugate moiety). As used herein, the term "heterologous moiety" is synonymous with "conjugate moiety" and refers to any molecule (chemical or biochemical, naturally-occurring or non-coded) which is different from the compounds of the present disclosures. Exemplary heterologous moieties include, but are not limited to, a polymer, a carbohydrate, a lipid, a nucleic acid, an oligonucleotide, a DNA or RNA, an amino acid, peptide, polypeptide, protein, therapeutic agent, (e.g., a cytotoxic agent, cytokine), or a diagnostic agent.

In some embodiments, the compounds are chemically modified with various substituents. In some embodiments, the chemical modifications impart additional desirable characteristics as discussed herein. Chemical modifications in some aspects take a number of different forms such as heterologous peptides, polysaccharides, lipids, radioisotopes, non-standard amino acid resides and nucleic acids, metal chelates, and various cytotoxic agents.

In some embodiments, the compounds are fused to heterologous peptides to confer various properties, e.g., increased solubility and/or stability and/or half-life, resistance to proteolytic cleavage, modulation of clearance, targeting to particular cell or tissue types. In some embodiments, the compound is linked to a Fc domain of IgG or other immunoglobulin. In some embodiments, the compound is fused to alkaline phosphatase (AP). Methods for making Fc or AP fusion constructs are found in WO 02/060950. By fusing the compound with protein domains that have specific properties (e.g. half life, bioavailability) it is possible to confer these properties to the compound of the present disclosures.

When the compounds are peptides, they can be modified, for instance, by glycosylation, amidation, carboxylation, or phosphorylation, or by the creation of acid addition salts, amides, esters, in particular C-terminal esters, and N-acyl derivatives, as discussed above. The peptides also can be modified to create peptide derivatives by forming covalent or noncovalent complexes with other moieties. Covalently bound complexes can be prepared by linking the chemical moieties to functional groups on the side chains of amino acids comprising the peptides, or at the N- or C-terminus.

Peptides can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin). Examples of analogs are described in WO 98/28621 and in Olofsson, et al, Proc. Nat'l. Acad. Sci. USA, 95:11709-11714 (1998), U.S. Pat. Nos. 5,512,545, and 5,474,982; U.S. Patent Application Nos. 20020164687 and 20020164710.

Cysteinyl residues most commonly are reacted with haloacetates (and corresponding amines), such as chloroacetic acid or chloroacetamide, to give carboxymethyl or carbocyamidomethyl derivatives. Cysteinyl residues also are derivatized by reaction with bromotrifluoroacetone, α-bromo-.beta.-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, orchloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R1) such as 1-cyclohexyl-3-(2-morpholinyl-(4-ethyl) carbodiimide or 1-ethyl-3 (4 azonia 4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking the binding construct to water-insoluble support matrixes. Such derivation may also provide the linker that may connect adjacent binding elements in a binding construct, or a binding elements to a heterologous peptide, e.g., a Fc fragment. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiiobis(succinimidyl-propioonate), and bifunctional maleimides such as bis-N-maleimido-1,8-octane. Derivatizing agents such as methyl-3-[(p-azidophenyl)dithio]propioimidate yield photoactivatable intermediates that are capable of forming cross links in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440, incorporated herein by reference, are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecule Properties, W. H. Freeman & Co., San Francisco, pp. 79-86, 1983), acetylation of the N-terminal amine, and, in some instances, amidation of the C-terminal carboxyl groups. Such derivatives are chemically modified polypeptide compositions in which the binding construct polypeptide is linked to a polymer.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the binding construct becomes attached to one or more polymer molecules, and (b) obtaining the reaction product(s). The optimal reaction conditions will be determined based on known parameters and the desired result. For example, the larger the ratio of polymer molecules:protein, the greater the amount of attached polymer molecule. In some embodiments, the compound may have a single polymer molecule moiety at the amino terminus. (See, e.g., U.S. Pat. No. 5,234,784).

Derivatized binding constructs disclosed herein may have additional activities, enhanced or reduced biological activity, or other characteristics, such as increased or decreased half-life, as compared to the non-derivatized molecules.

In some embodiments, the compound is directly joined to a conjugate moiety in the absence of a linker. In alternative aspects, the compound is indirectly connected to the conjugate moiety via one or more linkers. Whether directly joined together or indirectly joined together through a linker, the compound may be connected through covalent bonds (e.g., a peptide, ester, amide, or sulfhydryl bond) or non-covalent bonds (e.g., via hydrophobic interaction, hydrogen bond, van der Waals bond, electrostatic or ionic interaction), or a combination thereof. The compound of the present disclosures and conjugate moiety may be connected via any means known in the art, including, but not limited to, via a linker of any of the present disclosures. See, for example, the section herein entitled "Linkers."

Conjugates: Fc Fusions

For substituents such as an Fc region of human IgG, the fusion can be fused directly to a compound of the present disclosures or fused through an intervening sequence. For example, a human IgG hinge, CH2 and CH3 region may be fused at either the N-terminus or C-terminus of a binding construct to attach the Fc region. The resulting Fc-fusion construct enables purification via a Protein A affinity column (Pierce, Rockford, Ill.). Peptide and proteins fused to an Fc region can exhibit a substantially greater half-life in vivo than the unfused counterpart. A fusion to an Fc region allows for dimerization/multimerization of the fusion polypeptide. The Fc region may be a naturally occurring Fc region, or may be modified for superior characteristics, e.g., therapeutic qualities, circulation time, reduced aggregation. As noted above, in some embodiments, the compounds are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J. Immunol. 175:6694-701, 2005). Amino acid residues involved in IgE receptor binding are described in Sayers et al. (J Biol. Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγR5 (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγR5 (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Heterologous Moieties: Polymers, Carbohydrates, and Lipids

In some embodiments, the heterologous moiety is a polymer. The polymer may be branched or unbranched. The polymer may be of any molecular weight. The polymer in some embodiments has an average molecular weight of between about 2 kDa to about 100 kDa (the term "about" indicating that in preparations of a water soluble polymer, some molecules will weigh more, some less, than the stated molecular weight). The average molecular weight of the polymer is in some aspect between about 5 kDa and about 50 kDa, between about 12 kDa to about 40 kDa or between about 20 kDa to about 35 kDa.

In some embodiments, the polymer is modified to have a single reactive group, such as an active ester for acylation or an aldehyde for alkylation, so that the degree of polymerization may be controlled. The polymer in some embodiments is water soluble so that the protein to which it is attached does not precipitate in an aqueous environment, such as a physiological environment. In some embodiments, when, for example, the composition is used for therapeutic use, the polymer is pharmaceutically acceptable. Additionally, in some aspects, the polymer is a mixture of polymers, e.g., a co-polymer, a block co-polymer.

In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

In some embodiments, the polymer is a water-soluble polymer or a hydrophilic polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In some aspects, the water soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C10) alkoxy- or aryloxy-polyethylene glycol); monomethoxy-polyethylene glycol; dextran (such as low molecular weight dextran, of, for example about 6 kD), cellulose; cellulose; other carbohydrate-based polymers, poly-(N-vinyl pyrrolidone)polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which may be used to prepare covalently attached multimers.

A particularly preferred water-soluble polymer for use herein is polyethylene glycol (PEG). As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophibic nature, thus creating a water shell or hydration sphere when attached to other proteins or polymer surfaces. PEG is nontoxic, non-immunogenic, and approved by the Food and Drug Administration for internal consumption.

Proteins or enzymes when conjugated to PEG have demonstrated bioactivity, non-antigenic properties, and decreased clearance rates when administered in animals. F. M. Veronese et al., Preparation and Properties of Monomethoxypoly(ethylene glycol)-modified Enzymes for Therapeutic Applications, in J. M. Harris ed., Poly(Ethylene Glycol) Chemistry—Biotechnical and Biomedical Applications, 127-36, 1992, incorporated herein by reference. These phenomena are due to the exclusion properties of PEG in preventing recognition by the immune system. In addition, PEG has been widely used in surface modification procedures to decrease protein adsorption and improve blood compatibility. S. W. Kim et al., Ann. N.Y. Acad. Sci. 516: 116-30 1987; Jacobs et al., Artif. Organs 12: 500-501, 1988; Park et al., J. Poly. Sci, Part A 29:1725-31, 1991, incorporated herein by reference. Hydrophobic polymer surfaces, such as polyurethanes and polystyrene can be modified by the grafting of PEG (MW 3,400) and employed as nonthrombogenic surfaces. Surface properties (contact angle) can be more consistent with hydrophilic surfaces, due to the hydrating effect of PEG. More importantly, protein (albumin and other plasma proteins) adsorption can be greatly reduced, resulting from the high chain motility, hydration sphere, and protein exclusion properties of PEG.

PEG (MW 3,400) was determined as an optimal size in surface immobilization studies, Park et al., J. Biomed. Mat. Res. 26:739-45, 1992, while PEG (MW 5,000) was most beneficial in decreasing protein antigenicity. (F. M. Veronese et al., In J. M. Harris, et al., Poly(Ethylene Glycol) Chemistry—Biotechnical and Biomedical Applications, 127-36.)

Methods for preparing pegylated compounds may comprise the steps of (a) reacting the compound with polyethylene glycol (such as a reactive ester or aldehyde derivative of PEG) under conditions whereby the compound becomes attached to one or more PEG groups, and (b) obtaining the reaction product(s). In general, the optimal reaction conditions for the acylation reactions will be determined based on known parameters and the desired result. For example, the larger the ratio of PEG: compound, the greater the percentage of poly-pegylated product. In some embodiments, the compound will have a single PEG moiety at the N-terminus. See U.S. Pat. No. 8,234,784, herein incorporated by reference.

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

Heterologous Moieties: Therapeutic Agents

In some embodiments, the heterologous moiety is a therapeutic agent. The therapeutic agent may be any of those known in the art. Examples of therapeutic agents that are contemplated herein include, but are not limited to, natural enzymes, proteins derived from natural sources, recombinant proteins, natural peptides, synthetic peptides, cyclic peptides, antibodies, receptor agonists, cytotoxic agents, immunoglobins, beta-adrenergic blocking agents, calcium channel blockers, coronary vasodilators, cardiac glycosides, antiarrhythmics, cardiac sympathomemetics, angiotensin converting enzyme (ACE) inhibitors, diuretics, inotropes, cholesterol and triglyceride reducers, bile acid sequestrants, fibrates, 3-hydroxy-3-methylgluteryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin II receptor antagonists, peripheral vasodilators, antiandrogens, estrogens, antibiotics, retinoids, insulins and analogs, alpha-glucosidase inhibitors, biguanides, meglitinides, sulfonylureas, thizaolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-$HT_4$ partial agonists, antihistamines, cannabinoids, dopamine antagonists, serotonin antagonists, cytoprotectives, histamine H2-receptor antagonists, mucosal protective agent, proton pump inhibitors, *H. pylori* eradication therapy, erythropoieses stimulants, hematopoietic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-$A_2$ inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptse inhibitors, protease inhibitors, anemia, Kaposi's sarcoma, aminoglycosides, carbapenems, cephalosporins, glycopeptides, lincosamides, macrolies, oxazolidinones, penicillins, streptogramins, sulfonamides, trimethoprim and derivatives, tetracyclines, anthelmintics, amebicies, biguanides, cinchona alkaloids, folic acid antagonists, quinoline derivatives, *Pneumocystis carinii* therapy, hydrazides, imidazoles, triazoles, nitroimidzaoles, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigrane preparations, biological response modifiers, carbamic acid eaters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, antracyclines, actinomycinds, camptothecin derivatives, epipodophyllotoxins, taxanes, vinca alkaloids and analogs, antiandrogens, antiestrogens, nonsteroidal aromatase inhibitors, protein kinase inhibitor antineoplastics, azaspirodecanedione derivatives, anxiolytics, stimulants, monoamind reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g. lidocaine, articaine hydrochloride, bupivacaine hydrochloride), antipyretics, hynotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opoid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, vitamin K analogs and antagonists.

The compounds of the present disclosures may be conjugated to one or more cytokines and growth factors that are effective in inhibiting tumor metastasis, and wherein the cytokine or growth factor has been shown to have an antiproliferative effect on at least one cell population. Such cytokines, lymphokines, growth factors, or other hematopoietic factors include, but are not limited to: M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin. Additional growth factors for use herein include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor α, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epithelial-derived neutrophil attractant, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, pre-B cell growth stimulating factor, stem cell factor, stem cell factor receptor, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, and chimeric proteins and biologically or immunologically active fragments thereof.

In some embodiments, the conjugate comprises a compound as described herein and a cytotoxic agent. The cytotoxic agent is any molecule (chemical or biochemical) which is toxic to a cell. In some aspects, when a cytotoxic agent is conjugated to a compound of the present disclosures, the results obtained are synergistic. That is to say, the effectiveness of the combination therapy of a compound and the cytotoxic agent is synergistic, i.e., the effectiveness is greater than the effectiveness expected from the additive individual effects of each. Therefore, the dosage of the cytotoxic agent can be reduced and thus, the risk of the toxicity problems and other side effects is concomitantly reduced. In some embodiments, the cytotoxic agent is a chemotherapeutic agent. Chemotherapeutic agents are known in the art and include, but not limited to, platinum coordination compounds, topoisomerase inhibitors, antibiotics, antimitotic alkaloids and difluoronucleosides, as described in U.S. Pat. No. 6,630,124.

In some embodiments, the chemotherapeutic agent is a platinum coordination compound. The term "platinum coordination compound" refers to any tumor cell growth inhibiting platinum coordination compound that provides the platinum in the form of an ion. In some embodiments, the platinum coordination compound is cis-diamminediaquoplatinum (II)-ion; chloro(diethylenetriamine)-platinum(II) chloride; dichloro(ethylenediamine)-platinum(II), diammine (1,1-cyclobutanedicarboxylato) platinum(II) (carboplatin); spiroplatin; iproplatin; diammine(2-ethylmalonato)-platinum(II); ethylenediaminemalonatoplatinum(II); aqua(1,2-diaminodyclohexane)-sulfatoplatinum(II); (1,2-diaminocyclohexane)malonatoplatinum(II); (4-caroxyphthalato)(1,2-diaminocyclohexane)platinum(II); (1,2-diaminocyclohexane)-(isocitrato)platinum(II); (1,2-diaminocyclohexane)cis(pyruvato)platinum(II); (1,2-diaminocyclohexane)oxalatoplatinum(II); ormaplatin; and tetraplatin.

In some embodiments, cisplatin is the platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle. Other platinum coordination compounds suitable for use in the present invention are known and are available commercially and/or can be prepared by conventional techniques. Cisplatin, or cis-dichlorodiaminoplatinum II, has been used successfully for many years as a chemotherapeutic agent in the treatment of various human solid malignant tumors. More recently, other diamino-platinum complexes have also shown efficacy as chemotherapeutic agents in the treatment of various human solid malignant tumors. Such diamino-platinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

In some embodiments, the chemotherapeutic agent is a topoisomerase inhibitor. Topoisomerases are enzymes that are capable of altering DNA topology in eukaryotic cells. They are critical for cellular functions and cell proliferation. Generally, there are two classes of topoisomerases in eukaryotic cells, type I and type II. Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Various topoisomerase inhibitors have recently shown clinical efficacy in the treatment of humans afflicted with ovarian, cancer, esophageal cancer or non-small cell lung carcinoma.

In some aspects, the topoisomerase inhibitor is camptothecin or a camptothecin analog. Camptothecin is a water-insoluble, cytotoxic alkaloid produced by Camptotheca accuminata trees indigenous to China and Nothapodytes foetida trees indigenous to India. Camptothecin exhibits tumor cell growth inhibiting activity against a number of tumor cells. Compounds of the camptothecin analog class are typically specific inhibitors of DNA topoisomerase I. By the term "inhibitor of topoisomerase" is meant any tumor cell growth inhibiting compound that is structurally related to camptothecin. Compounds of the camptothecin analog class include, but are not limited to; topotecan, irinotecan and 9-aminocamptothecin.

In additional embodiments, the cytotoxic agent is any tumor cell growth inhibiting camptothecin analog claimed or described in: U.S. Pat. No. 5,004,758, issued on Apr. 2, 1991 and European Patent Application Number 88311366.4, published on Jun. 21, 1989 as 20' Publication Number EP 0 321 122; U.S. Pat. No. 4,604,463, issued on Aug. 5, 1986 and European Patent Application Publication Number EP 0 137 145, published on Apr. 17, 1985; U.S. Pat. No. 4,473,692, issued on Sep. 25, 1984 and European Patent Application Publication Number EP 0 074 256, published on Mar. 16, 1983; U.S. Pat. No. 4,545,880, issued on Oct. 8, 1985 and European Patent Application Publication Number EP 0 074 256, published on Mar. 16, 1983; European Patent Application Publication Number EP 0 088 642, published on Sep. 14, 1983; Wani et al., J. Med. Chem., 29, 2358-2363 (1986); Nitta et al., Proc. 14th International Congr. Chemotherapy, Kyoto, 1985, Tokyo Press, Anticancer Section 1, p. 28-30, especially a compound called CPT-11. CPT-11 is a camptothecin analog with a 4-(piperidino)-piperidine side chain joined through a carbamate linkage at C-10 of 10-hydroxy-7-ethyl camptothecin. CPT-11 is currently undergoing human clinical trials and is also referred to as irinotecan; Wani et al, J. Med. Chem., 23, 554 (1980); Wani et. al., J. Med. Chem., 30, 1774 (1987); U.S. Pat. No. 4,342,776, issued on Aug. 3, 1982; U.S. patent application Ser. No. 581,916, filed on Sep. 13, 1990 and European Patent Application Publication Number EP 418 099, published on Mar. 20, 1991; U.S. Pat. No. 4,513,138, issued on Apr. 23, 1985 and European Patent Application Publication Number EP 0 074 770, published on Mar. 23, 1983; U.S. Pat. No. 4,399,276, issued on Aug. 16, 1983 and European Patent Application Publication Number 0 056 692, published on Jul. 28, 1982; the entire disclosure of each of which is hereby incorporated by reference. All of the above-listed compounds of the camptothecin analog class are available commercially and/or can be prepared by conventional techniques including those described in the above-listed references. The topoisomerase inhibitor may be selected from the group consisting of topotecan, irinotecan and 9-aminocamptothecin.

The preparation of numerous compounds of the camptothecin analog class (including pharmaceutically acceptable salts, hydrates and solvates thereof) as well as the preparation of oral and parenteral pharmaceutical compositions comprising such a compounds of the camptothecin analog class and an inert, pharmaceutically acceptable carrier or diluent, is extensively described in U.S. Pat. No. 5,004,758, issued on Apr. 2, 1991 and European Patent Application Number 88311366.4, published on Jun. 21, 1989 as Publication Number EP 0 321 122, the teachings of which are incorporated herein by reference.

In still yet other embodiments of the present disclosures, the chemotherapeutic agent is an antibiotic compound. Suitable antibiotic include, but are not limited to, doxorubicin, mitomycin, bleomycin, daunorubicin and streptozocin.

In some embodiments, the chemotherapeutic agent is an antimitotic alkaloid. In general, antimitotic alkaloids can be extracted from *Cantharanthus roseus*, and have been shown to be efficacious as anticancer chemotherapy agents. A great number of semi-synthetic derivatives have been studied both chemically and pharmacologically (see, O. Van Tellingen et al, Anticancer Research, 12, 1699-1716 (1992)). The antimitotic alkaloids of the present invention include, but are not limited to, vinblastine, vincristine, vindesine, Taxol and vinorelbine. The latter two antimitotic alkaloids are commercially available from Eli Lilly and Company, and Pierre Fabre Laboratories, respectively (see, U.S. Pat. No. 5,620,985). In a preferred aspect of the present invention, the antimitotic alkaloid is vinorelbine.

In other embodiments of the present disclosures, the chemotherapeutic agent is a difluoronucleoside. 2'-deoxy-2',2'-difluoronucleosides are known in the art as having antiviral activity. Such compounds are disclosed and taught in U.S. Pat. Nos. 4,526,988 and 4,808,614. European Patent Application Publication 184,365 discloses that these same difluoronucleosides have oncolytic activity. In certain specific aspects, the 2'-deoxy-2',2'-difluoronucleoside used in the compositions and methods of the present invention is 2'-deoxy-2',2'-difluorocytidine hydrochloride, also known as gemcitabine hydrochloride. Gemcitabine is commercially available or can be synthesized in a multi-step process as disclosed and taught in U.S. Pat. Nos. 4,526,988, 4,808,614 and 5,223,608, the teachings of which are incorporated herein by reference.

Conjugates: Targeted Forms

One of ordinary skill in the art will readily appreciate that the compounds of the present disclosure can be modified in any number of ways, such that the therapeutic or prophylactic efficacy of the compound of the present disclosures is increased through the modification. For instance, the compound of the present disclosure can be conjugated either directly or indirectly through a linker to a targeting moiety. The practice of conjugating compounds to targeting moieties is known in the art. See, for instance, Wadhwa et al., *J Drug Targeting*, 3, 111-127 (1995) and U.S. Pat. No. 5,087,616. The term "targeting moiety" as used herein, refers to any molecule or agent that specifically recognizes and binds to a cell-surface receptor, such that the targeting moiety directs the delivery of the compound of the present disclosures to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups. The term "linker" in some embodiments refers to any agent or molecule that bridges the compound of the present disclosures to the targeting moiety. The linker may be any of those described herein under the section entitled "Linkers." One of ordinary skill in the art recognizes that sites on the compound of the present disclosures, which are not necessary for the function of the compound, are ideal sites for attaching a linker and/or a targeting moiety, provided that the linker and/or targeting moiety, once attached to the compound, do(es) not interfere with the function of the compound, i.e., the ability to inhibit the binding interaction between EGFR and HSP90, as described herein.

Linkers

In some embodiments, the conjugate comprises a linker that joins the compound of the present disclosures to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. In some embodiments, the linker is an amino acid or a peptidyl linker. Such peptidyl linkers may be any length. Exemplary linkers are from about 1 to 50 amino acids in length, 5 to 50, 3 to 5, 5 to 10, 5 to 15, or 10 to 30 amino acids in length.

Dimers & Multimers

In some embodiments, the compound is provided as a dimer or a multimer in which more than one compound of the present disclosures are linked together. The dimer in some aspects is a homodimer comprising two compounds of the same type (e.g., same structure) linked together. In alternative aspects, the dimer is a heterodimer comprising two compounds of the present disclosures, wherein the two compounds are structurally distinct from each other. The multimer in some aspects is a homomultimer comprising more than one compound of the present disclosures and each compound are of the same type (e.g., same structure). In alternative aspects, the multimer is a heteromultimer comprising more than one compound of the present disclosures and wherein at least two compounds of the heteromultimer are structurally distinct from the other. Two or more of the compounds can be linked together using standard linking agents and procedures known to those skilled in the art. In certain embodiments, the linker connecting the two (or more) compounds is a linker as described in the section entitled "Linkers." In some embodiments, the linker is a disulfide bond. For example, each monomer of the dimer may comprise a sulfhydryl and the sulfur atom of each participates in the formation of the disulfide bond.

Compositions

The present disclosures further provide compositions comprising a compound that inhibits a binding interaction between EGFR and HSP90, e.g., an antibody, antigen binding fragment, aptamer, peptide, peptide analog, pharmaceutically acceptable salt, conjugate, multimer, dimer, as described herein. The compositions in some aspects comprise the compounds in isolated and/or purified form. In some aspects, the composition comprises a single type (e.g., structure) of a compound of the present disclosures or comprises a combination of two or more compounds of the present disclosures, wherein the combination comprises two or more compounds of different types (e.g., structures).

In some aspects, the composition comprises agents which enhance the chemico-physico features of the compound, e.g., via stabilizing the compound at certain temperatures, e.g., room temperature, increasing shelf life, reducing degradation, e.g., oxidation protease mediated degradation, increasing half-life of the compound, etc. In some aspects, the composition comprises any of the agents disclosed herein as a heterologous moiety or conjugate moiety, optionally in admixture with the compounds of the present disclosures or conjugated to the compounds.

In certain aspects, the composition comprises a delivery agent which aids in localizing the compound of the present disclosures to the appropriate place. In certain aspects, the composition comprises a compound of the present disclosures (e.g., a peptide that inhibits a binding interaction between EGFR and HSP90) and a peptide delivery agent. In some aspects, the peptide delivery agent is a cell penetrating peptide (CPP). In particular aspects, the composition comprises a CPP fused to the compound, e.g., the composition comprises a fusion peptide product comprising a peptide of the present disclosures that inhibits a binding interaction between EGFR and HSP90 fused to a CPP. In certain aspects, the CPP comprises the amino acid sequence YGRKKRRQRRR (SEQ ID NO: 31).

Pharmaceutical Compositions and Formulations

In yet other aspects of the present disclosures, the composition comprises a compound that inhibits a binding interaction between EGFR and HSP90 and additionally comprises a pharmaceutically acceptable carrier, diluents, or excipient. In some embodiments, the compound of the present disclosures, the pharmaceutically acceptable salt, the conjugate, the dimer or multimer, of the present disclosures (hereinafter referred to as "active agents") is formulated into a pharmaceutical composition comprising the active agent, along with a pharmaceutically acceptable carrier, diluent, or excipient. In this regard, the present disclosures further provides pharmaceutical compositions comprising an active agent that inhibits a binding interaction between EGFR and HSP90 which is intended for administration to a subject, e.g., a mammal.

In some embodiments, the active agent is present in the pharmaceutical composition at a purity level suitable for administration to a patient. In some embodiments, the active agent has a purity level of at least about 90%, about 91%, about 92%, about 93%, about 94%, about 95%, about 96%, about 97%, about 98% or about 99%, and a pharmaceutically acceptable diluent, carrier or excipient. The pharmaceutical composition in some aspects comprises the active agent of the present disclosure at a concentration of at least A, wherein A is about 0.001 mg/ml, about 0.01 mg/ml, 0 about 1 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml or higher. In some embodiments, the pharmaceutical composition comprises the active agent at a concentration of at most B, wherein B is about 30 mg/ml, about 25 mg/ml, about 24 mg/ml, about 23, mg/ml, about 22 mg/ml, about 21 mg/ml, about 20 mg/ml, about 19 mg/ml, about 18 mg/ml, about 17 mg/ml, about 16 mg/ml, about 15 mg/ml, about 14 mg/ml, about 13 mg/ml, about 12 mg/ml, about 11 mg/ml, about 10 mg/ml, about 9 mg/ml, about 8 mg/ml, about 7 mg/ml, about 6 mg/ml, about 5 mg/ml, about 4 mg/ml, about 3 mg/ml, about 2 mg/ml, about 1 mg/ml, or about 0.1 mg/ml. In some embodiments, the compositions may contain an active agent at a concentration range of A to B mg/ml, for example, about 0.001 to about 30.0 mg/ml.

Depending on the route of administration, the particular active agent intended for use, as well as other factors, the pharmaceutical composition may comprise additional pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

Accordingly, in some embodiments, the pharmaceutical composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC) chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edentate, disodium edentate, disodium hydrogen phosphate, docusate calcium, docusate potassium, docusate sodium, dodecyl gallate, dodecyltrimethylammonium bromide, edentate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil, type II, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, postassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), theobroma oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiological compatible pH. The buffering agents may include any compounds capable of buffering at the desired pH such as, for example, phosphate buffers (e.g., PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g., at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM).

Routes of Administration

With regard to the present disclosures, the active agent, pharmaceutical composition comprising the same, may be administered to the subject via any suitable route of administration. The following discussion on routes of administration is merely provided to illustrate exemplary embodiments and should not be construed as limiting the scope in any way.

Formulations suitable for oral administration can consist of (a) liquid solutions, such as an effective amount of the active agent of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the active agent of the present disclosure in a flavor, usually sucrose and acacia or tragacanth, as well as pastilles comprising the active agent of the present disclosure in an inert base, such as gelatin and glycerin, or sucrose and acacia, emulsions, gels, and the like containing, in addition to, such excipients as are known in the art.

The active agents of the present disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the active agent is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The active agent of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations in some embodiments contain from about 0.5% to about 25% by weight of the active agent of the present disclosure in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the active agent of the present disclosures can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the active agent of the disclosure can be formulated as inclusion complexes, such as cyclodextrin inclusion complexes, or liposomes.

Dosages

The active agents of the disclosure are believed to be useful in methods of inhibiting a binding interaction between EGFR and HSP90, methods of increasing EGFR degradation, methods of treating cancer in a subject, and methods of sensitizing tumors to treatment, as further described herein. For purposes of the disclosure, the amount or dose of the active agent administered should be sufficient to effect, e.g., a therapeutic or prophylactic response, in the subject or animal over a reasonable time frame. For example, the dose of the active agent of the present disclosure should be sufficient to treat cancer as described herein in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular active agent and the condition of the animal (e.g., human), as well as the body weight of the animal (e.g., human) to be treated.

Many assays for determining an administered dose are known in the art. For purposes herein, an assay, which comprises comparing the extent to which cancer is treated upon administration of a given dose of the active agent of the present disclosure to a mammal among a set of mammals, each set of which is given a different dose of the active agent, could be used to determine a starting dose to be administered to a mammal. The extent to which cancer is treated upon administration of a certain dose can be represented by, for example, the cytotoxicity of the active agent or the extent of tumor regression achieved with the active agent in a mouse xenograft model. Methods of measuring cytotoxicity of compounds and methods of assaying tumor regression are known in the art, including, for instance, the methods described in the EXAMPLES set forth below.

The dose of the active agent of the present disclosure also will be determined by the existence, nature and extent of any adverse side effects that might accompany the administration of a particular active agent of the present disclosure. Typically, the attending physician will decide the dosage of the active agent of the present disclosure with which to treat each individual patient, taking into consideration a variety of factors, such as age, body weight, general health, diet, sex, active agent of the present disclosure to be administered, route of administration, and the severity of the condition being treated. By way of example and not intending to limit the invention, the dose of the active agent of the present disclosure can be about 0.0001 to about 1 g/kg body weight of the subject being treated/day, from about 0.0001 to about 0.001 g/kg body weight/day, or about 0.01 mg to about 1 g/kg body weight/day. In some embodiments, the dose is up to 50 mg/kg body weight, from about 5 to about 30 mg/kg body weight or from about 8 to about 10 mg/kg body weight.

Controlled Release Formulations

In some embodiments, the active agents described herein can be modified into a depot form, such that the manner in which the active agent of the present disclosures is released into the body to which it is administered is controlled with respect to time and location within the body (see, for example, U.S. Pat. No. 4,450,150). Depot forms of active agents of the present disclosures can be, for example, an implantable composition comprising the active agents and a porous or non-porous material, such as a polymer, wherein the active agent is encapsulated by or diffused throughout the material and/or degradation of the non-porous material. The depot is then implanted into the desired location within the body of the subject and the active agent is released from the implant at a predetermined rate.

The pharmaceutical composition comprising the active agent in certain aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., *J Pharm* 374: 46-52 (2009) and International Patent Application Publication Nos. WO 2008/130158, WO2004/033036; WO2000/032218; and WO 1999/040942.

The instant compositions may further comprise, for example, micelles or liposomes, or some other encapsulated form, or may be administered in an extended release form to provide a prolonged storage and/or delivery effect.

Timing of Administration

The disclosed pharmaceutical compositions and formulations may be administered according to any regimen including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly. Timing, like dosing can be fine-tuned based on dose-response studies, efficacy, and toxicity data, and initially guaged based on timing used for other antibody therapeutics.

Combinations

In some embodiments, the active agents described herein are administered alone, and in alternative embodiments, the active agents described herein are administered in combination with another therapeutic agent, e.g., another active agent of the present disclosures of different type (e.g., structure), or another therapeutic which does not inhibit a binding interaction between EGFR and HSP90. In some aspects, the other therapeutic aims to treat or prevent cancer. In specific aspects, the other therapeutic is one listed under the section entitled "*Heterologous Moieties: Therapeutic Agents.*" In some embodiments, the other therapeutic is a chemotherapeutic agent. In some aspects, the chemotherapeutic agent is a DNA crosslinker or an agent that targets DNA synthesis (e.g., cisplatin). In some aspects, the chemotherapeutic agent comprises any of a platinum coordination compound (e.g., cisplatin), topoisomerase inhibitor (e.g., camptothecin), antibiotic compound (e.g., doxorubicin, mitomycin, bleomycin, daunorubicin, streptozocin), an antimitotic alkaloid (e.g., vinblastine, vincristine, videsine, Taxol, vinorelbine), or an anti-viral (e.g., gemcitabine). In some embodiments, the other therapeutic is an agent used in radiation therapy for the treatment of cancer. In exemplary aspects, the radiation therapy comprises photon beams (e.g., X rays, gamma rays), electron beams and/or charged particle beams. In certain aspects, the radiation therapy comprises external beam radiation therapy (e.g., 3-dimensional conformal radiation therapy (3D-CRT), intensity-modulated radiation therapy (IMRT), image-guided radiation therapy (IGRT), tomotherapy, stereostatic radiosurgery, stereostatic body radiation therapy, proton therapy, and the like). In alternative aspects, the radiation therapy comprises internal radiation therapy (a.k.a., brachytherapy), such as, interstitial brachytherapy. In some aspects, the radiation therapy comprises systemic radiation therapy, e.g., ibritumomab tiuxetan (Zevalin®), tositumomab and iodine I 131 tositumomab (Bexxar®), samarium-153-lexidronam (Quadramet®) and strontium-89 chloride (Metastron®).

In exemplary embodiments, the active agent is administered simultaneously as the other therapeutic. In alternative embodiments, the active agent is administered either before or after the other therapeutic.

Methods of Inhibiting a Binding Interaction Between EGFR and HSP90

Given the importance of the biological roles of EGFR and HSP90, individually, and as shown herein for the first time, in combination with one another, the active agents of the present disclosures are useful for a number of applications in a variety of settings. For example and most simplistically, the active agents of the present disclosures are useful for inhibiting a binding interaction between EGFR and HSP90 in a cell. In this regard, the present disclosures provide a method of inhibiting a binding interaction between EGFR and HSP90 in a cell. The method comprises contacting the cell with a compound of the present disclosures, a pharmaceutically acceptable salt thereof, a conjugate comprising the compound, or a multimer or dimer comprising the compound, in an amount effective to inhibit the binding interaction. In some aspects, the cell is part of an in vitro or ex vivo cell culture or in vitro or ex vivo tissue sample. In some aspects, the cell is an in vivo cell. In certain embodiments, the method is intended for research purposes, and, in other embodiments, the method is intended for therapeutic purposes.

Methods of Increasing EGFR Degradation

As shown herein for the first time, inhibition of the binding interaction between EGFR and HSP90 leads to an increase in EGFR degradation. Accordingly, the present disclosures further provides a method of increasing EGFR degradation in a cell. The method comprises contacting the cell with a compound of the present disclosures, a pharmaceutically acceptable salt thereof, a conjugate comprising the compound, or a multimer or dimer comprising the compound, in an amount effective to increase the degradation. In some aspects, the cell is part of an in vitro or ex vivo cell culture or in vitro or ex vivo tissue sample. In some aspects, the cell is an in vivo cell. In certain embodiments, the method is intended for research purposes, and, in other embodiments, the method is intended for therapeutic purposes.

Methods of Treating Cancer

As shown herein for the first time, a compound that inhibits a binding interaction between EGFR and HSP90 increases tumor cell death. Thus, the present disclosures provides a method of increasing tumor cell death in a subject. The method comprises administering to the subject a compound of the present disclosures, a pharmaceutically acceptable salt thereof, a conjugate comprising the compound, or a multimer or dimer comprising the compound, in an amount effective to increase tumor cell death.

In accordance with the foregoing, the present disclosures further provides a method of treating a cancer in a subject. The method comprises administering to the subject a compound of the present disclosures, a pharmaceutically acceptable salt thereof, a conjugate comprising the compound, or a multimer or dimer comprising the compound, in an amount effective to treat the cancer in the subject.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating cancer of the present disclosures can provide any amount or any level of treatment of cancer. Furthermore, the treatment provided by the method of the present disclosures may include treatment of one or more conditions or symptoms of the cancer, being treated. Also, the treatment provided by the methods of the present disclosures may encompass slowing the progression of the cancer. For example, the methods can treat cancer by virtue of reducing tumor or cancer growth, reducing angiogenesis, reducing metastasis of tumor cells, increasing cell death of tumor or cancer cells, and the like.

Methods of Sensitizing Tumors

The present disclosures furthermore provides a method of sensitizing a tumor to chemotherapy, radiation therapy, or both chemotherapy and radiation therapy, in a subject. The method comprises administering to the subject a compound of the present disclosures, a pharmaceutically acceptable salt thereof, a conjugate comprising the compound, or a multimer or dimer comprising the compound, in an amount effective to sensitize the tumor to the therapy. As used herein, the term "sensitize" refers to rendering the tumor more treatable by the therapy, such that the therapy achieves a greater therapeutic index or efficacy. In some aspects, the chemotherapy comprises any of the chemotherapeutics described herein, including, but not limited to, a platinum coordination compound (e.g., cisplatin), topoisomerase inhibitor (e.g., camptothecin), antibiotic compound (e.g., doxorubicin, mitomycin, bleomycin, daunorubicin, streptozocin), an antimitotic alkaloid (e.g., vinblastine, vincristine, videsine, Taxol, vinorelbine), or an anti-viral (e.g., gemcitabine). In some aspects, the radiation therapy is any of those described herein.

In some embodiments, the compound of the present disclosures, a pharmaceutically acceptable salt thereof, a conjugate comprising the compound, or a multimer or dimer comprising the compound, is administered to the subject simultaneously with the chemotherapy and/or radiation therapy. In some embodiments, the compound of the present disclosures, a pharmaceutically acceptable salt thereof, a conjugate comprising the compound, or a multimer or dimer comprising the compound, is administered to the subject before the chemotherapy and/or radiation therapy. In particular aspects, the time of administration of the compound of the present disclosures, a pharmaceutically acceptable salt thereof, a conjugate comprising the compound, or a multimer or dimer comprising the compound, and the time of administration of the chemotherapy and/or radiation therapy are about 1 week or less apart, e.g., about 6 days or less apart, about 5 days or less apart, about 4 days or less apart, about 3 days or less apart, about 48 hours or less apart, about 24 hours or less apart, about 12 hours or less apart, about 8 hours or less apart, about 6 hours or less apart, about 4 hours or less apart, about 3 hours or less apart, about 2 hours or less apart, about 1 hour or less apart, about 45 minutes or less apart, about 30 minutes or less apart, about 15 minutes or less apart.

Cancer

The cancer treatable by the methods disclosed herein may be any cancer, e.g., any malignant growth or tumor caused by abnormal and uncontrolled cell division that may spread to other parts of the body through the lymphatic system or the blood stream. In some embodiments, the cancer is a cancer in which an EGFR and an HSP90 are expressed by the cells of the cancer. In some aspects, the cancer is a cancer in which an EGFR protein is over-expressed, the gene encoding EGFR is amplified, and/or an EGFR mutant protein (e.g., truncated EGFR, point-mutated EGFR) is expressed. In some aspects, the cancer is a cancer in which a k-Ras protein is overexpressed, a gene encoding the k-Ras protein is amplified, and/or a k-Ras mutant protein (truncated k-Ras, point-mutated k-Ras) is expressed.

The cancer in some aspects is one selected from the group consisting of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma.

Subjects

In some embodiments of the present disclosures, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human. In some aspects, the human is an adult aged 18 years or older. In some aspects, the human is a child aged 17 years or less.

Kits

In some embodiments, the composition comprising a compound of the present disclosures, a pharmaceutically acceptable salt thereof, a conjugate comprising the compound, or a multimer or dimer comprising the compound, is provided as a kit or package or unit dose. "Unit dose" is a discrete amount of a therapeutic composition dispersed in a suitable carrier. Accordingly, provided herein are kits comprising a compound of the present disclosures, a pharmaceutically acceptable salt thereof, a conjugate comprising the compound, or a multimer or dimer comprising the compound.

In some embodiments, the components of the kit/unit dose are packaged with instructions for administration to a patient. In some embodiments, the kit comprises one or more devices for administration to a patient, e.g., a needle and syringe, a dropper, a measuring spoon or cup or like device, an inhaler, and the like. In some aspects, the compound of the present disclosures, a pharmaceutically acceptable salt thereof, a conjugate comprising the compound, or a multimer or dimer comprising the compound, is pre-packaged in a ready to use form, e.g., a syringe, an intravenous bag, an inhaler, a tablet, capsule, etc. In some aspects, the kit further comprises other therapeutic or diagnostic agents or pharmaceutically acceptable carriers (e.g., solvents, buffers, diluents, etc.), including any of those described herein. In particular aspects, the kit comprises a compound of the present disclosures, a pharmaceutically acceptable salt thereof, a conjugate comprising the compound, or a multimer or dimer comprising the compound, along with an agent, e.g., a therapeutic agent, used in chemotherapy or radiation therapy.

The following examples are given merely to illustrate the present invention and not in any way to limit its scope.

EXAMPLES

Example 1

The following materials and methods were used in the studies described in Example 2.

Materials

Geldanamycin (GA) was acquired from Assay Designs. EGFR (sc-03) antibody was acquired from Santa Cruz Biotechnology. Antibodies for glyceraldehyde-3-phosphate dehydrogenase (GAPDH), HSP70, cleaved PARP, and LC3B were purchased from Cell Signaling Technology, whereas, antibodies to detect ErbB2 and HSP90 were purchased from Neomarkers and Pharmingen, respectively. Cycloheximide and MG132 were obtained from Sigma. Peptides were synthesized by Peptide 2.0 and American Peptide Company. Peptide transfection reagent chariot was purchased from Active Motif.

Cell Culture

All the cells were purchased from the American Type Culture Collection unless otherwise mentioned. The human head and neck squamous cell carcinoma cell lines UMSCC1, 10B, 11B, 12, 17B, 29, 33 and 74B were kindly provided by T. Carey (University of Michigan, Ann Arbor, Mich.). The lung cancer cell line H1975 was provided by J. Engelman (Massachusetts General Hospital, MA). All cell lines were grown in RPMI 1640 supplemented with 10% cosmic calf serum. For all in vitro experiments, cells were released from flasks using PBS containing 0.01% trypsin and 0.20 mmol/L EDTA, and $6 \times 10^5$ cells were plated onto 100-mm culture dishes two days before any treatment.

Immunoblotting

Cells were scraped into PBS containing a sodium orthovanadate and protease inhibitor mixture (Roche Diagnostic Co). Cells were incubated for 15 min on ice in Laemmli buffer (63 mM Tris-HCl, 2% (w/v) SDS, 10% (v/v) glycerol, and 0.005% (w/v) bromophenol blue) containing 100 mM NaF, 1 mM $Na_3VO_4$, 1 mM phenylmethylsulfonyl fluoride, and 1 µg/ml aprotinin. After sonication, particulate material was removed by centrifugation at 13,000 rpm for 15 min at 4° C. The soluble protein fraction was heated to 95° C. for 5 min, then applied to a 4-12% bis-tris precast gel (Invitrogen) and transferred onto a PVDF membrane. Membranes were incubated for 1 h at room temperature in blocking buffer consisting of 3% BSA and 1% normal goat serum in Tris-buffered saline [137 mM NaCl, 20 mM Tris-HCl (pH 7.6), 0.1% (v/v) Tween 20]. Membranes were subsequently incubated overnight at 4° C. with 1 µg/ml primary antibody in blocking buffer, washed, and incubated for 1 h with horseradish peroxidase-conjugated secondary antibody (Cell Signaling, Danvers, Mass.). After three additional washes in Tris-buffered saline, bound antibody was detected by enhanced chemiluminescence plus reagent (Amersham Biosciences, Piscataway, N.J.). For quantification of relative protein levels, immunoblot films were scanned and analyzed using ImageJ 1.32j software (NIH, Bethesda, Md.). Unless otherwise indicated, the relative protein levels shown represent a comparison to untreated controls.

Immunoprecipitation

Cells were trypsinized, washed twice with 1×PBS, and cell lysates were prepared by incubation for 30 min on ice in fresh lysis buffer [1% Triton X-100, 0.1% sodium dodacyl sulfate, 0.15M sodium chloride, 0.01M sodium phosphate, pH 7.2 1 mmol/L phenylmethylsulfonyl fluoride, 2 µg/mL aprotinin, 0.2 mmol/L sodium orthovanadate, 50 mM sodium fluoride, 2 mM EDTA] containing 20 mM ammonium molybdate. Immunoprecipitation of EGFR and HSP90 was performed as described previously.[34]

Site Directed Mutagenesis of EGFR Constructs and Transfections

A modified site directed mutagenesis protocol was used to create the desired mutations in EGFR. The protocol includes 5' end phosphorylation of the primer using T4 polynucleotide kinase enzyme followed by polymerase chain reaction (PCR) with single primer and DpnI enzyme treatment. Primers for site directed mutagenesis were designed by introducing minimal nucleotide changes in the DNA sequence of EGFR cloned into the N1-EYFP vector (Clontech). Mutations in EGFR were confirmed by the University of Michigan DNA sequencing core facility. UMSCC11B and CHO cells were transiently transfected with the constructs using Lipofectamine (Invitrogen) according to the instructions of the manufacturer.

Clonogenic Cell Survival Assay

Clonogenic assays were performed using standard techniques.[34] The fraction surviving each treatment was normalized to the survival of the control cells. Peptide cell survival curves were fitted using the equation $SF=(C_{50})^m/[(C_{50})^m+C^m]$, where SF is the surviving fraction, C is the peptide concentration, $C_{50}$ is the concentration of peptide that produces a 50% cell survival and m is the slope of the sigmoid curve.

Immunostaining

After slides were deparaffinized in xylene and rehydrated using serial ethanol dilutions, antigen site unmasking was performed by immersing slides in 100 nmol/L citrate buffer for 20 minutes at high pressure and temperature inside a pressure cooker. Slides were then washed in PBS, blocked for 1 hour, and incubated in primary antibody at 4° C. overnight. Slides were then washed again in PBS, incubated in secondary antibody for 1 hour, rewashed, and prepared with a coverslip after a drop of ProLong Gold antifade reagent with 4',6-diamidino-2-phenylindole (Molecular Probes) was added to each sample. Fluorescence images were acquired using a DP70 camera fitted on an Olympus 1X-71 microscope.

Half Life Studies of WT-EGFR and 768-773 EGFR Constructs

CHO cells were transfected with an equal amount of DNA template (1 µg) of WT and 768-773 EGFR constructs. 24 hours post transfection, CHX (50 µg/ml) was added to cells expressing each of these constructs. Cells were harvested at 0, 2 and 6 hours post treatment, and immunoblotting was carried out for EGFR and GAPDH to analyze the relative decrease in EGFR protein levels in the 768-773 construct compared with WT.

GST EGFR-HSP90 Direct Interaction Assay

GST pull-down experiments to detect a physical interaction between EGFR and HSP90 were performed using standard procedures. Briefly, purified GST-EGFR(His672-Ala1210, 90 kDa, 1 µg) fusion protein (Cat #7706, Cell Signaling) was incubated with 50 µl (3.5 mg swelled in deionized water) of glutathione-agarose beads (Cat #G4510, Sigma) equilibrated in 0.5× Superdex buffer (1× Superdex buffer: 25 mM HEPES, pH 7.5, 12.5 mM $MgCl_2$, 10 µM $ZnSO_4$, 150 mM KCl, 20% glycerol, 0.1% Nonidet P-40, and 1 mM EDTA) for 2 hours at 4° C. and then washed three times with 0.5× Superdex buffer. About 200 ng purified HSP90 protein (Cat # SPP-770, Assay Designs) was then added to the washed beads and incubated overnight at 4° C. The beads were washed three times using 0.5 Superdex buffer, boiled in Laemmli buffer, and the bound HSP90-EGFR complex was immunodetected following immunoblotting with HSP90 and EGFR specific antibodies.

Peptide Internalization Assay

The UMSCC1 xenografts were cryopreserved in OCT (Electron Microscopy Sciences). Five µm sections were cut from tissues prepared on days 1 and 3 after peptide treatment. Sections were fixed in cold methanol for 20 min and then were blocked with 1% Bovine Serum Albumin (BSA). The sections were incubated overnight with anti-EGFR antibody (Santa Cruz). After washing, the sections were incubated with anti-rabbit Alexa Fluor 488 (Molecular Probes) and Streptavidin conjugated Alexa Fluor 594 (Molecular Probes). Coverslips were mounted with one drop of Prolong Gold anti-fade reagent with DAPI (4,6-diamidino-2-phenylindole; Molecular Probes) to visualize the nuclei. Fluorescence images were acquired using a DP70 camera fitted on an Olympus 1X-71 microscope.

Peptide Binding Assay

UMSCC1 cells ($1\times10^6$) were scraped in PBS containing protease and phosphatase inhibitors, then frozen and thawed three times using dry ice. Next, supernatant was collected and incubated with 3 or 10 µg/ml of biotinylated peptide for 1 hour at 37° C., followed by the addition of 20 µl of Streptavidin agarose beads (EZview red Streptavidin affinity gel, Sigma). Samples were rotated overnight at 4° C., boiled in 30 µl of Laemmli buffer at 100° C. for 10 minutes, and immunoblotted for HSP90 to detect binding with peptide.

ATP Binding Assay

Cell lysates were prepared in RIPA buffer. About 500 µg protein was incubated overnight at 4° C. with 25 µl of γ-linked ATP-Agarose beads (Innova Biosciences). After centrifugation, beads were washed in PBS 6 times and ATP bound proteins were extracted in Laemilli buffer, resolved on a SDS page and immunoblotted with anti-HSP90 antibody to detect change in ATP bound HSP90 levels.

In Vivo Tumor Growth Studies

Mice were handled according to the established procedures of the University of Michigan Laboratory Animals Maintenance Manual. To generate tumor xenografts, $2\times10^6$ UMSCC1 cells were transplanted into the flanks of athymic nude Foxn1$^{nu}$ mice (Harlan Laboratories). When tumors reached a volume of ~50 $mm^3$, the mice were randomized into 3 groups (1 untreated control and 2 experimental groups for specific and non-specific peptides) containing from 15 to 25 tumors, and treatment was initiated.

Live Cell Imaging to Monitor Autophagy:

Change in LC3 localization upon EGFR degradation after treatment with peptide was monitored in live HeLa cells that were stably expressing LC3B-GFP construct. LC3-I is converted to LC3-II during autophagy, and causes the autophagosomes to appear as punctate spots using a fluorescent microscope. HeLa-LC3-GFP cells were plated in optically clear multi-chamber slides. After overnight incubation with cell permeable peptide, change in LC3 expression was monitored. Chloroquine (8 µM) which stabilizes LC3 autophagosomes, was used as a positive control.

Statistics

Tumor volume doubling was determined for each xenograft by identifying the earliest day on which it was at least twice as large as on the first day of treatment. A cubic smoothing spline was used to obtain the exact time of doubling, and the Kaplan-Meier method was used to analyze the doubling times derived from the smoothed growth curves. The log rank test was used for comparisons between any two treatment groups. Results are presented as mean±SEM, and Student's t test was used to assess the statistical significance of differences. A significance level threshold of $P<0.05$ was used.

Example 2

The following studies were carried out using the materials and methods described Example 1.

EGFR Physically Interacts with HSP90

Figure 2:
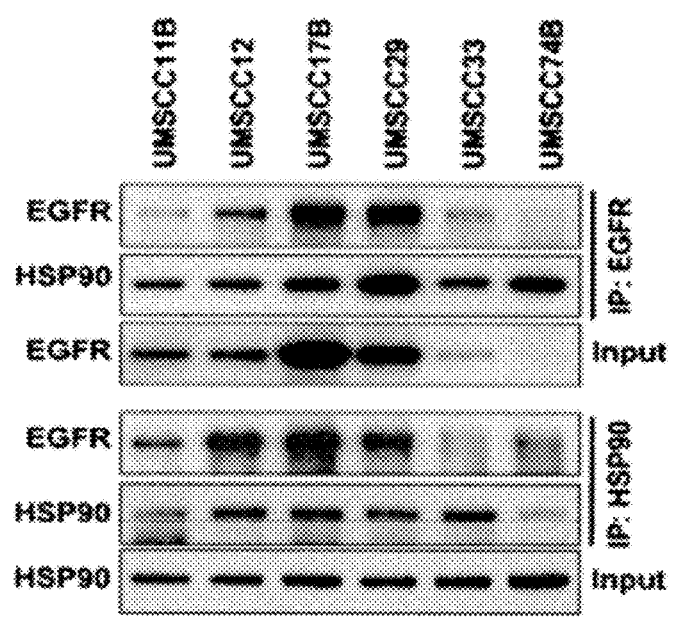
FIG. 2 represents immunoblots that demonstrate the interaction between HSP90 and EGFR. Immunoprecipitation of HSP90 and EGFR was followed by immunoblotting with EGFR and HSP90.

To determine whether EGFR directly interacts with HSP90, 11 cancer and 2 normal cell lines that express different levels of EGFR were selected and immunoprecipitation of HSP90 followed by immunoblotting for EGFR was performed. It was found that EGFR was consistently immunoprecipitated with HSP90 (FIG. 1a, and FIG. 2) although the degree of interaction varied across these lines. This interaction was confirmed by immunoprecipitating EGFR and immunoblotting with HSP90 antibody (FIG. 2). To further confirm EGFR-HSP90 interaction, a FLAG-tagged HSP90 was expressed in UMSCC11B cells, immunoprecipitated FLAG and immunoblotted for EGFR. It was found that ectopically expressed HSP90 also interacted with endogenous EGFR (FIG. 1b). This interaction was reduced upon treatment with geldanamycin (GA), an inhibitor of HSP90 activity. Since both EGFR and HSP90 are known to interact with ErbB2, we next sought to determine whether the EGFR-HSP90 interaction was direct or via ErbB2. When we expressed full length EGFR in CHO cells, which are ErbB2 negative, EGFR was immunoprecipitated using HSP90 antibody (FIG. 1c). Likewise, GST pull-down assays demonstrated a direct physical interaction between EGFR and HSP90 (FIG. 1d). These results show that the EGFR-HSP90 interaction is direct and not mediated by heterodimerization of EGFR with ErbB2.

Identification of a Potential Binding Region of HSP90 on EGFR

Figure 3:
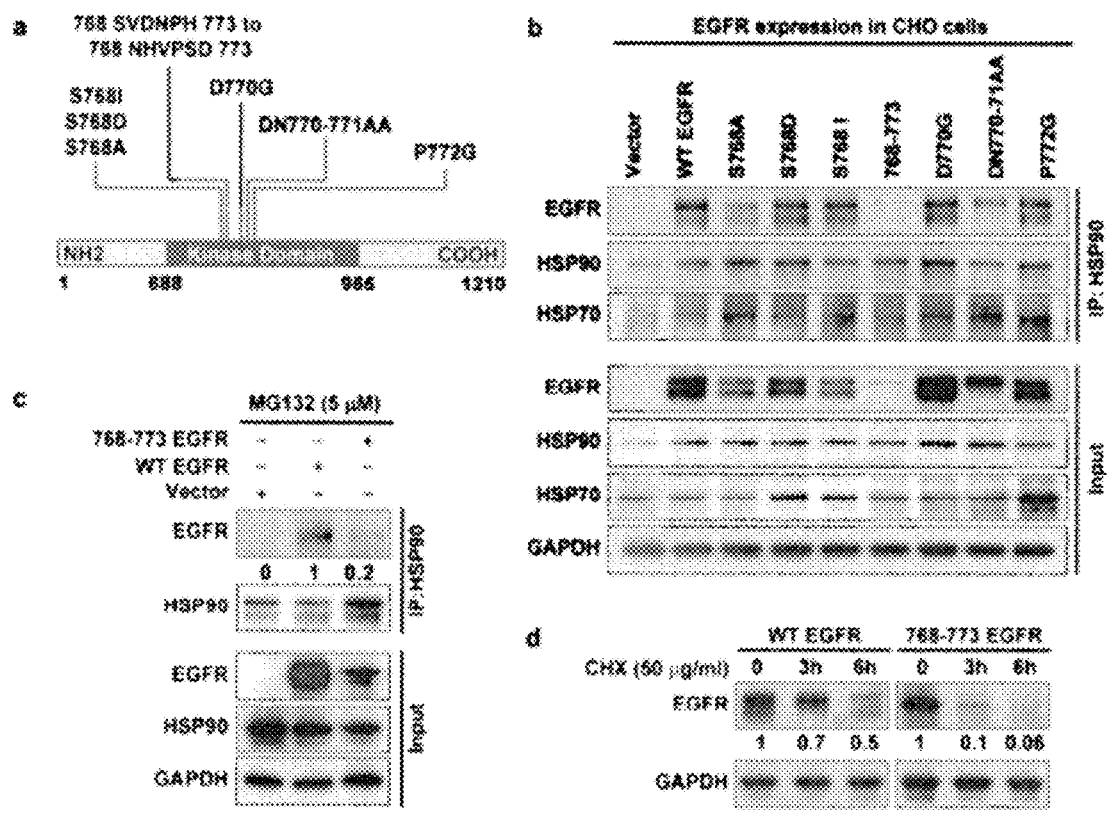
FIG. 3 demonstrates the sequence-dependent interaction between EGFR and HSP90. (a) Diagram of EGFR, showing various mutants around the region comprising amino acids 768-773 (S768A, S768D, S768I, 768 SVDNPH 773 (SEQ ID NO: 15) to 768 NHVPSD 773 (SEQ ID NO: 35), D770G, DN770-771AA, and P772G). (b) All the mutant constructs shown in FIG. 2a along with the vector or WT-EGFR were expressed in CHO cells, followed by immunoprecipitation with HSP90 and then immunoblotting for both EGFR, HSP90 and HSP70 to detect any potential differences in the EGFR-HSP90 interaction as well as EGFR expression. Results indicate that several mutants in 768-773 region in EGFR had a large impact on EGFR stability, which was directly correlated to its interaction with HSP90. (c) To determine whether the cause of reduced protein interaction in the case of 768-773 EGFR was reduced interaction between EGFR and HSP90 or simply reduced expression of EGFR, cells were treated with a proteasome inhibitor, MG132, for 8 hours then HSP90 was immunoprecipitated followed by immunoblotted for EGFR and HSP90. Our data indicate that MG132 treatment restored 768-73 EGFR protein levels (see input); however, the interaction between HSP90 and 768-73 EGFR remained minimal when compared to the WT-EGFR. These results demonstrate that the decrease in 768-773 EGFR-HSP90 interaction is not due simply to lowered expression of 768-773 EGFR. d) We then hypothesized that 768-773 EGFR would be less stable compared to WT EGFR due to its decreased binding with HSP90. Therefore we determined the half-life of each form of EGFR using Cycloheximide treatment (50 μg/ml) and found that 768-773 EGFR is significantly less stable than WT-EGFR.

Because the interaction between ErbB2 and HSP90 involves the kinase domain of ErbB2[16], we hypothesized that the kinase domain of EGFR might also contain the HSP90 binding region. Therefore, we constructed mutants of EGFR based on the binding region of ErbB2 with HSP90[16], expressed them in CHO cells and assessed their interactions with HSP90. We began with a construct with six substitutions in this region (768-773 EGFR; SVDNPH (SEQ ID NO: 15) to NHVPSD (SEQ ID NO: 35)) by scrambling the amino acids from the native sequence. There was almost no interaction between HSP90 and the 768-773 EGFR construct (FIG. 3a). We then constructed mutants with only single and double substitutions (S768A, S768D, S768I, D770G, DN770-771AA, and P772G). Immunoprecipitation of HSP90 revealed that S768D and S768I, D770G and P772G -EGFR had a similar interaction with HSP90 as WT-EGFR. We found a decrease in interaction with HSP90 in the S768A-EGFR expressing cells. The interaction was slightly decreased in the case of the double mutant DN770-771AA (FIG. 3b). These results demonstrate that the interaction between EGFR and HSP90 does not depend on a single amino acid but on the 6 amino acids from 768 to 773.

As we expected HSP90 to stabilize EGFR, we anticipated that EGFR expression would correlate with HSP90 binding. Indeed, the two constructs S768A and DN770-771AA were expressed in lower amounts compared to the WT-EGFR, whereas the 768-773 EGFR construct that shows minimum interaction with HSP90 was expressed at significantly lower levels than either single or double EGFR mutants. However, we needed to rule out the possibility that this finding was due to the decreased expression of EGFR. We hypothesized that if decreased EGFR levels in cells transfected with the 768-773 EGFR construct were due to a decrease in its interaction with HSP90, then restoration of EGFR levels by inhibiting degradation would not restore the EGFR-HSP90 interaction. We expressed the 768-773 EGFR and WT-EGFR construct in CHO cells, treated cells with a proteasomal inhibitor MG132 (5 µM)) for 8 hours, and assessed whether restoration of EGFR levels via blockade of protein degradation caused any change in the EGFR-HSP90 interaction. We found that MG132 pretreatment caused a significant increase in 768-773 EGFR levels (FIG. 3c), but that the interaction of expressed 768-773 EGFR with HSP90 still remained low when compared to the WT-EGFR. To further test our hypothesis that 768-773 EGFR might be vulnerable to degradation due to its decreased binding with HSP90, we expressed the WT and 768-773 EGFR constructs in CHO cells and treated with cycloheximide (CHX, 50 µg/ml) to block protein synthesis. EGFR levels were reduced by 30% in WT-EGFR expressing cells at 3 hours and by 50% at 6 hours. However, levels of 768-773 EGFR were reduced by about 90% within 3 hours, showing that 768-773 EGFR is a significantly less stable protein than WT-EGFR (FIG. 3d). These results demonstrate that the decrease in 768-773 EGFR-HSP90 interaction is not due simply to lowered expression of 768-773 EGFR.

Specificity and Efficacy of EGFR-HSP90 Interaction Inhibitory Peptide

We next sought to target EGFR for degradation by use of peptides that would competitively inhibit EGFR-HSP90 binding. We also focused on a larger region of 21 amino acids, considering residues flanking the 768-773 site (Table 1).

TABLE I

Effect of synthetic peptides on clonogenic survival of UMSCC1 cells:

| Peptide | Sequence | Survival Fraction |
|---|---|---|
| 1 | DEAYVMA | 0.93 ± 0.1 |
| 2 | SVDNPHVC | 0.77 ± 0.12 |
| 3 | RLLGIC | 0.85 ± 0.16 |
| 4 | GVGSPYVS | 1 ± 0.16 |
| 5 | DEAYVMASVDNPHVCRLLGIC | 1 ± 0.14 |
| 6 | DEAYVMAGVGSPYVSRLLGIC | 1 ± 0.12 |
| 7 | SVGNPHVC | 0.97 ± 0.21 |
| 8 | NHVPSDVC | 1 ± 0.1 |

We treated UMSCC1 cells with these peptides using Chariot (a peptide delivery agent from Active Motif, Carlsbad, Calif.) and assessed EGFR degradation (data not shown). We found that peptides 2 and 3, which are directed at the 768-773 of EGFR, caused a decrease in cell survival (Table 1), confirming the importance of this domain for EGFR-HSP90 interaction.

We selected peptide #2 (named "Disruptin") and the scrambled peptide (peptide #8) as a control for further studies. These two peptides were synthesized along with 11 amino acids selected from the HIV-TAT gene to enable cellular uptake, and a biotin moiety was attached for molecular studies[17,18] (Table 1b).

TABLE II

Design and sequence of cell permeable peptides and their effects on clonogenic survival in different cancer and normal cell lines.

a

| Specific Peptide | Biotin-YGRKKRRORRR-SVDNPHVC |
|---|---|
| Non Specific Peptide | Biotin-YGRKKRRORRR-NHVPSDVC | b
Human Cancer

| | H&N | | | Lung | |
|---|---|---|---|---|---|
| | UMSCC1 WT-EGFR | UMSCC10B WT-EGFR | UMSCC74B WT-EGFR | A549 WT-EGFR | H1975 T790M-EGFR |
| Specific | 0.76 ± 0.02 | 0.63 ± 0.06 | 0.74 ± 0.15 | 0.57 ± 0.11 | 0.40 ± 0.08 |
| Non Specific | 1.62 ± 0.04 | 0.98 ± 0.04 | 0.88 ± 0.10 | 0.81 ± 0.09 | 0.77 ± 0.17 | b

| | Human | | | | Hamster |
|---|---|---|---|---|---|
| | Cancer | | Normal | | |
| | Lung H3255 L858R-EGFR | Cervical HeLa WT-EGFR | Epithelial Het1A WT-EGFR | Fibroblasts MRC5 WT-EGFR | Ovarian CHO EGFR |
| Specific | 0.71 ± 0.05 | 0.72 ± 0.05 | 1.02 ± 0.03 | 1.01 ± 0.04 | 0.98 ± 0.02 |
| Non Specific | 1.0 ± 0.07 | 0.92 ± 0.08 | 0.91 ± 0.11 | 1.04 ± 0.05 | 1.12 ± 0.14 |

Figure 4:
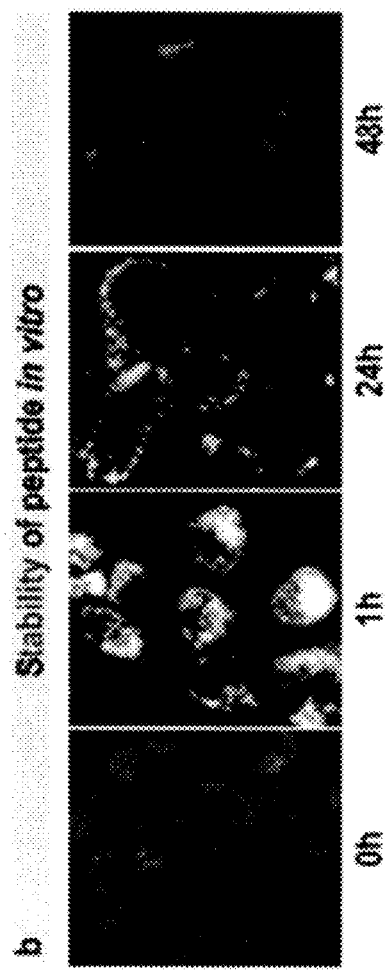
FIG. 4 demonstrates the penetration and stability of cell permeable peptides in cultured cells. Biotinylated peptide fused with the HIV-TAT sequence was designed from FIG. 3a. (a) UMSCC1 cells were incubated with 100 μg/ml biotinylated HIV-TAT conjugated peptide for 1 h. Cells were washed, fixed and then incubated with Streptavidin-Alexa Fluor 562 reagent to visualize the internalized peptide using a fluorescence microscope. (b) Stability of the peptide was assessed by fixing cells at different times after treatment as visualized as described above.
Figure 4:
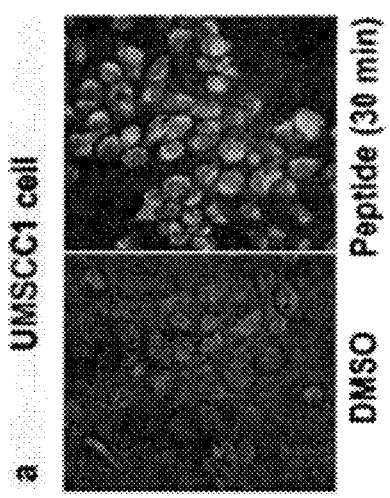

Uptake and binding studies revealed that the peptides were stable for up to 24 hours (FIG. 4). We then assessed colonogenic survival in head and neck (UMSCC1, UMSCC10B, UMSCC74B), lung (A549, H1975, H3255), and HeLa cancer cells. Normal human esophageal squamous epithelial (Het1A) and lung fibroblast (MRC5) cell lines along with EGFR negative CHO cells were selected to study selectivity. The EGFR specific peptide reduced the surviving fraction of the cancer cell lines containing WT-EGFR, including UMSCC1 (0.76±0.02), UMSCC10B (0.63±0.06), UMSCC74B (0.74±0.15) HeLa (0.72±0.05), and A549 (0.57±0.11), as well as in H1975, which contains the T790M mutation and is resistant to erlotinib, (0.40±0.08) and H3255 (containing the L858R EGFR mutation and is sensitive to erlotinib, 0.71±0.05) (Table 2b). The peptide did not affect the normal cell lines.

Figure 5:
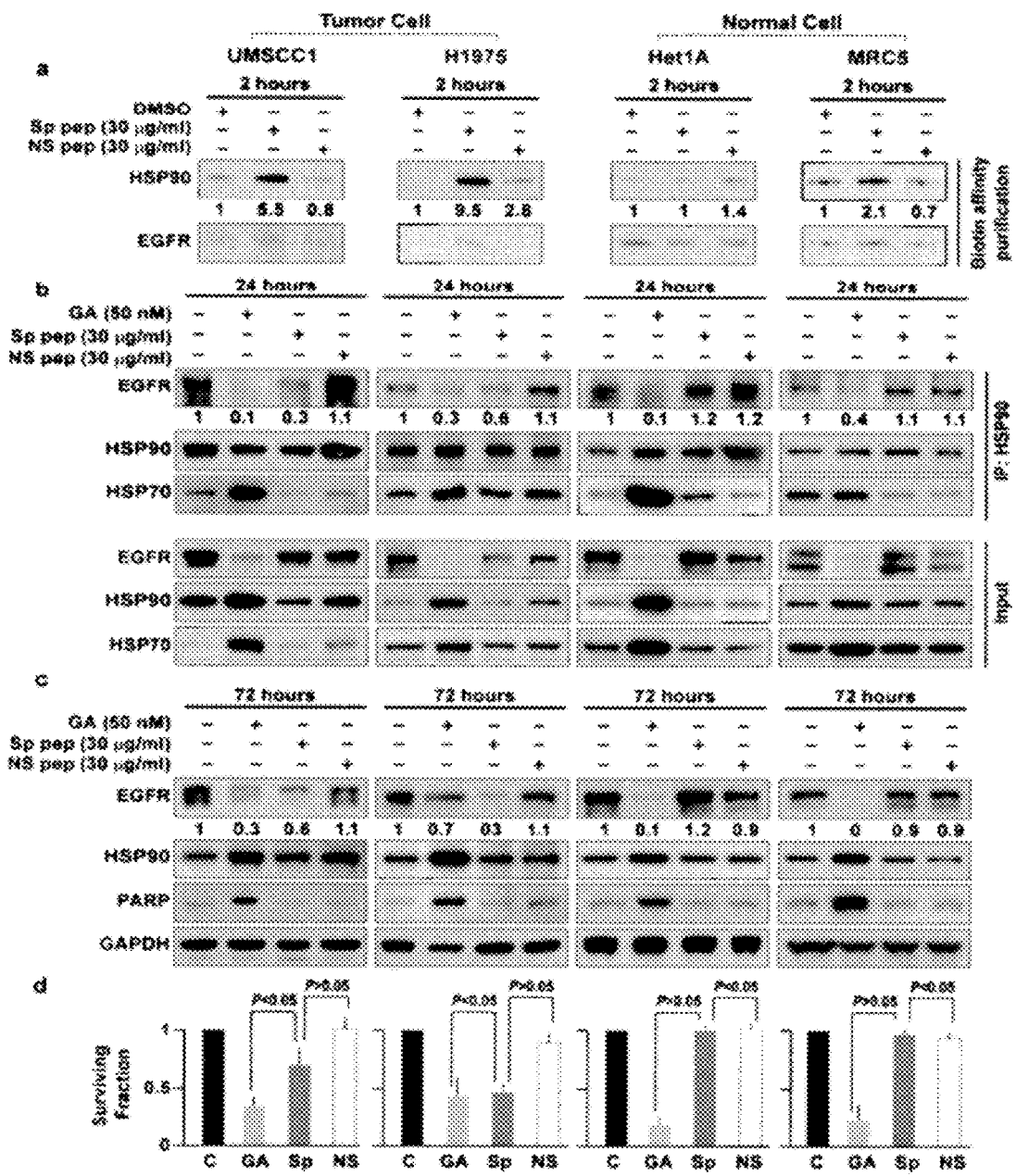
FIG. 5 demonstrates the molecular interaction of peptides with HSP90 and effects on EGFR-HSP90 interaction, EGFR degradation and cell survival. (a) To determine if the lead peptide interacts directly with tumor HSP90, cell lysates from cancer or normal cells were prepared by 3 freeze-thaw cycles and then incubated with 3 μg/ml of specific or non-specific biotin coupled peptides for 2 hours. The peptide was affinity purified using Streptavidin-agarose beads, and bound HSP90 was detected by immunoblotting for HSP90. Result suggests that specific peptide has greater affinity for tumor HSP90 compared to HSP90 from normal cells, and that this interaction with EGFR was minimal. (b) The effect of the treatment with specific and non-specific peptide on HSP90-EGFR interaction was determined by IP of HSP90 followed by IB with EGFR at 24 hours post treatment. Result show that treatment with specific peptide reduced HSP90-EGFR interaction in UMSCC1 and H1975 cells but had no effect on normal cells as assessed by densitometric analysis and expressed relative to untreated control. Geldanamycin (GA, an HSP90 inhibitor used as a positive control), induced degradation of EGFR in all cell lines treated (see input) and also reduced the level of interaction between EGFR and HSP90. The increased levels of HSP70 upon GA treatment indicate inhibition of HSP90 activity. (c) Specificity of the peptide treatment compared to GA was evaluated in tumor and normal cells as described in FIG. 3b, by assessing the levels of EGFR and PARP cleavage (marker of apoptotic cell death) at 72 hours post treatment, (d) cell survival was assessed using colony formation assay.
Figure 6:
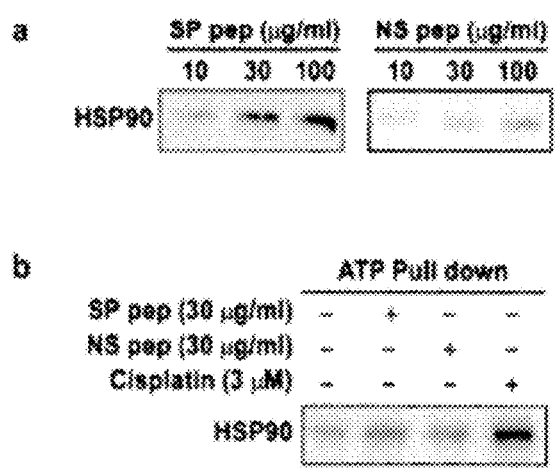
FIG. 6 demonstrates the effect of peptide concentration on HSP90 binding and effect on HSP90's ability to bind with ATP. (a) UMSCC1 cell lysate was incubated with three concentrations of specific or non-specific peptide (10, 30 and 100 μg/ml) followed by immunoblotting with anti-HSP90 antibody. Result shows that the amount of HSP90 pull-downed was proportional to an increase in the concentration of specific peptide. The non-specific peptide showed minimal interaction with HSP90. (b) The effect of EGFR specific peptide on HSP90's ability to bind with ATP was assessed. Cisplatin treatment which is known to activate HSP90 which enhances HSP90 binding with ATP was used as a positive control. Three days after treatment cell lysate was incubated with ATP-Sepharose beads to pull down active HSP90 protein. Bound protein was eluted in SDS-PAGE buffer, and the levels were determined by immunoblot analysis. Peptide treatment had no effect on HSP90's ability to bind with ATP.

The specific peptide directly interacts with HSP90 and disrupts the EGFR-HSP90 interaction To determine whether the EGFR specific peptide directly interacts with HSP90, we carried out affinity purification of the biotinylated-peptides in two cancer (UMSCC1, H1975) and two normal cell lines (Het1A and MRC5). HSP90 protein binding was increased (5 to 10 fold) only with the EGFR specific peptide in cancer cells but not in the normal cells (FIG. 5a). We also found a concentration-dependent increase in the binding of the specific peptide with HSP90 (FIG. 6a). Next, we sought to determine whether the specific peptide disrupted EGFR-HSP90 interactions in tumor cells relative to normal cells. The HSP90 inhibitor geldanamycin (GA) (50 nM), was used as positive control. After a 24-hour exposure to specific peptide, EGFR-HSP90 interaction was significantly reduced in the cancer cell lines, which was comparable with GA treatment, but there was no effect in response to the non-specific peptide in the tumor cells or specific peptide in normal cells (FIG. 5b). Peptide treatment affected neither HSP90 activity as assessed by HSP90 and ATP binding in UMSCC1 cells (FIG. 6b), nor the levels of either HSP90 or HSP70, both of which were elevated by the HSP90 ATPase inhibitor GA (FIG. 5b). We subsequently observed a loss of EGFR protein (FIG. 5c) and clonogenic survival (FIG. 5d and Table II) in tumor cells at 72 h post treatment. These findings demonstrate that the specific peptide binds with HSP90, disrupts EGFR-HSP90 interaction, decreases EGFR stability of both wild type and erlotinib resistant T790M-EGFR, and decreases clonogenic survival, recapitulating the effect of 768-773 mutation on EGFR.

Effects of the Specific Peptide on EGFR Levels in Human Xenografts

Figure 7:
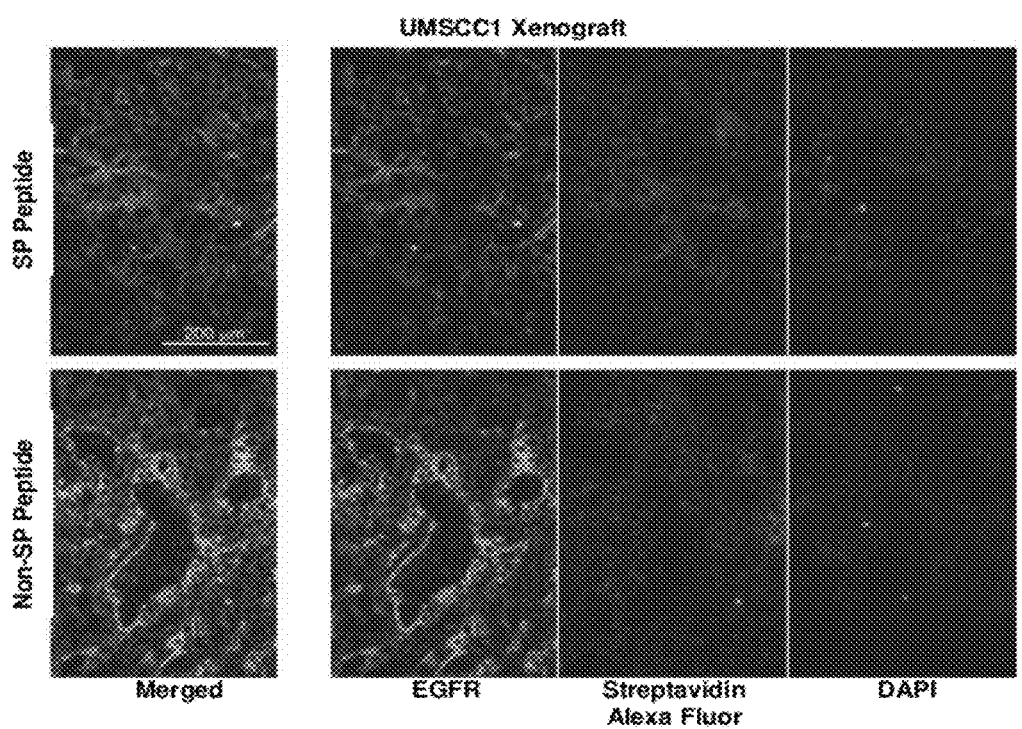
FIG. 7 demonstrates the delivery, detection and effects of cell permeable peptides in UMSCC1 xenografts. Delivery of the peptide to the UMSCC1 xenografts was assessed after injection of peptides (8 mg/kg, i.p.), 3 days later the tumors were removed, cryosections were immunostained for EGFR, and the internalized biotinylated peptide was visualized by Streptavidin Alexa Fluor 562 reagent. The tumors from the mice treated with the specific peptide, showed reduced levels of EGFR in the areas positive for the peptide as detected by the Streptavidin Alexa Fluor 562 reagent.
Figure 8A:
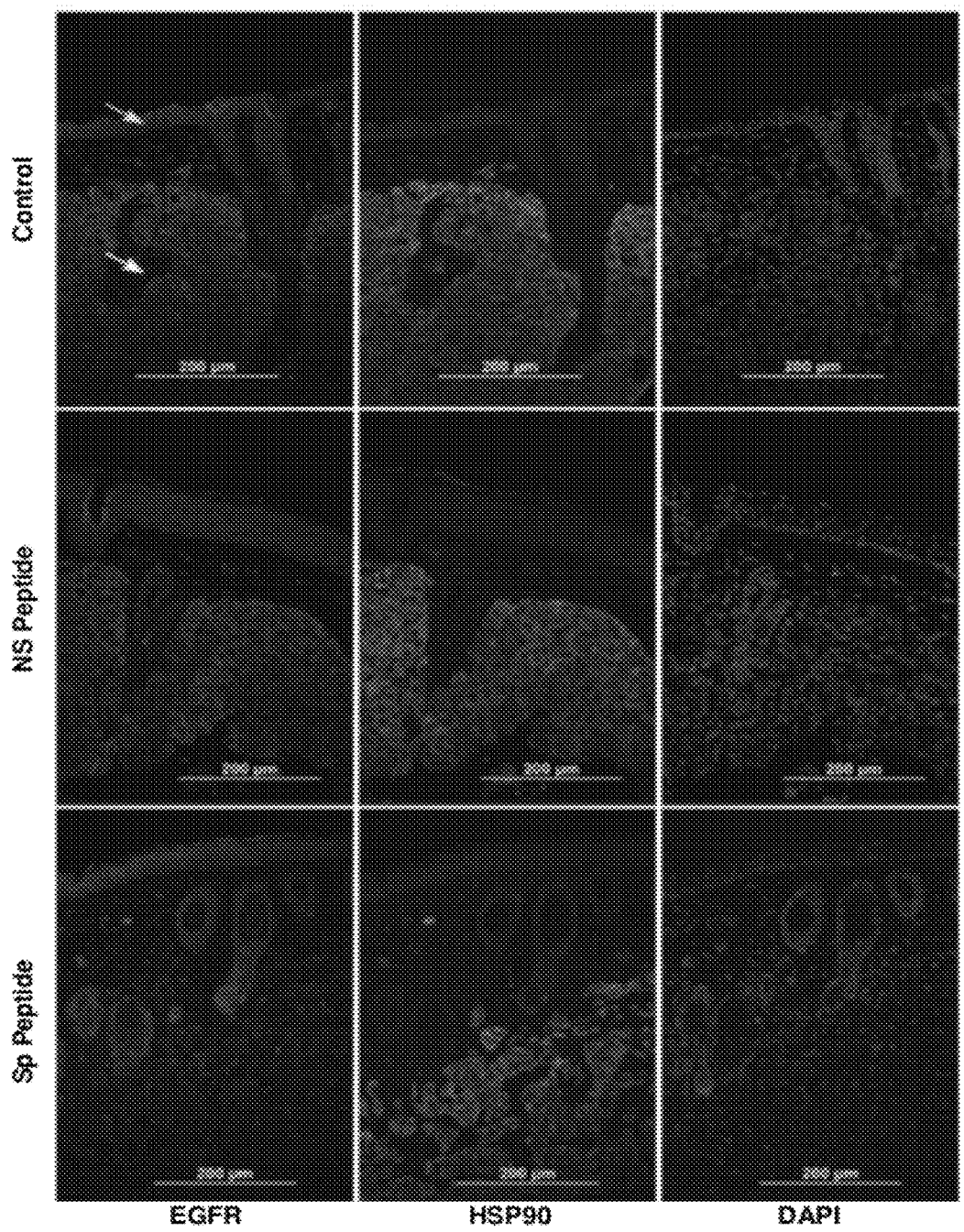
FIG. 8 demonstrates the efficacy and specificity of peptide treatment on HSP90 and EGFR levels in tumor and adjacent normal tissue. (a) To determine if EGFR level was affected in the UMSCC1 xenograft tumor, mice were injected with either DMSO, specific, or non-specific biotinylated peptide (8 mg/kg) intraperitoneally. Three weeks after the injection, tumors (white arrow) along with some adjacent normal tissue (yellow arrow) were harvested. Immunostaining was performed for EGFR and HSP90. HSP90 levels were not affected by either treatment either in tumor or in the adjacent skin tissue. EGFR expression was reduced in the tumor treated with specific peptide relative to normal adjacent skin cells. (b) The effect on tumor growth was also assessed after treatment with two injections separated by 3 days. Tumor volume was recorded every other day during this period, (c) Time to tumor volume doubling was plotted for each treatment condition using Kaplan-Meier method and (d) Comparisons between any two treatment groups was analyzed by log rank tests.
Figure 8:
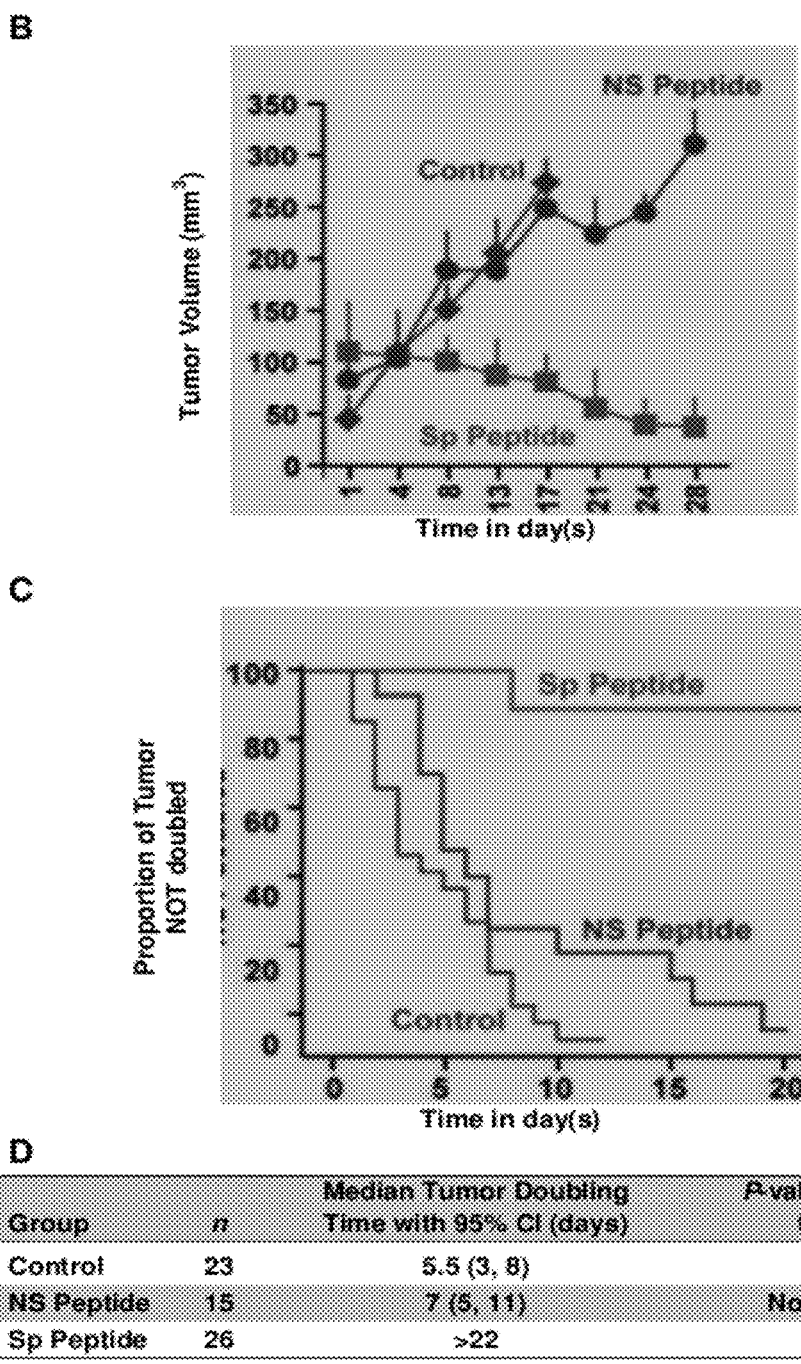

To determine the effects of the specific peptide on EGFR levels in vivo, we injected these peptides into nude mice bearing established UMSCC1 xenografts. We found that specific peptides were detectable in xenografts as early as one day and remained detectable 72 hours post injection (FIG. 7) and caused a reduction in EGFR immunostaining. To determine the specificity and long term effects of the EGFR specific peptide, we harvested tumors along with normal adjacent tissue on day 18 post treatment. EGFR, but not HSP90, staining was decreased in sections from the tumor xenografts of specific-peptide treated mice, but was unchanged in the adjacent normal tissue (FIG. 8a). These results suggest that although the EGFR kinase domain is 100% conserved between mouse and human, the peptide preferentially targets EGFR in the tumor cells and does not seem to affect EGFR in the normal cells.

Tumor lysates were also analyzed for the levels of EGFR, HER2, HER3, pERK, tERK, HSP90 and GAPDH. Disruptin treatment caused a marked reduction in EGFR and pERK levels, whereas, HER2, HER3 levels were largely unaffected.

Figure 9:
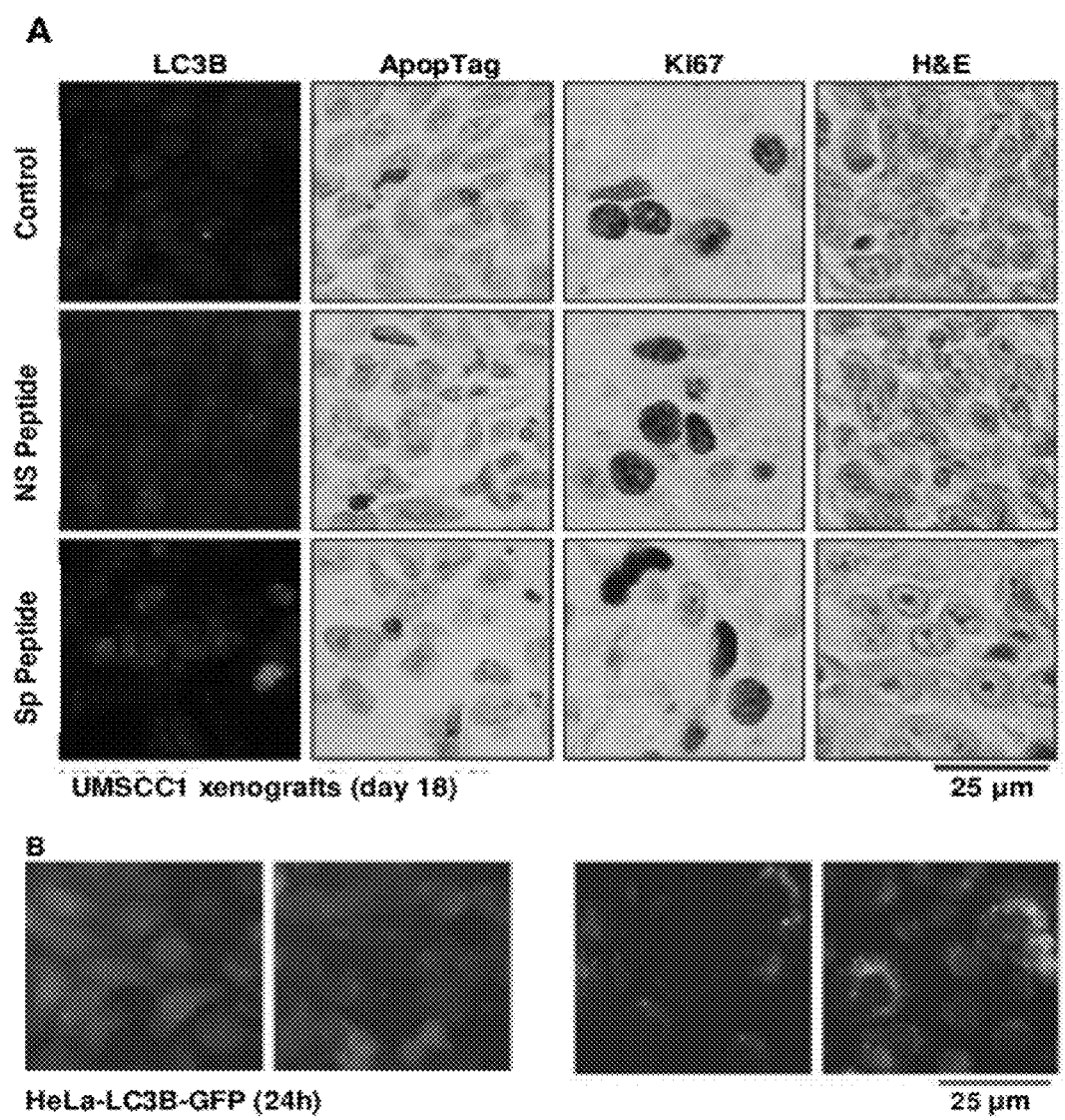
FIG. 9 demonstrates the effect of peptide treatment on tumor cell proliferation and cell death. (a) 18 days post treatment tumors were harvested and immunostained to assess the mechanism of tumor response using either ApopTag (apoptosis), LC3B (autophagy) and ki67 (cell proliferation). A representative field for H&E staining from each group is also included. There was no difference in either apoptosis or cell proliferation; however, the specific peptide treated tumor showed an increase in the punctate staining of LC3B, indicating activation of autophagy pathway. (b) These results were confirmed in HeLa-LC3B-GFP cells, grown in culture, where chloroquine was used as a positive control.
Figure 10:
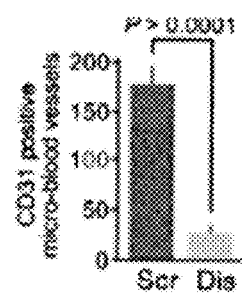
FIG. 10 demonstrates the effect of peptide treatment on micro-blood vessel density.

We then assessed the effect of the peptides on tumor growth in UMSCC1 xenografts (FIGS. 8b and c). A single dose of specific peptide significantly increased median tumor doubling time (16 days) compared with both mock treated and non-specific peptide treated mice (5.5 days) (P=0.0002) (data not shown). The administration of two injections of the peptide (3 days apart) significantly increased median tumor doubling time (>22 days) compared with the mock-treated group (5.5 days) (P<0.0001) (FIG. 8d). No systemic toxicity was observed. We found that there was no difference between any of the treatment groups in either Ki67 or ApopTag staining 18 days after treatment (FIG. 9a), suggesting that the tumor response was independent of cell proliferation or apoptosis. We then stained these samples with LC3B antibody, which is a marker for autophagic death. We found an increase in LC3B punctate staining in tumors that were treated with specific peptide compared to either non-specific peptide or DMSO treated control. These findings were further confirmed in cultured HeLa cells that stably express LC3B-GFP fusion protein (FIG. 9b), suggesting that the response is due to an induction of autophagy. The effect of Disruptin treatment on micro-blood vessel density in the samples was analyzed by CD31 immunostaining and is shown in FIG. 10.

Figure 11:
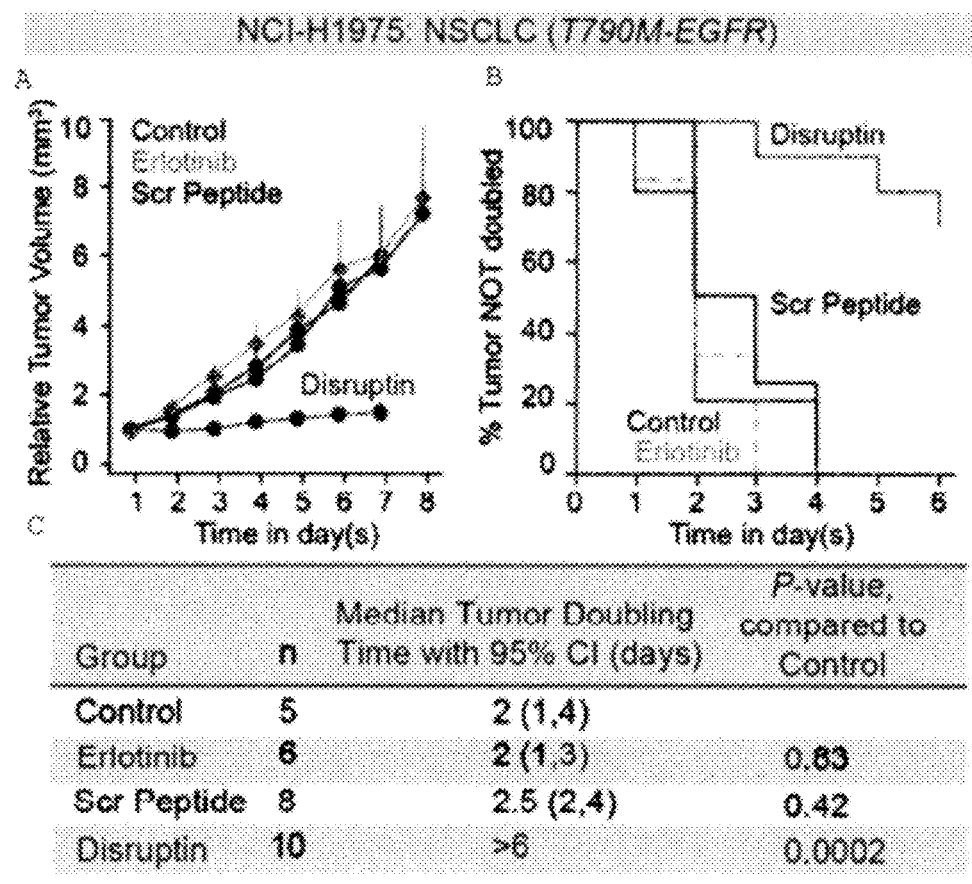
FIG. 11(a-c) shows the efficacy of peptide treatment in NCI-H1975 xenografts.

The effect of Disruptin on tumor growth in NCI-H1975 xenografts was also assessed in comparison to erlotinib. To generate tumor xenografts, $2 \times 10^6$ NCI-H1975 cells were transplanted into the flanks of athymic nude Foxn1$^{nu}$ mice (Harlan Laboratories). When tumors reached a volume of about 50 mm$^3$, the mice were randomed into treatment groups and Disruptin treatment as described for the UMSCC1 xenograft mice above was initiated except that the NCI-H1975 bearing animals were also treated daily with erlotinib (100 mg/kg, p.o., one week). As shown in FIG. 11a-c, Disruptin also increased tumor doubling time in the NCI-H1975 bearing animals.

Example 3

To assess the efficacy of a peptide of the present disclosures against tumors expressing either wild-type or erlotinib-resistant EGFR, grown as xenografts, four different cell lines that contain either WT or mutant EGFR are implanted into the mice of a treatment group (10 mice per group) to produce xenografts. A total of 160 mice are used (4 cell lines×4 treatment groups×10 mice per group). Each mouse is prepared with two tumors. Once the tumor has reached about 100 mm$^3$, mice are randomized into 4 groups containing at least 10 animals per group. Mice are then given (a) specific peptide (8 mg/kg, ip, day 1 and 3) (b) non-specific peptide (same as specific peptide), (c) erlotinib (80 mg/kg, oral, 5 doses), (d) DMSO (same as specific peptide). Three mice are sacrificed to take out 6 tumors on day 3 and 6 tumors on day 18 to assess the effect on EGFR-HSP90 interaction by immunoprecipitation and on EGFR degradation by immunoblotting and immunofluorescence analysis of EGFR and key down-stream signaling molecules, such as pAKT, pERK1/2 (as described previously (Nyati et al., Clin Cancer Res 10: 691-700 (2004)). The effect of treatment on apoptosis and cell proliferation are assessed by TUNEL and Ki-67 staining. The remaining tumors are monitored for growth for 60 days or until tumors have reached a maximum of 1 cm×1 cm.

The median growth rate or time to doubling for each cell line in each treatment is determined. Linear contrasts are used to test the effect of treatment on growth rates overall, and within cell line types. Cox proportional hazards regression models are utilized to test for differences in doubling times while allowing inclusion of data from tumors removed on days 3 and 18 (censored if volume not doubled at time of removal). Treatment, cell line and their interaction are included as covariates. An overall comparison between two treatment groups is obtained by stratifying the analysis on cell line. Pairwise comparisons of particular interest include peptide vs. control, peptide+cisplatin vs. cisplatin and peptide+cisplatin vs. peptide.

Example 4

To assess the efficacy and mechanism of EGFR degradation induced by treatment with a compound of the present disclosures, and the role of this treatment in chemo and radiosensitivity, two cell lines from Example 3 are selected: one that expresses WT-EGFR and second that expresses T790M-EGFR for combination studies. Mice are prepared as described in Example 3 and are given a combination treatment wherein either a control peptide or a peptide compound of the present disclosures are administered followed by a single dose of cisplatin (5 mg/kg), or 5 radiation treatments (i.e. Mon-Fri, 2Gy per fraction). In this experiment, each group will contain at least 10 mice per group and 180 mice in total are used (2 cell lines×9 treatment groups×10 mice per group). Three mice are sacrificed on days 3 and 18 to assess the effect on EGFR-HSP90 interaction by immunoblotting, immunoprecipitation and by immunofluorescence analysis as described in Example 3. The remaining tumors are monitored for growth for 60 days or until tumors have reached a maximum of 1 cm×1 cm.

The median growth rate or time to doubling for each cell line in each treatment is determined. Linear contrasts are used to test the effect of treatment on growth rates overall, and within cell line types. Cox proportional hazards regression models are utilized to test for differences in doubling times while allowing inclusion of data from tumors removed on days 3 and 18 (censored if volume not doubled at time of removal). Treatment, cell line and their interaction are included as covariates. An overall comparison between two treatment groups is obtained by stratifying the analysis on cell line. Pairwise comparisons of particular interest include peptide vs. control, peptide+cisplatin vs. cisplatin and peptide+cisplatin vs. peptide.

Example 5

The safety of Disruptin compared to geldanamycin in immune-competent C57BL/6 mice was investigated.

Mice were dosed by intraperitoneal injection with 10 and 30 mg/kg of Disruptin, and brain, lung, liver, heart, kidneys, spleen, stomach, small intestine, mesenteric lymph nodes, cecum, colon, pancreas, ovaries, bone marrow, and eyes were evaluated 3 days post-injection. There were no histological alterations in the evaluated organs after treatment with Disruptin or the scrambled peptide at either dose tested. In contrast, mice treated with geldanamycin showed histological evidence of toxicity in eye and liver. Complete blood counts and liver cytosolic enzymes (AST, ALT) were not significantly different from controls in the Disruptin and scrambled peptide treated mice at either dose. These results suggest that Disruptin, at an effective dose, was well-tolerated and lacked the adverse effects seen in geldanamycin treated mice.

Example 6

The effect of Disruptin (peptide #2) on capillary sprouting was assessed in human dermal microvascular cells.

Figure 12:
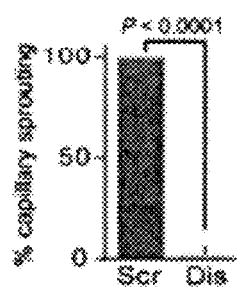
FIG. 12 shows the effect of peptide treatment on capillary sprouting.

The cells were seeded in 24-well plates coated with growth factor reduced Matrigel (BD Biosciences, Bedford, Mass., USA). The wells were then treated on day 1 with the scrambled peptide (peptide #8) and Disruptin (100 µg/ml). Three days after treatment, the capillary branches were counted and analyzed. It was found that network had degenerated in the Disruptin-treated wells. Cell death was assessed by Propidium Iodide staining. FIG. 12 shows the reduced percentage of capillary sprouting in Disruptin-treated wells as compared to the scrambled peptide-treated wells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Nyati, M. K., Morgan, M. A., Feng, F. Y. & Lawrence, T. S. Integration of EGFR inhibitors with radiochemotherapy. *Nature reviews* 6, 876-885 (2006).
2. Weihua, Z., et al. Survival of cancer cells is maintained by EGFR independent of its kinase activity. *Cancer cell* 13, 385-393 (2008).
3. Chun, P. Y., et al. Synergistic effects of gemcitabine and gefitinib in the treatment of head and neck carcinoma. *Cancer Res* 66, 981-988 (2006).
4. Ahsan, A., et al. Role of epidermal growth factor receptor degradation in cisplatin-induced cytotoxicity in head and neck cancer. *Cancer Res* 70, 2862-2869 (2010).
5. Ahsan, A., Hiniker, S. M., Davis, M. A., Lawrence, T. S. & Nyati, M. K. Role of cell cycle in epidermal growth factor receptor inhibitor-mediated radiosensitization. *Cancer Res* 69, 5108-5114 (2009).
6. Levkowitz, G., et al. c-Cbl/Sli-1 regulates endocytic sorting and ubiquitination of the epidermal growth factor receptor. *Genes Dev* 12, 3663-3674 (1998).
7. Levkowitz, G., et al. Ubiquitin ligase activity and tyrosine phosphorylation underlie suppression of growth factor signaling by c-Cbl/Sli-1. *Molecular cell* 4, 1029-1040 (1999).
8. Huang, Y., Kim, S. O., Jiang, J. & Frank, S. J. Growth hormone-induced phosphorylation of epidermal growth factor (EGF) receptor in 3T3-F442A cells. Modulation of EGF-induced trafficking and signaling. *J Biol Chem* 278, 18902-18913 (2003).
9. Neckers, L., Mollapour, M. & Tsutsumi, S. The complex dance of the molecular chaperone Hsp90. *Trends Biochem Sci* 34, 223-226 (2009).
10. Workman, P. Altered states: selectively drugging the Hsp90 cancer chaperone. *Trends Mol Med* 10, 47-51 (2004).
11. Yang, S., et al. Association with HSP90 inhibits Cbl-mediated down-regulation of mutant epidermal growth factor receptors. *Cancer Res* 66, 6990-6997 (2006).
12. Shimamura, T., et al. Hsp90 inhibition suppresses mutant EGFR-T790M signaling and overcomes kinase inhibitor resistance. *Cancer Res* 68, 5827-5838 (2008).
13. Lavictoire, S. J., Parolin, D. A., Klimowicz, A. C., Kelly, J. F. & Lorimer, I. A. Interaction of Hsp90 with the nascent form of the mutant epidermal growth factor receptor EGFRvIII. *J Biol Chem* 278, 5292-5299 (2003).
14. Citri, A., et al. Hsp90 restrains ErbB-2/HER2 signalling by limiting heterodimer formation. *EMBO Rep* 5, 1165-1170 (2004).
15. Kim, Y. S., et al. Update on Hsp90 inhibitors in clinical trial. *Curr Top Med Chem* 9, 1479-1492 (2009).
16. Pratt, W. B., Morishima, Y. & Osawa, Y. The Hsp90 chaperone machinery regulates signaling by modulating ligand binding clefts. *J Biol Chem* 283, 22885-22889 (2008).
17. Futaki, S., et al. Arginine-rich peptides—An abundant source of membrane-permeable peptides having potential as carriers for intracellular protein delivery. *Journal of Biological Chemistry* 276, 5836-5840 (2001).
18. Wadia, J. S. & Dowdy, S. F. Transmembrane delivery of protein and peptide drugs by TAT-mediated transduction in the treatment of cancer. *Adv Drug Deliv Rev* 57, 579-596 (2005).
19. Sidera, K., Gaitanou, M., Stellas, D., Matsas, R. & Patsavoudi, E. A critical role for HSP90 in cancer cell invasion involves interaction with the extracellular domain of HER-2. *J Biol Chem* 283, 2031-2041 (2008).
20. Dote, H., Cerna, D., Burgan, W. E., Camphausen, K. & Tofilon, P. J. ErbB3 expression predicts tumor cell radiosensitization induced by Hsp90 inhibition. *Cancer Res* 65, 6967-6975 (2005).
21. Pick, E., et al. High HSP90 expression is associated with decreased survival in breast cancer. *Cancer Res* 67, 2932-2937 (2007).
22. Feng, F. Y., et al. Role of epidermal growth factor receptor degradation in gemcitabine-mediated cytotoxicity. *Oncogene* 26, 3431-3439 (2007).
23. Sreekumar, A., et al. Re: Florian Jentzmik, Carsten Stephan, Kurt Miller, et al. Sarcosine in urine after digital rectal examination fails as a marker in prostate cancer 24. Niwa, H., et al. Antitumor effects of epidermal growth factor receptor antisense oligonucleotides in combination with docetaxel in squamous cell carcinoma of the head and neck. *Clin Cancer Res* 9, 5028-5035 (2003).
25. Bao, R., et al. Targeting heat shock protein 90 with CUDC-305 overcomes erlotinib resistance in non-small cell lung cancer. *Mol Cancer Ther* 8, 3296-3306 (2009).
26. Sato, S., Fujita, N. & Tsuruo, T. Modulation of Akt kinase activity by binding to Hsp90. *Proc Natl Acad Sci USA* 97, 10832-10837 (2000).
27. Gyurkocza, B., et al. Antileukemic activity of shepherdin and molecular diversity of hsp90 inhibitors. *J Natl Cancer Inst* 98, 1068-1077 (2006).
28. Plescia, J., et al. Rational design of shepherdin, a novel anticancer agent. *Cancer cell* 7, 457-468 (2005).
29. Shimamura, T., Lowell, A. M., Engelman, J. A. & Shapiro, G. I. Epidermal growth factor receptors harboring kinase domain mutations associate with the heat shock protein 90 chaperone and are destabilized following exposure to geldanamycins. *Cancer Res* 65, 6401-6408 (2005).
30. Sharp, S. & Workman, P. Inhibitors of the HSP90 molecular chaperone: current status. *Adv Cancer Res* 95, 323-348 (2006).
31. Solit, D. B., et al. Phase I trial of 17-allylamino-17-demethoxygeldanamycin in patients with advanced cancer. *Clinical Cancer Research* 13, 1775-1782 (2007).
32. Price, J. T., et al. The heat shock protein 90 inhibitor, 17-allylamino-17-demethoxygeldanamycin, enhances osteoclast formation and potentiates bone metastasis of a human breast cancer cell line. *Cancer Res* 65, 4929-4938 (2005).

What is claimed is:

1. A composition comprising a compound that inhibits a binding interaction between an epidermal growth factor receptor (EGFR) and a heat shock protein 90 (HSP90) wherein the compound consists of the amino acid sequence SVDNPH (SEQ ID NO: 15), or SVDNPHV (SEQ ID NO: 16), or SVDNPHVX (SEQ ID NO: 17) fused to a cell penetrating peptide (CPP).

2. A composition comprising a compound that inhibits a binding interaction between an epidermal growth factor receptor (EGFR) and a heat shock protein 90 (HSP90) wherein the compound consists of an amino acid sequence selected from the group consisting of:

```
AVDNPH,     (SEQ ID NO: 25)
DVDNPH,     (SEQ ID NO: 26)
IVDNPH,     (SEQ ID NO: 27)
SVGNPH,     (SEQ ID NO: 28)
SVDNGH,     (SEQ ID NO: 29)
and
SVAAPH.     (SEQ ID NO: 30)
``` fused to a cell penetrating peptide (CPP).

3. A composition comprising a compound that inhibits a binding interaction between an epidermal growth factor receptor (EGFR) and a heat shock protein 90 (HSP90) wherein the compound consists of the amino acid sequence XDNPHX (SEQ ID NO: 32) fused to a cell penetrating peptide (CPP).

4. A composition comprising a compound that inhibits a binding interaction between an epidermal growth factor receptor (EGFR) and a heat shock protein 90 (HSP90) wherein the compound consists of the amino acid sequence SXDNPHXX (SEQ ID NO: 33) fused to a cell penetrating peptide (CPP).

5. The composition of claim 1, 2, 3, or 4, comprising an intramolecular bridge which covalently links the side chains of two amino acids of the compound.

6. The composition of claim 5, wherein the side chains of the amino acids at positions 1 and 6 are covalently linked by the intramolecular bridge.

7. The composition of claim 1, 2, 3, or 4, comprising a pharmaceutically acceptable carrier, diluent, or excipient.

8. A method of treating a subject comprising administering to the subject a composition of claim 7 in an amount effective to treat the subject.

9. The method of claim 8, wherein the subject is characterized by overexpression of EGFR or expression of a mutant EGFR.

10. A method of sensitizing a subject, comprising administering to the subject a composition of claim 1, 2, 3, or 4 in an amount effective to sensitize the subject to a therapy.

11. A kit comprising the composition of claim 1, 2, 3, or 4 in combination with an agent utilized in radiation therapy or chemotherapy.

* * * * *

SEQUENCE LISTING

```
<160> NUMBER OF SEQ ID NOS: 35

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255
```

```
Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670
```

-continued

```
Ile Val Arg Lys Arg Thr Leu Arg Arg Leu Leu Gln Glu Arg Glu Leu
675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
```

```
                    1085                1090                1095
Lys Arg Pro Ala Gly Ser Val Gln Asn Pro Val Tyr His Asn Gln
    1100                1105                1110
Pro Leu Asn Pro Ala Pro Ser Arg Asp Pro His Tyr Gln Asp Pro
    1115                1120                1125
His Ser Thr Ala Val Gly Asn Pro Glu Tyr Leu Asn Thr Val Gln
    1130                1135                1140
Pro Thr Cys Val Asn Ser Thr Phe Asp Ser Pro Ala His Trp Ala
    1145                1150                1155
Gln Lys Gly Ser His Gln Ile Ser Leu Asp Asn Pro Asp Tyr Gln
    1160                1165                1170
Gln Asp Phe Phe Pro Lys Glu Ala Lys Pro Asn Gly Ile Phe Lys
    1175                1180                1185
Gly Ser Thr Ala Glu Asn Ala Glu Tyr Leu Arg Val Ala Pro Gln
    1190                1195                1200
Ser Ser Glu Phe Ile Gly Ala
    1205                1210

<210> SEQ ID NO 2
<211> LENGTH: 628
<212> TYPE: PRT
<213> ORGANISM: Homo sapiens

<400> SEQUENCE: 2

Met Arg Pro Ser Gly Thr Ala Gly Ala Ala Leu Leu Ala Leu Leu Ala
1               5                   10                  15
Ala Leu Cys Pro Ala Ser Arg Ala Leu Glu Glu Lys Lys Val Cys Gln
                20                  25                  30
Gly Thr Ser Asn Lys Leu Thr Gln Leu Gly Thr Phe Glu Asp His Phe
            35                  40                  45
Leu Ser Leu Gln Arg Met Phe Asn Asn Cys Glu Val Val Leu Gly Asn
    50                  55                  60
Leu Glu Ile Thr Tyr Val Gln Arg Asn Tyr Asp Leu Ser Phe Leu Lys
65                  70                  75                  80
Thr Ile Gln Glu Val Ala Gly Tyr Val Leu Ile Ala Leu Asn Thr Val
                85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
        115                 120                 125
Lys Thr Gly Leu Lys Glu Leu Pro Met Arg Asn Leu Gln Glu Ile Leu
    130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
    210                 215                 220
Gly Lys Ser Pro Ser Asp Cys Cys His Asn Gln Cys Ala Ala Gly Cys
225                 230                 235                 240
```

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Ser
625

<210> SEQ ID NO 3
<211> LENGTH: 405
<212> TYPE: PRT

-continued

<213> ORGANISM: Homo sapiens

<400> SEQUENCE: 3

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400
```

```
Ile Thr Gly Leu Ser
            405

<210> SEQ ID NO 4
<211> LENGTH: 705
<212> TYPE: PRT
<213> ORGANISM: Homo sapiens

<400> SEQUENCE: 4

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
            660                 665                 670

Ser Leu Leu Pro Ser Glu Phe Gln Leu Gly Trp Gly Cys Ser His
        675                 680                 685

Leu His Ala Trp Pro Ser Ala Ser Val Ile Ile Thr Ala Ser Ser Cys
    690                 695                 700

His
705

<210> SEQ ID NO 5
<211> LENGTH: 1210
<212> TYPE: PRT
<213> ORGANISM: Artificial Sequence
<220> FEATURE:
<223> OTHER INFORMATION: Synthetic peptide

<400> SEQUENCE: 5

Met Arg Pro Ser Gly Thr Ala Gly Ala Ala Leu Leu Ala Leu Leu Ala
1               5                   10                  15

```
Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
             100                 105                 110

Tyr Glu Asn Ser Tyr Ala Leu Ala Val Leu Ser Asn Tyr Asp Ala Asn
         115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                 165                 170                 175

Ser Met Asp Phe Gln Asn His Leu Gly Ser Cys Gln Lys Cys Asp Pro
             180                 185                 190

Ser Cys Pro Asn Gly Ser Cys Trp Gly Ala Gly Glu Glu Asn Cys Gln
         195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                 245                 250                 255

Glu Ala Thr Cys Lys Asp Thr Cys Pro Pro Leu Met Leu Tyr Asn Pro
             260                 265                 270

Thr Thr Tyr Gln Met Asp Val Asn Pro Glu Gly Lys Tyr Ser Phe Gly
         275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                 325                 330                 335

Cys Asn Gly Ile Gly Ile Gly Glu Phe Lys Asp Ser Leu Ser Ile Asn
             340                 345                 350

Ala Thr Asn Ile Lys His Phe Lys Asn Cys Thr Ser Ile Ser Gly Asp
         355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                 405                 410                 415

Leu His Ala Phe Glu Asn Leu Glu Ile Ile Arg Gly Arg Thr Lys Gln
             420                 425                 430
```

-continued

His Gly Gln Phe Ser Leu Ala Val Val Ser Leu Asn Ile Thr Ser Leu
              435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
770                 775                 780
Thr Val Gln Leu Ile Met Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
835                 840                 845
Gln His Val Lys Ile Thr Asp Phe Gly Leu Ala Lys Leu Leu Gly Ala

```
                 850                 855                 860
Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
        930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 6
<211> LENGTH: 942
<212> TYPE: PRT
<213> ORGANISM: Artificial Sequence
<220> FEATURE:
<223> OTHER INFORMATION: Synthetic peptide
```

<400> SEQUENCE: 6

```
Met Arg Pro Ser Gly Thr Tyr Gln Met Asp Val Asn Pro Glu Gly Lys
1               5                   10                  15

Tyr Ser Phe Gly Ala Thr Cys Val Lys Lys Cys Pro Arg Asn Tyr Val
            20                  25                  30

Val Thr Asp His Gly Ser Cys Val Arg Ala Cys Gly Ala Asp Ser Tyr
                35                  40                  45

Glu Met Glu Glu Asp Gly Val Arg Lys Cys Lys Lys Cys Glu Gly Pro
        50                  55                  60

Cys Arg Lys Val Cys Asn Gly Ile Gly Ile Gly Glu Phe Lys Asp Ser
65                  70                  75                  80

Leu Ser Ile Asn Ala Thr Asn Ile Lys His Phe Lys Asn Cys Thr Ser
                85                  90                  95

Ile Ser Gly Asp Leu His Ile Leu Pro Val Ala Phe Arg Gly Asp Ser
                100                 105                 110

Phe Thr His Thr Pro Pro Leu Asp Pro Gln Glu Leu Asp Ile Leu Lys
            115                 120                 125

Thr Val Lys Glu Ile Thr Gly Phe Leu Leu Ile Gln Ala Trp Pro Glu
130                 135                 140

Asn Arg Thr Asp Leu His Ala Phe Glu Asn Leu Glu Ile Ile Arg Gly
145                 150                 155                 160

Arg Thr Lys Gln His Gly Gln Phe Ser Leu Ala Val Val Ser Leu Asn
                165                 170                 175

Ile Thr Ser Leu Gly Leu Arg Ser Leu Lys Glu Ile Ser Asp Gly Asp
            180                 185                 190

Val Ile Ile Ser Gly Asn Lys Asn Leu Cys Tyr Ala Asn Thr Ile Asn
        195                 200                 205

Trp Lys Lys Leu Phe Gly Thr Ser Gly Gln Lys Thr Lys Ile Ile Ser
210                 215                 220

Asn Arg Gly Glu Asn Ser Cys Lys Ala Thr Gly Gln Val Cys His Ala
225                 230                 235                 240

Leu Cys Ser Pro Glu Gly Cys Trp Gly Pro Glu Pro Arg Asp Cys Val
                245                 250                 255

Ser Cys Arg Asn Val Ser Arg Gly Arg Glu Cys Val Asp Lys Cys Asn
            260                 265                 270

Leu Leu Glu Gly Glu Pro Arg Glu Phe Val Glu Asn Ser Glu Cys Ile
        275                 280                 285

Gln Cys His Pro Glu Cys Leu Pro Gln Ala Met Asn Ile Thr Cys Thr
        290                 295                 300

Gly Arg Gly Pro Asp Asn Cys Ile Gln Cys Ala His Tyr Ile Asp Gly
305                 310                 315                 320

Pro His Cys Val Lys Thr Cys Pro Ala Gly Val Met Gly Glu Asn Asn
                325                 330                 335

Thr Leu Val Trp Lys Tyr Ala Asp Ala Gly His Val Cys His Leu Cys
            340                 345                 350

His Pro Asn Cys Thr Tyr Gly Cys Thr Gly Pro Gly Leu Glu Gly Cys
        355                 360                 365

Pro Thr Asn Gly Pro Lys Ile Pro Ser Ile Ala Thr Gly Met Val Gly
        370                 375                 380

Ala Leu Leu Leu Leu Leu Val Val Ala Leu Gly Ile Gly Leu Phe Met
385                 390                 395                 400

Arg Arg Arg His Ile Val Arg Lys Arg Thr Leu Arg Arg Leu Leu Gln
                405                 410                 415
```

-continued

Glu Arg Glu Leu Val Glu Pro Leu Thr Pro Ser Gly Glu Ala Pro Asn
            420                 425                 430

Gln Ala Leu Leu Arg Ile Leu Lys Glu Thr Glu Phe Lys Lys Ile Lys
            435                 440                 445

Val Leu Gly Ser Gly Ala Phe Gly Thr Val Tyr Lys Gly Leu Trp Ile
450                 455                 460

Pro Glu Gly Glu Lys Val Lys Ile Pro Val Ala Ile Lys Glu Leu Arg
465                 470                 475                 480

Glu Ala Thr Ser Pro Lys Ala Asn Lys Glu Ile Leu Asp Glu Ala Tyr
            485                 490                 495

Val Met Ala Ser Val Asp Asn Pro His Val Cys Arg Leu Leu Gly Ile
            500                 505                 510

Cys Leu Thr Ser Thr Val Gln Leu Ile Thr Gln Leu Met Pro Phe Gly
            515                 520                 525

Cys Leu Leu Asp Tyr Val Arg Glu His Lys Asp Asn Ile Gly Ser Gln
            530                 535                 540

Tyr Leu Leu Asn Trp Cys Val Gln Ile Ala Lys Gly Met Asn Tyr Leu
545                 550                 555                 560

Glu Asp Arg Arg Leu Val His Arg Asp Leu Ala Ala Arg Asn Val Leu
            565                 570                 575

Val Lys Thr Pro Gln His Val Lys Ile Thr Asp Phe Gly Leu Ala Lys
            580                 585                 590

Leu Leu Gly Ala Glu Glu Lys Glu Tyr His Ala Glu Gly Gly Lys Val
            595                 600                 605

Pro Ile Lys Trp Met Ala Leu Glu Ser Ile Leu His Arg Ile Tyr Thr
            610                 615                 620

His Gln Ser Asp Val Trp Ser Tyr Gly Val Thr Val Trp Glu Leu Met
625                 630                 635                 640

Thr Phe Gly Ser Lys Pro Tyr Asp Gly Ile Pro Ala Ser Glu Ile Ser
            645                 650                 655

Ser Ile Leu Glu Lys Gly Glu Arg Leu Pro Gln Pro Pro Ile Cys Thr
            660                 665                 670

Ile Asp Val Tyr Met Ile Met Val Lys Cys Trp Met Ile Asp Ala Asp
            675                 680                 685

Ser Arg Pro Lys Phe Arg Glu Leu Ile Ile Glu Phe Ser Lys Met Ala
690                 695                 700

Arg Asp Pro Gln Arg Tyr Leu Val Ile Gln Gly Asp Glu Arg Met His
705                 710                 715                 720

Leu Pro Ser Pro Thr Asp Ser Asn Phe Tyr Arg Ala Leu Met Asp Glu
            725                 730                 735

Glu Asp Met Asp Asp Val Val Asp Ala Asp Glu Tyr Leu Ile Pro Gln
            740                 745                 750

Gln Gly Phe Phe Ser Ser Pro Ser Thr Ser Arg Thr Pro Leu Leu Ser
            755                 760                 765

Ser Leu Ser Ala Thr Ser Asn Asn Ser Thr Val Ala Cys Ile Asp Arg
            770                 775                 780

Asn Gly Leu Gln Ser Cys Pro Ile Lys Glu Asp Ser Phe Leu Gln Arg
785                 790                 795                 800

Tyr Ser Ser Asp Pro Thr Gly Ala Leu Thr Glu Asp Ser Ile Asp Asp
            805                 810                 815

Thr Phe Leu Pro Val Pro Glu Tyr Ile Asn Gln Ser Val Pro Lys Arg
            820                 825                 830

Pro Ala Gly Ser Val Gln Asn Pro Val Tyr His Asn Gln Pro Leu Asn
            835                 840                 845

Pro Ala Pro Ser Arg Asp Pro His Tyr Gln Asp Pro His Ser Thr Ala
    850                 855                 860

Val Gly Asn Pro Glu Tyr Leu Asn Thr Val Gln Pro Thr Cys Val Asn
865                 870                 875                 880

Ser Thr Phe Asp Ser Pro Ala His Trp Ala Gln Lys Gly Ser His Gln
                885                 890                 895

Ile Ser Leu Asp Asn Pro Asp Tyr Gln Gln Asp Phe Phe Pro Lys Glu
                900                 905                 910

Ala Lys Pro Asn Gly Ile Phe Lys Gly Ser Thr Ala Glu Asn Ala Glu
            915                 920                 925

Tyr Leu Arg Val Ala Pro Gln Ser Ser Glu Phe Ile Gly Ala
            930                 935                 940

<210> SEQ ID NO 7
<211> LENGTH: 732
<212> TYPE: PRT
<213> ORGANISM: Artificial Sequence
<220> FEATURE:
<223> OTHER INFORMATION: Synthetic peptide

<400> SEQUENCE: 7

Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
            35                  40                  45

Ile Ser Asn Ser Ser Asp Ala Leu Asp Lys Ile Arg Tyr Glu Ser Leu
        50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
                100                 105                 110

Ser Gly Thr Lys Ala Phe Met Glu Ala Leu Gln Ala Gly Ala Asp Ile
            115                 120                 125

Ser Met Ile Gly Gln Phe Gly Val Gly Phe Tyr Ser Ala Tyr Leu Val
        130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
                180                 185                 190

Asp Gln Thr Glu Tyr Leu Glu Glu Arg Arg Ile Lys Glu Ile Val Lys
            195                 200                 205

Lys His Ser Gln Phe Ile Gly Tyr Pro Ile Thr Leu Phe Val Glu Lys
        210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Ser Glu Asp Lys Pro
                245                 250                 255

```
Glu Ile Glu Asp Val Gly Ser Asp Glu Glu Glu Lys Lys Asp Gly
            260                 265                 270

Asp Lys Lys Lys Lys Lys Ile Lys Glu Lys Tyr Ile Asp Gln Glu
        275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
            340                 345                 350

Glu Asn Arg Lys Lys Lys Asn Asn Ile Lys Leu Tyr Val Arg Arg Val
        355                 360                 365

Phe Ile Met Asp Asn Cys Glu Glu Leu Ile Pro Glu Tyr Leu Asn Phe
    370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
            420                 425                 430

Asn Tyr Lys Lys Phe Tyr Glu Gln Phe Ser Lys Asn Ile Lys Leu Gly
        435                 440                 445

Ile His Glu Asp Ser Gln Asn Arg Lys Lys Leu Ser Glu Leu Leu Arg
    450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
            500                 505                 510

Lys His Gly Leu Glu Val Ile Tyr Met Ile Glu Pro Ile Asp Glu Tyr
        515                 520                 525

Cys Val Gln Gln Leu Lys Glu Phe Glu Gly Lys Thr Leu Val Ser Val
    530                 535                 540

Thr Lys Glu Gly Leu Glu Leu Pro Glu Asp Glu Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Val Ser Asn Arg Leu
            580                 585                 590

Val Thr Ser Pro Cys Cys Ile Val Thr Ser Thr Tyr Gly Trp Thr Ala
        595                 600                 605

Asn Met Glu Arg Ile Met Lys Ala Gln Ala Leu Arg Asp Asn Ser Thr
    610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
```

```
                675                 680                 685

Tyr Arg Met Ile Lys Leu Gly Leu Gly Ile Asp Glu Asp Pro Thr
690                 695                 700

Ala Asp Asp Thr Ser Ala Val Thr Glu Glu Met Pro Pro Leu Glu
705                 710                 715                 720

Gly Asp Asp Asp Thr Ser Arg Met Glu Glu Val Asp
                725                 730

<210> SEQ ID NO 8
<211> LENGTH: 268
<212> TYPE: PRT
<213> ORGANISM: Artificial Sequence
<220> FEATURE:
<223> OTHER INFORMATION: Synthetic peptide

<400> SEQUENCE: 8

Leu Val Glu Pro Leu Thr Pro Ser Gly Glu Ala Pro Asn Gln Ala Leu
1               5                   10                  15

Leu Arg Ile Leu Lys Glu Thr Glu Phe Lys Ile Lys Val Leu Gly
                20                  25                  30

Ser Gly Ala Phe Gly Thr Val Tyr Lys Gly Leu Trp Ile Pro Glu Gly
                35                  40                  45

Glu Lys Val Lys Ile Pro Val Ala Ile Lys Glu Leu Arg Glu Ala Thr
50                  55                  60

Ser Pro Lys Ala Asn Lys Glu Ile Leu Asp Glu Ala Tyr Val Met Ala
65                  70                  75                  80

Ser Val Asp Asn Pro His Val Cys Arg Leu Leu Gly Ile Cys Leu Thr
                85                  90                  95

Ser Thr Val Gln Leu Ile Thr Gln Leu Met Pro Phe Gly Cys Leu Leu
                100                 105                 110

Asp Tyr Val Arg Glu His Lys Asp Asn Ile Gly Ser Gln Tyr Leu Leu
                115                 120                 125

Asn Trp Cys Val Gln Ile Ala Lys Gly Met Asn Tyr Leu Glu Asp Arg
                130                 135                 140

Arg Leu Val His Arg Asp Leu Ala Ala Arg Asn Val Leu Val Lys Thr
145                 150                 155                 160

Pro Gln His Val Lys Ile Thr Asp Phe Gly Leu Ala Lys Leu Leu Gly
                165                 170                 175

Ala Glu Glu Lys Glu Tyr His Ala Glu Gly Gly Lys Val Pro Ile Lys
                180                 185                 190

Trp Met Ala Leu Glu Ser Ile Leu His Arg Ile Tyr Thr His Gln Ser
                195                 200                 205

Asp Val Trp Ser Tyr Gly Val Thr Val Trp Glu Leu Met Thr Phe Gly
                210                 215                 220

Ser Lys Pro Tyr Asp Gly Ile Pro Ala Ser Glu Ile Ser Ser Ile Leu
225                 230                 235                 240

Glu Lys Gly Glu Arg Leu Pro Gln Pro Pro Ile Cys Thr Ile Asp Val
                245                 250                 255

Tyr Met Ile Met Val Lys Cys Trp Met Ile Asp Ala
                260                 265

<210> SEQ ID NO 9
<211> LENGTH: 21
<212> TYPE: PRT
<213> ORGANISM: Artificial Sequence
<220> FEATURE:
<223> OTHER INFORMATION: Synthetic peptide
```

<400> SEQUENCE: 9

Asp Glu Ala Tyr Val Met Ala Ser Val Asp Asn Pro His Val Cys Arg
1               5                   10                  15

Leu Leu Gly Ile Cys
            20

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Ser Val Asp Asn Pro His
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Ser Val Asp Asn Pro His Val Cys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Arg Leu Leu Gly Ile Cys
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Asp Asn Pro His
1

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Arg Leu Leu Gly Ile Cys
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Ser Val Asp Asn Pro His
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Ser Val Asp Asn Pro His Val
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 17

Ser Val Asp Asn Pro His Val Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Ser Val Asp Asn Pro His Val Cys
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 19

Xaa Val Xaa Asn Xaa His
1               5

<210> SEQ ID NO 20
<211> LENGTH: 6

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Xaa Val Xaa Asn Pro His
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 21

Xaa Val Asp Asn Pro His
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 22

Ser Val Xaa Asn Xaa His
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 23

Ser Val Xaa Asn Pro His
1               5

<210> SEQ ID NO 24
<211> LENGTH: 6
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 24

Ser Val Asp Asn Xaa His
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Ala Val Asp Asn Pro His
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Asp Val Asp Asn Pro His
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide

<400> SEQUENCE: 27

Ile Val Asp Asn Pro His
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide

<400> SEQUENCE: 28

Ser Val Gly Asn Pro His
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29

Ser Val Asp Asn Gly His
1               5

<210> SEQ ID NO 30
<211> LENGTH: 6
```

```
<212> TYPE: PRT
<213> ORGANISM: Artificial Sequence
<220> FEATURE:
<223> OTHER INFORMATION: Synthetic peptide

<400> SEQUENCE: 30

Ser Val Ala Ala Pro His
1               5

<210> SEQ ID NO 31
<211> LENGTH: 11
<212> TYPE: PRT
<213> ORGANISM: Artificial Sequence
<220> FEATURE:
<223> OTHER INFORMATION: Synthetic peptide

<400> SEQUENCE: 31

Tyr Gly Arg Lys Lys Arg Arg Gln Arg Arg Arg
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 32

Xaa Asp Asn Pro His Xaa
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 33

Ser Xaa Asp Asn Pro His Xaa Xaa
1               5

<210> SEQ ID NO 34
<211> LENGTH: 1210
<212> TYPE: PRT
<213> ORGANISM: Artificial Sequence
<220> FEATURE:
<223> OTHER INFORMATION: Synthetic peptide

<400> SEQUENCE: 34

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
```

```
                    20                  25                  30
Gly Thr Ser Asn Lys Leu Thr Gln Leu Gly Thr Phe Glu Asp His Phe
                35                  40                  45

Leu Ser Leu Gln Arg Met Phe Asn Asn Cys Glu Val Val Leu Gly Asn
            50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
            130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
            210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445
```

```
Gly Leu Arg Ser Leu Lys Glu Ile Ser Asp Gly Asp Val Ile Ile Ser
            450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
            690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
            770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
```

Leu Val His Arg Asp Leu Ala Ala Arg Asn Val Leu Lys Thr Pro
            835                 840                 845

Gln His Val Lys Ile Thr Asp Phe Gly Arg Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
            965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
            995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200

Ser Ser  Glu Phe Ile Gly Ala
    1205                1210

<210> SEQ ID NO 35
<211> LENGTH: 6
<212> TYPE: PRT

```
<213> ORGANISM: Artificial Sequence
<220> FEATURE:
<223> OTHER INFORMATION: Synthetic peptide

<400> SEQUENCE: 35

Asn His Val Pro Ser Asp
1               5
```